United States Patent
Schiefer et al.

(10) Patent No.: US 10,913,732 B2
(45) Date of Patent: *Feb. 9, 2021

(54) FUROXANS AS THERAPIES FOR NEURODEGENERATIVE DISORDERS

(71) Applicant: The University of Toledo, Toledo, OH (US)

(72) Inventors: Isaac Schiefer, Toledo, OH (US); Zahoor Shah, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/774,596

(22) Filed: Jan. 28, 2020

(65) Prior Publication Data

US 2020/0172526 A1  Jun. 4, 2020

Related U.S. Application Data

(63) Continuation-in-part of application No. 16/349,431, filed as application No. PCT/US2017/061503 on Nov. 14, 2017, now Pat. No. 10,590,119.

(60) Provisional application No. 62/422,293, filed on Nov. 15, 2016.

(51) Int. Cl.
*C07D 413/06* (2006.01)
*C07D 491/048* (2006.01)
*C07D 491/056* (2006.01)

(52) U.S. Cl.
CPC ....... *C07D 413/06* (2013.01); *C07D 491/048* (2013.01); *C07D 491/056* (2013.01)

(58) Field of Classification Search
CPC .................................. C07D 413/06
USPC ...................................... 514/326
See application file for complete search history.

(56) References Cited

PUBLICATIONS

Schiefer. J. Med. Chem. 2012, 55, 3076-3087.*
Monge, Pharmazie (1998), 53(10), 698-702.*
Monge, Pharmazie (1998), 53(11), 758-764.*
Pudukulatham, Molecular Pain, vol. 12: 1-10, 2016, p. 3.*

* cited by examiner

*Primary Examiner* — Nizal S Chandrakumar
(74) *Attorney, Agent, or Firm* — MacMillan, Sobanski & Todd, LLC

(57) ABSTRACT

Furoxan compounds, compositions comprising the same, and methods of making and using the same, are described.

28 Claims, 29 Drawing Sheets
(16 of 29 Drawing Sheet(s) Filed in Color)

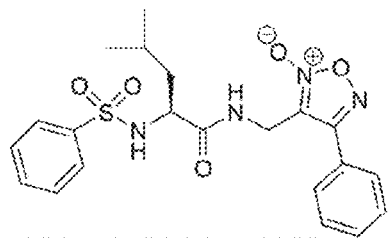
Molecular Weight: 444.51
tPSA: 131.6
CLogP: 2.961
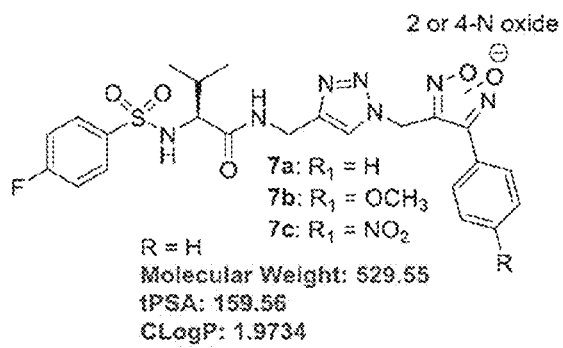
7a: R₁ = H
7b: R₁ = OCH₃
7c: R₁ = NO₂
R = H
Molecular Weight: 529.55
tPSA: 159.56
CLogP: 1.9734
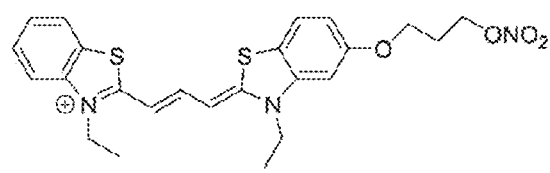
21   Molecular Weight: 484.61
tPSA: 76.52
CLogP: 1.42
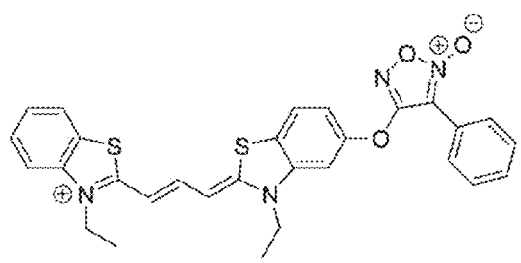
22   Molecular Weight: 541.66
tPSA: 71.81
CLogP: 4.43
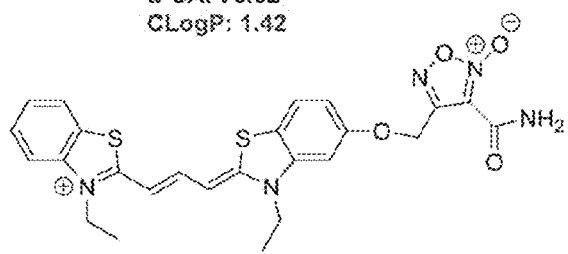
23   Molecular Weight: 522.62
tPSA: 114.9
CLogP: 0.77
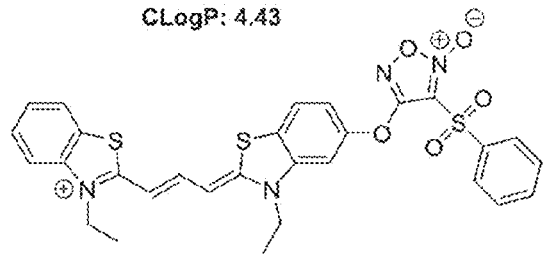
24   Molecular Weight: 605.72
tPSA: 105.95
CLogP: 2.78
PRIOR ART FIG. 1B

Table 1. Synthesis of select embodiments

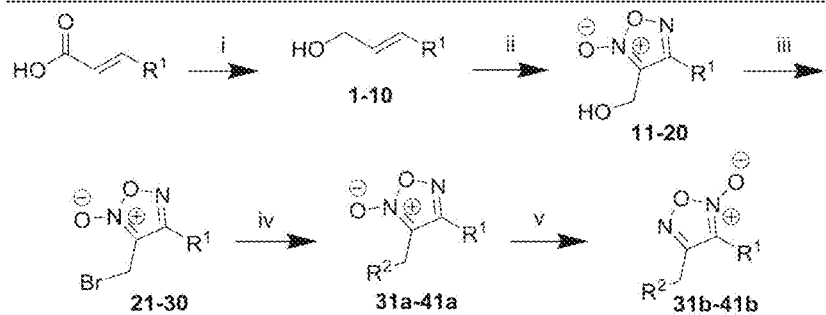

| Entry | R₁ | Z₁ |
|---|---|---|
| 31a-b | 4-F-phenyl | 4-methylpiperidinyl |
| 32a-b | 4-CF₃-phenyl | 4-methylpiperidinyl |
| 33a-b | 4-Br-phenyl | 4-methylpiperidinyl |
| 34a-b | 4-OCHF₂-phenyl | 4-methylpiperidinyl |
| 35a-b | 4-NO₂-phenyl | 4-methylpiperidinyl |
| 36a-b | 4-OMe-phenyl | 4-methylpiperidinyl |
| 37a-b | 4-OCF₃-phenyl | 4-methylpiperidinyl |
| 38a-b | 4-Me-phenyl | 4-methylpiperidinyl |
| 39a-b | 4-Cl-phenyl | 4-methylpiperidinyl |
| 40a-b | phenyl (H) | 4-methylpiperidinyl |
| 41a-b | 4-F-phenyl | 4-methylpiperidinyl-d₄ |

FIG. 2B

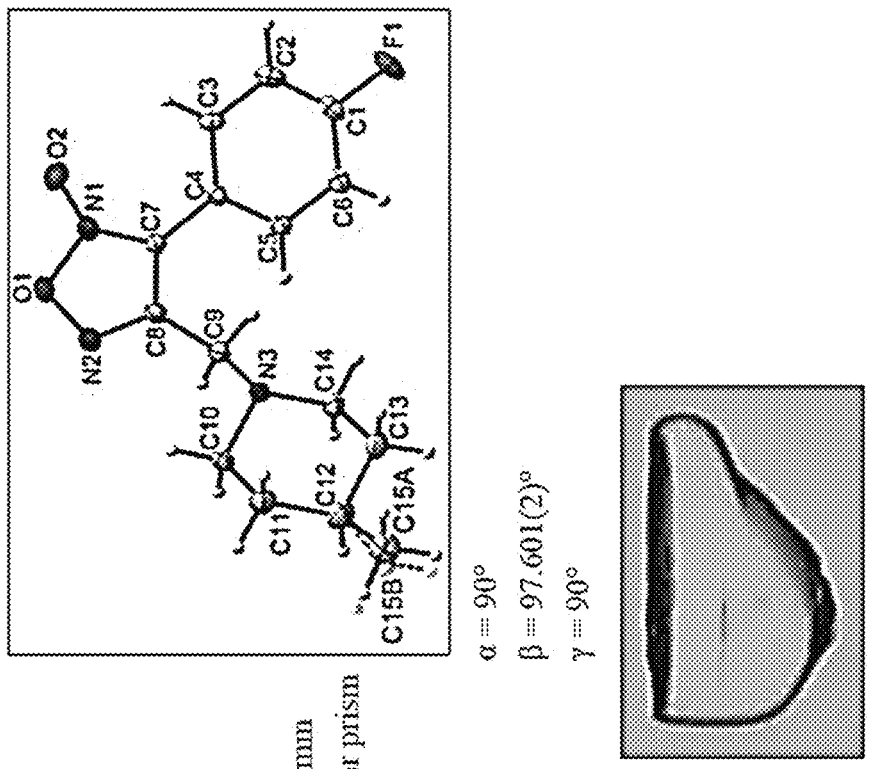

Table 2. Sample and crystal data for 31b

| | |
|---|---|
| Chemical formula | $C_{15}H_{18}FN_3O_2$ |
| Formula weight | 291.32 g/mol |
| Temperature | 100(2) K |
| Wavelength | 0.71073 Å |
| Crystal size | 0.058 × 0.156 × 0.270 mm |
| Crystal habit | clear colorless irregular prism |
| Crystal system | monoclinic |
| Space group | P 1 21/c 1 |
| Unit cell dimensions | a = 11.3374(14) Å |
| | b = 7.2234(9) Å |
| | c = 18.825(2) Å |
| Volume | 1528.1(3) Å$^3$ |
| Z | 4 |
| Density (calculated) | 1.266 g/cm$^3$ |
| Absorption coefficient | 0.094 mm$^{-1}$ |
| F(000) | 616 |

$\alpha = 90°$
$\beta = 97.601(2)°$
$\gamma = 90°$

FIG. 10

Table 3. Data collection and structure refinement for 31b.

| | |
|---|---|
| Theta range for data collection | 2.18 to 33.11° |
| Index ranges | $-16<=h<=16, -10<=k<=10, -28<=l<=28$ |
| Reflections collected | 26380 |
| Independent reflections | 5531 [R(int) = 0.0472] |
| Refinement method | Full-matrix least-squares on $F^2$ |
| Refinement program | SHELXL-2014/7 (Sheldrick, 2014) |
| Function minimized | $\Sigma\ w(F_o^2 - F_c^2)^2$ |
| Data / restraints / parameters | 5531 / 0 / 255 |
| Goodness-of-fit on $F^2$ | 1.012 |
| Final R indices | 4041 data; I>2σ(I)   R1 = 0.0517, wR2 = 0.1252 |
| | all data    R1 = 0.0794, wR2 = 0.1418 |
| Weighting scheme | $w=1/[\sigma^2(F_o^2)+(0.0662P)^2+0.6040P]$ where $P=(F_o^2+2F_c^2)/3$ |
| Largest diff. peak and hole | 0.487 and -0.540 eÅ$^{-3}$ |
| R.M.S. deviation from mean | 0.058 eÅ$^{-3}$ |

FIG. 11

Table 4. Atomic coordinates and equivalent isotropic atomic displacement parameters ($Å^2$) for 31b. U(eq) is defined as one third of the trace of the orthogonalized $U_{ij}$ tensor.

|      | x/a         | y/b         | z/c        | U(eq)       |
|------|-------------|-------------|------------|-------------|
| F1   | 0.31894(8)  | 0.54560(13) | 0.51068(4) | 0.0328(2)   |
| O1   | 0.64913(8)  | 0.57881(13) | 0.89702(5) | 0.02322(19) |
| O2   | 0.72029(8)  | 0.50985(14) | 0.79156(5) | 0.0279(2)   |
| N1   | 0.63260(9)  | 0.55790(15) | 0.81989(6) | 0.0200(2)   |
| N2   | 0.54205(10) | 0.63937(16) | 0.91653(6) | 0.0222(2)   |
| N3   | 0.25619(9)  | 0.56969(15) | 0.85780(5) | 0.0187(2)   |
| C1   | 0.36877(12) | 0.56305(18) | 0.58001(6) | 0.0224(2)   |
| C2   | 0.48134(12) | 0.63739(18) | 0.59438(7) | 0.0233(2)   |
| C3   | 0.53301(11) | 0.64905(17) | 0.66571(6) | 0.0202(2)   |
| C4   | 0.46964(10) | 0.58888(16) | 0.72049(6) | 0.0165(2)   |
| C5   | 0.35444(10) | 0.51745(16) | 0.70360(6) | 0.0177(2)   |
| C6   | 0.30356(11) | 0.50271(17) | 0.63257(6) | 0.0204(2)   |
| C7   | 0.52028(10) | 0.59930(16) | 0.79628(6) | 0.0166(2)   |
| C8   | 0.46649(10) | 0.65105(16) | 0.85770(6) | 0.0179(2)   |
| C9   | 0.34215(11) | 0.72097(17) | 0.85802(6) | 0.0195(2)   |
| C10  | 0.25910(12) | 0.4930(2)   | 0.93044(7) | 0.0241(3)   |
| C11  | 0.17264(13) | 0.3330(2)   | 0.93051(8) | 0.0300(3)   |
| C12  | 0.04613(13) | 0.3927(2)   | 0.90175(9) | 0.0335(3)   |
| C13  | 0.04648(13) | 0.4804(2)   | 0.82762(8) | 0.0331(3)   |
| C14  | 0.13635(11) | 0.6371(2)   | 0.83078(7) | 0.0256(3)   |
| C15A | 0.9623(4)   | 0.2173(6)   | 0.8909(2)  | 0.0348(8)   |
| C15B | 0.9542(3)   | 0.2489(5)   | 0.9067(2)  | 0.0344(8)   |

FIG. 12

Table 5. Bond lengths (Å) for 31b.

| | | | |
|---|---|---|---|
| F1-C1 | 1.3577(14) | O1-N2 | 1.3849(14) |
| O1-N1 | 1.4470(13) | O2-N1 | 1.2384(13) |
| N1-C7 | 1.3263(15) | N2-C8 | 1.3102(15) |
| N3-C9 | 1.4639(16) | N3-C14 | 1.4692(16) |
| N3-C10 | 1.4716(15) | C1-C2 | 1.3780(19) |
| C1-C6 | 1.3817(18) | C2-C3 | 1.3947(17) |
| C2-H2 | 0.976(19) | C3-C4 | 1.4016(16) |
| C3-H3 | 0.993(16) | C4-C5 | 1.4011(16) |
| C4-C7 | 1.4676(15) | C5-C6 | 1.3885(16) |
| C5-H5 | 0.985(17) | C6-H6 | 0.947(18) |
| C7-C8 | 1.4266(16) | C8-C9 | 1.4981(17) |
| C9-H9A | 0.934(17) | C9-H9B | 0.991(15) |
| C10-C11 | 1.5158(19) | C10-H10A | 1.027(18) |
| C10-H10B | 1.010(18) | C11-C12 | 1.527(2) |
| C11-H11A | 0.991(19) | C11-H11B | 0.959(16) |
| C12-C15B | 1.482(4) | C12-C13 | 1.533(2) |
| C12-C15A | 1.581(4) | C12-H12 | 1.06(2) |
| C13-C14 | 1.519(2) | C13-H13A | 1.01(2) |
| C13-H13B | 1.015(18) | C14-H14A | 0.979(17) |
| C14-H14B | 1.014(19) | C15A-H15A | 0.98 |
| C15A-H15B | 0.98 | C15A-H15C | 0.98 |
| C15B-H15D | 0.98 | C15B-H15E | 0.98 |
| C15B-H15F | 0.98 | | |

FIG. 13

Table 6. Bond angles (°) for 31b.

| | | | |
|---|---|---|---|
| N2-O1-N1 | 107.30(8) | O2-N1-C7 | 135.13(11) |
| O2-N1-O1 | 117.17(9) | C7-N1-O1 | 107.69(9) |
| C8-N2-O1 | 107.11(10) | C9-N3-C14 | 109.79(10) |
| C9-N3-C10 | 110.19(9) | C14-N3-C10 | 110.63(10) |
| F1-C1-C2 | 118.80(11) | F1-C1-C6 | 117.71(12) |
| C2-C1-C6 | 123.49(11) | C1-C2-C3 | 118.21(11) |
| C1-C2-H2 | 121.9(11) | C3-C2-H2 | 119.8(11) |
| C2-C3-C4 | 119.91(12) | C2-C3-H3 | 120.4(9) |
| C4-C3-H3 | 119.6(9) | C5-C4-C3 | 120.03(10) |
| C5-C4-C7 | 118.20(10) | C3-C4-C7 | 121.77(11) |
| C6-C5-C4 | 120.19(11) | C6-C5-H5 | 120.3(10) |
| C4-C5-H5 | 119.5(10) | C1-C6-C5 | 118.16(12) |
| C1-C6-H6 | 119.3(11) | C5-C6-H6 | 122.5(11) |
| N1-C7-C8 | 106.37(10) | N1-C7-C4 | 123.31(10) |
| C8-C7-C4 | 130.32(10) | N2-C8-C7 | 111.50(11) |
| N2-C8-C9 | 121.92(11) | C7-C8-C9 | 126.50(10) |
| N3-C9-C8 | 112.01(10) | N3-C9-H9A | 111.3(10) |
| C8-C9-H9A | 107.9(10) | N3-C9-H9B | 108.0(9) |
| C8-C9-H9B | 107.7(9) | H9A-C9-H9B | 109.9(13) |
| N3-C10-C11 | 110.66(11) | N3-C10-H10A | 110.2(10) |
| C11-C10-H10A | 110.2(10) | N3-C10-H10B | 108.5(10) |
| C11-C10-H10B | 111.7(10) | H10A-C10-H10B | 105.4(14) |
| C10-C11-C12 | 111.21(12) | C10-C11-H11A | 109.0(11) |
| C12-C11-H11A | 110.4(11) | C10-C11-H11B | 111.2(9) |
| C12-C11-H11B | 108.5(9) | H11A-C11-H11B | 106.5(15) |
| C15B-C12-C11 | 114.53(19) | C15B-C12-C13 | 115.7(2) |
| C11-C12-C13 | 108.91(12) | C11-C12-C15A | 109.90(19) |
| C13-C12-C15A | 106.69(19) | C15B-C12-H12 | 98.2(11) |
| C11-C12-H12 | 110.5(11) | C13-C12-H12 | 108.4(11) |
| C15A-C12-H12 | 112.3(11) | C14-C13-C12 | 110.79(12) |
| C14-C13-H13A | 109.4(12) | C12-C13-H13A | 111.1(12) |
| C14-C13-H13B | 108.9(10) | C12-C13-H13B | 108.5(10) |
| H13A-C13-H13B | 108.0(15) | N3-C14-C13 | 110.59(12) |
| N3-C14-H14A | 109.0(10) | C13-C14-H14A | 109.6(10) |
| N3-C14-H14B | 111.3(10) | C13-C14-H14B | 109.8(10) |
| H14A-C14-H14B | 106.5(15) | C12-C15A-H15A | 109.5 |
| C12-C15A-H15B | 109.5 | H15A-C15A-H15B | 109.5 |
| C12-C15A-H15C | 109.5 | H15A-C15A-H15C | 109.5 |
| H15B-C15A-H15C | 109.5 | C12-C15B-H15D | 109.5 |
| C12-C15B-H15E | 109.5 | H15D-C15B-H15E | 109.5 |
| C12-C15B-H15F | 109.5 | H15D-C15B-H15F | 109.5 |
| H15E-C15B-H15F | 109.5 | | |

FIG. 14

Table 7. Anisotropic atomic displacement parameters (Å$^2$) for 31b.
The anisotropic atomic displacement factor exponent takes the form: $-2\pi^2[\, h^2 a^{*2} U_{11} + \ldots + 2\, h\, k\, a^*\, b^*\, U_{12}\,]$

|     | $U_{11}$   | $U_{22}$   | $U_{33}$   | $U_{23}$    | $U_{13}$    | $U_{12}$    |
|-----|------------|------------|------------|-------------|-------------|-------------|
| F1  | 0.0453(5)  | 0.0384(5)  | 0.0132(3)  | 0.0006(3)   | -0.0022(3)  | 0.0002(4)   |
| O1  | 0.0209(4)  | 0.0274(4)  | 0.0196(4)  | 0.0009(3)   | -0.0038(3)  | -0.0004(3)  |
| O2  | 0.0188(4)  | 0.0335(5)  | 0.0312(5)  | -0.0035(4)  | 0.0030(4)   | 0.0045(4)   |
| N1  | 0.0189(5)  | 0.0206(5)  | 0.0197(5)  | -0.0002(4)  | -0.0006(4)  | -0.0007(4)  |
| N2  | 0.0225(5)  | 0.0246(5)  | 0.0185(5)  | 0.0007(4)   | -0.0008(4)  | -0.0027(4)  |
| N3  | 0.0164(4)  | 0.0236(5)  | 0.0157(4)  | 0.0041(4)   | 0.0009(3)   | -0.0020(4)  |
| C1  | 0.0314(6)  | 0.0220(5)  | 0.0131(5)  | -0.0004(4)  | 0.0000(4)   | 0.0047(5)   |
| C2  | 0.0323(6)  | 0.0204(5)  | 0.0185(5)  | 0.0007(4)   | 0.0086(5)   | 0.0014(5)   |
| C3  | 0.0235(6)  | 0.0179(5)  | 0.0202(5)  | -0.0012(4)  | 0.0061(4)   | -0.0001(4)  |
| C4  | 0.0189(5)  | 0.0163(5)  | 0.0143(5)  | -0.0001(4)  | 0.0021(4)   | 0.0025(4)   |
| C5  | 0.0187(5)  | 0.0186(5)  | 0.0155(5)  | 0.0005(4)   | 0.0014(4)   | 0.0021(4)   |
| C6  | 0.0216(5)  | 0.0211(5)  | 0.0175(5)  | -0.0010(4)  | -0.0008(4)  | 0.0031(4)   |
| C7  | 0.0167(5)  | 0.0169(5)  | 0.0156(5)  | 0.0008(4)   | 0.0001(4)   | -0.0009(4)  |
| C8  | 0.0205(5)  | 0.0182(5)  | 0.0147(5)  | 0.0005(4)   | 0.0010(4)   | -0.0042(4)  |
| C9  | 0.0210(5)  | 0.0206(5)  | 0.0172(5)  | 0.0001(4)   | 0.0032(4)   | -0.0010(4)  |
| C10 | 0.0223(6)  | 0.0315(6)  | 0.0178(5)  | 0.0072(5)   | 0.0005(4)   | -0.0039(5)  |
| C11 | 0.0259(6)  | 0.0326(7)  | 0.0308(7)  | 0.0110(6)   | 0.0012(5)   | -0.0068(5)  |
| C12 | 0.0231(6)  | 0.0394(8)  | 0.0381(8)  | 0.0093(6)   | 0.0043(6)   | -0.0077(6)  |
| C13 | 0.0203(6)  | 0.0418(8)  | 0.0350(7)  | 0.0078(6)   | -0.0037(5)  | -0.0055(6)  |
| C14 | 0.0197(6)  | 0.0319(7)  | 0.0247(6)  | 0.0078(5)   | 0.0004(4)   | 0.0014(5)   |

FIG. 15

Table 8. Hydrogen atomic coordinates and isotropic atomic displacement parameters ($\text{Å}^2$) for 31b.

|  | x/a | y/b | z/c | U(eq) |
|---|---|---|---|---|
| H2 | 0.5259(16) | 0.678(3) | 0.5563(10) | 0.039(5) |
| H3 | 0.6140(14) | 0.702(2) | 0.6781(8) | 0.023(4) |
| H5 | 0.3103(15) | 0.476(2) | 0.7425(9) | 0.024(4) |
| H6 | 0.2270(16) | 0.451(2) | 0.6191(9) | 0.028(4) |
| H9A | 0.3416(14) | 0.797(2) | 0.8982(9) | 0.025(4) |
| H9B | 0.3207(13) | 0.795(2) | 0.8137(8) | 0.019(4) |
| H10A | 0.2391(15) | 0.594(2) | 0.9652(9) | 0.027(4) |
| H10B | 0.3434(15) | 0.454(2) | 0.9483(9) | 0.028(4) |
| H12 | 0.0148(17) | 0.492(3) | 0.9360(11) | 0.041(5) |
| H11A | 0.1759(16) | 0.285(3) | 0.9800(10) | 0.041(5) |
| H11B | 0.1947(14) | 0.232(2) | 0.9018(8) | 0.020(4) |
| H13A | -0.0351(18) | 0.529(3) | 0.8082(11) | 0.040(5) |
| H13B | 0.0690(15) | 0.382(2) | 0.7935(9) | 0.028(4) |
| H14A | 0.1371(15) | 0.689(2) | 0.7828(9) | 0.030(4) |
| H14B | 0.1114(16) | 0.741(3) | 0.8616(10) | 0.034(5) |
| H15A | -0.1179 | 0.2559 | 0.8704 | 0.052 |
| H15B | -0.0411 | 0.1571 | 0.9372 | 0.052 |
| H15C | -0.0062 | 0.1300 | 0.8582 | 0.052 |
| H15D | -0.1245 | 0.2999 | 0.8896 | 0.052 |
| H15E | -0.0434 | 0.2095 | 0.9567 | 0.052 |
| H15F | -0.0302 | 0.1424 | 0.8771 | 0.052 |

FIG. 16

FUROXANS AS THERAPIES FOR NEURODEGENERATIVE DISORDERS

RELATED APPLICATIONS

This application is a continuation-in-part application of U.S. Ser. No. 16/349,431 filed May 13, 2019, now allowed, and claims priority to PCT/US2017/061503 filed Nov. 14, 2017 which claims priority to U.S. provisional Application No. 62/422,293 filed under 35 U.S.C. § 111(b) on Nov. 15, 2016, the disclosures of which is incorporated herein by reference in its entirety.

STATEMENT REGARDING FEDERALLY SPONSORED RESEARCH

This invention was made with no government support. The government has no rights in this invention.

BACKGROUND

Nitric oxide (NO) signaling is essential for brain activity and normal neuronal function. Disrupted NO signaling is indicated as a potential underlying pathological event in several central nervous system (CNS) disorders and neurodegenerative scenarios. Molecular classes capable of enhancing NO related signaling cascades have shown utility in a variety of neurological disorders, including stroke, depression, and Alzheimer's disease (AD).

Nitrates, such as nitroglycerin and isosorbide dinitrate, mimic the action of NO and are known as NO mimetics. Nitrates have been used clinically for over 150 years as safe and effective treatments for acute angina. Some nitrates have demonstrated potential as therapeutics for several neurological disorders in preclinical animal models, especially for the treatment of AD. Unfortunately, the development of nitrates for neurodegeneration has faced challenges for several reasons. Generally, obstacles have centralized around the intrinsic physiochemical liability of the nitrate group itself, including: 1) poor metabolic stability; 2) challenges associated with precisely monitoring levels of NO mimetic activity (i.e., the logistical challenge of characterizing pharmacokinetics); and 3) nitrates are relatively unstable in the presence of atmospheric humidity (presenting a logistical challenge during manufacturing and storage prior to use).

Nitrates are suitable for use clinically as vasodilators in incidences of acute angina because this indication requires rapid onset of activity. Hence, the poor metabolic stability of nitrates is not a liability when used to treat acute angina. The chemical reactivity of nitrates prevents them from use clinically for the CNS, where sustained low level enhancement of NO signaling is desirable.

Furoxans are slow-acting NO mimetic neuroprotective and procognitive agents that can be used as AD therapies. (FIG. 1A.) Improved synaptic function has been demonstrated upon foruxan administration in cell cultures. Further, there is evidence of reduced AD pathological hallmarks upon treatment with these agents in cell cultures, which had previously been shown for nitrates but not furoxans. PRIOR ART FIG. 1B summarizes these furoxans for the CNS. However, the use of furoxans in CNS related animal models has not been demonstrated.

There is a need in the art for new treatments for neurological disorders. It would be advantageous to discover new furoxan compounds useful for treating various neurological disorders and conditions.

SUMMARY

Provided are furoxan compounds comprising a 4-N-oxide furoxan ring substituted with an aryl or heteroaryl system on the carbon adjacent to the N-oxide, and a —CH$_2$— group opposite the aryl or heteroaryl system, where the furoxan compounds have a molecular weight less than 450 g/mol, a partition coefficient between 2.0 and 5.0, and a total polar surface area between 40 and 90. Also provided are salts, stereoisomers, racemates, hydrates, solvates, prodrugs, and polymorphs thereof.

Provided are compounds of Formula I:

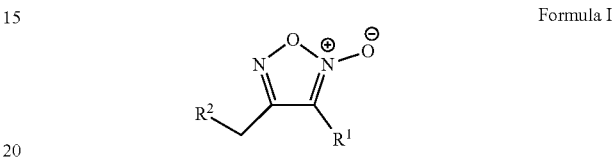

Formula I where R$^1$ is a heteroaryl, aralkyl, alkoxy, or aralkyloxy group; and R$^2$ is a is a substituted or unsubstituted heterocyclic amine.

Also provided are salts, stereoisomers, racemates, hydrates, solvates, prodrugs, and polymorphs thereof.

In certain embodiments, R$^1$ is halogen-substituted aryl group.

In certain embodiments, R$^1$ is selected from the group consisting of phenyl, 4-fluorophenyl, 4-bromophenyl, 4-chlorophenyl, 4-tetrafluoromethylphenyl, 4-difluoromethoxyphenyl, 4-nitrophenyl, 4-tetrafluoromethyoxyphenyl, and 4-methylphenyl.

In certain embodiments, R$^2$ is a deuterium-substituted hetercyclic amine.

In certain embodiments, R$^2$ is a substituted or unsubstituted heterocyclic amine; having a radical, functional group, or substituent containing at least one heterocyclic ring as well as at least one nitrogen-containing group.

In certain embodiments, the nitrogen-containing group is part of the heterocyclic ring.

In certain embodiments, the nitrogen-containing group is attached or the heterocyclic ring.

In certain embodiments, the nitrogen in the nitrogen-containing group is heteroatom of the heterocyclic ring.

In certain embodiments, the heterocyclic amines include piperidines, piperazines, thiomorpholines, morpholines, and pyrrolidines.

In certain embodiments, R$^2$ comprises 4-methylpiperidine.

In certain embodiments, R$^1$ is a halogen-substituted aryl group, and R$^2$ comprises 4-methylpiperidine.

In certain embodiments, the compound consists essentially of compound 31b:

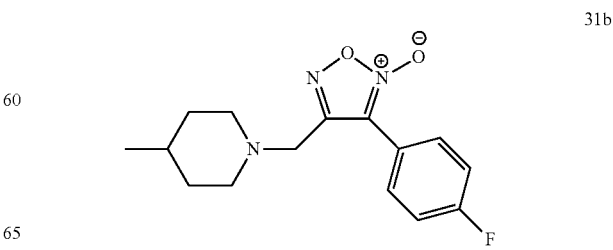

31b

In certain embodiments, the compound consists essentially of compound 32b:

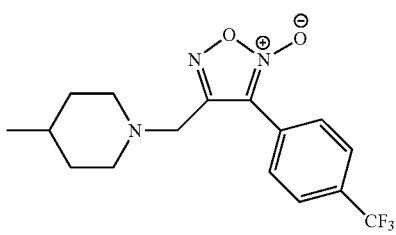

32b

In certain embodiments, the compound consists essentially of compound 33b:

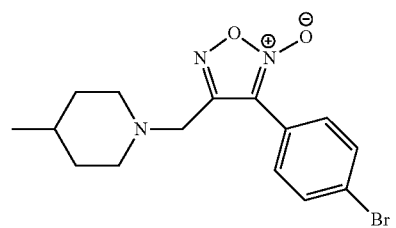

33b

In certain embodiments, the compound consists essentially of compound 34b:

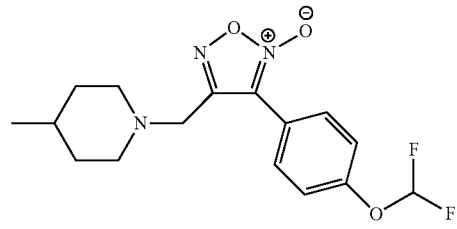

34b

In certain embodiments, the compound consists essentially of compound 35b:

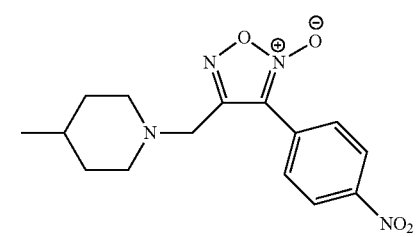

35b

In certain embodiments, the compound consists essentially of compound 36b:

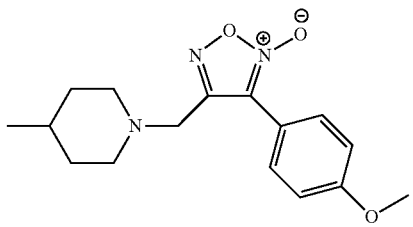

36b

In certain embodiments, the compound consists essentially of compound 37b:

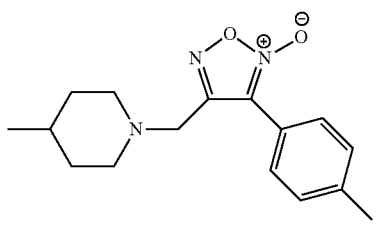

37b

In certain embodiments, the compound consists essentially of compound 38b:

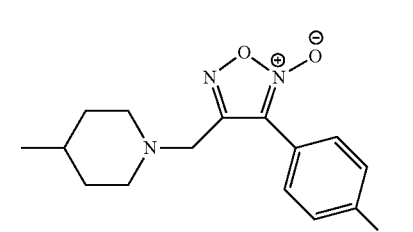

38b

In certain embodiments, the compound consists essentially of compound 39b:

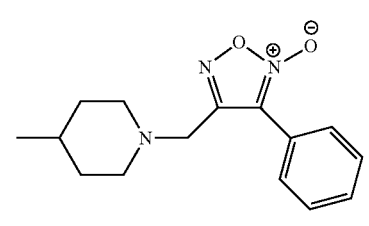

39b

In certain embodiments, the compound consists essentially of compound 40b:

40b

In certain embodiments, the compound consists essentially of compound 41b:

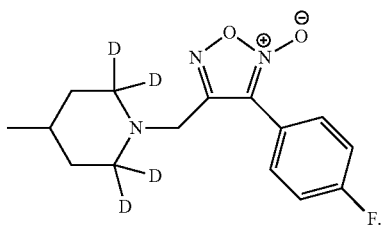

In certain embodiments, the compound consists essentially of compound:

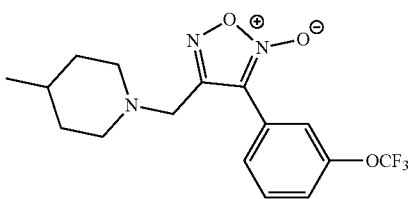 [SMILES: CC1CCN(Cc2no[n+]([O-])c2-c2cccc(OC(F)(F)F)c2)CC1]

4-((4-methylpiperidin-1-yl)methyl)-3-(3-(trifluoromethoxy)phenyl)-1,2,5-oxadiazole 2-oxide (AH-4-52)

In certain embodiments, the compound consists essentially of compound:

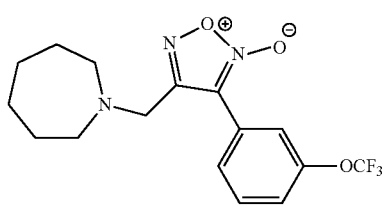

4-(azepan-1-ylmethyl)-3-(3-(trifluoromethoxy)phenyl)-1,2,5-oxadiazole 2-oxide (AH-4-53)

In certain embodiments, the compound consists essentially of compound:

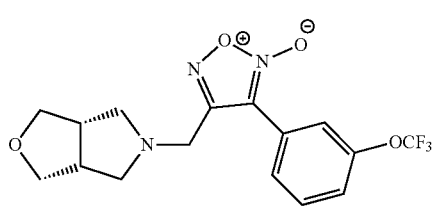

4-(((3aR,6aS)-tetrahydro-1H-furo[3,4-c]pyrrol-5(3H)-yl)methyl)-3-(3-(trifluoromethoxy)phenyl)-1,2,5-oxadiazole 2-oxide (AH-4-54)

In certain embodiments, the compound consists essentially of compound:

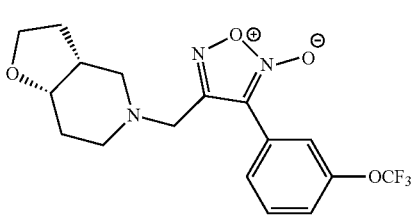

4-(((3aR,7aS)-hexahydrofuro[3,2-c]pyridin-5(4H)-yl)methyl)-3-(3-(trifluoromethoxy)phenyl)-1,2,5-oxadiazole 2-oxide (AH-4-55)

In certain embodiments, the compound consists essentially of compound:

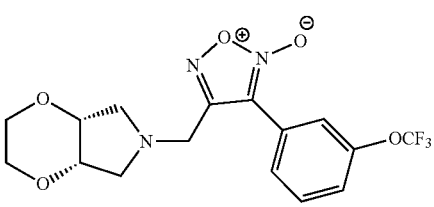

4-(((4aR,7aS)-hexahydro-6H-[1,4]dioxino[2,3-c]pyrrol-6-yl)methyl)-3-(3-(trifluoromethoxy)phenyl)-1,2,5-oxadiazole 2-oxide (AH-4-56)

In certain embodiments, the compound consists essentially of compound:

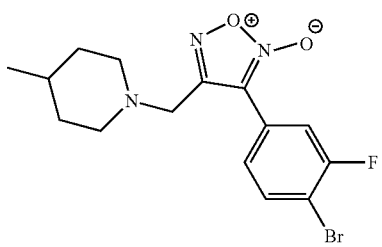

3-(4-bromo-3-fluorophenyl)-4-((4-methylpiperidin-1-yl)methyl)-1,2,5-oxadiazole 2-oxide (AH-4-58)

In certain embodiments, the compound consists essentially of compound:

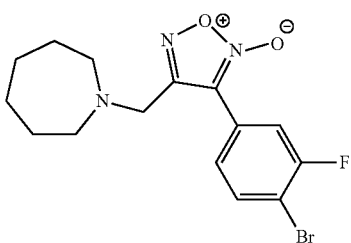

4-(azepan-1-ylmethyl)-3-(4-bromo-3-fluorophenyl)-
1,2,5-oxadiazole 2-oxide (AH-4-59)

In certain embodiments, the compound consists essentially of compound:

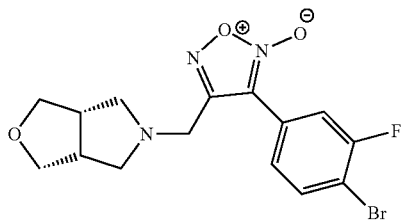

3-(4-bromo-3-fluorophenyl)-4-(((3aR,6aS)-tetrahydro-1H-furo[3,4-c]pyrrol-5(3H)-yl)methyl)-1,2,5-oxadiazole 2-oxide (AH-4-60)

In certain embodiments, the compound consists essentially of compound:

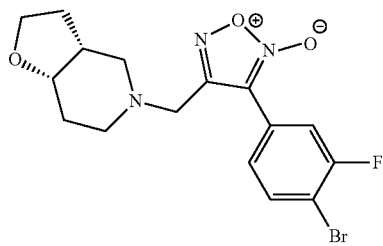

3-(4-bromo-3-fluorophenyl)-4-(((3aR,7aS)-hexahydrofuro[3,2-c]pyridin-5(4H)-yl)methyl)-1,2,5-oxadiazole 2-oxide (AH-4-61)

In certain embodiments, the compound consists essentially of compound:

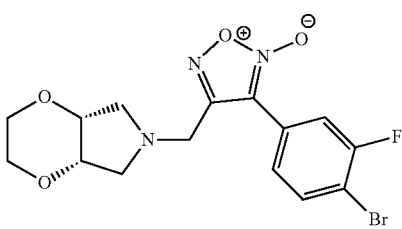

3-(4-bromo-3-fluorophenyl)-4-(((4aR,7aS)-hexahydro-6H-[1,4]dioxino[2,3-c]pyrrol-6-yl)methyl)-1,2,5-oxadiazole 2-oxide (AH-4-62)

In certain embodiments, the compound consists essentially of compound:

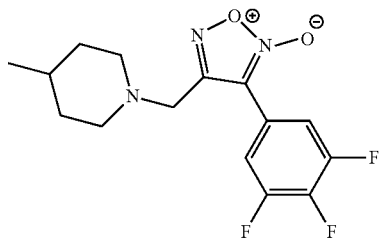

4-((4-methylpiperidin-1-yl)methyl)-3-(3,4,5-trifluorophenyl)-1,2,5-oxadiazole 2-oxide (AH-4-67)

In certain embodiments, the compound consists essentially of compound:

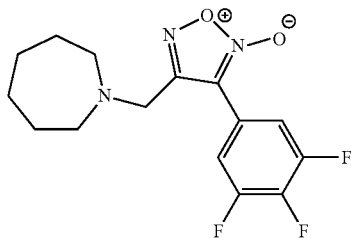

4-(azepan-1-ylmethyl)-3-(3,4,5-trifluorophenyl)-1,2,5-oxadiazole 2-oxide (AH-4-68)

In certain embodiments, the compound consists essentially of compound:

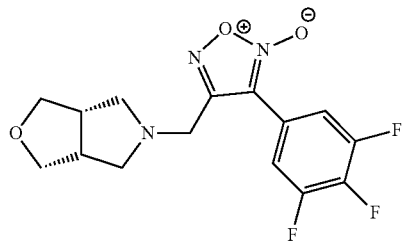

4-(((3aR,6aS)-tetrahydro-1H-furo[3,4-c]pyrrol-5(3H)-yl)methyl)-3-(3,4,5-trifluorophenyl)-1,2,5-oxadiazole 2-oxide (AH-4-69)

In certain embodiments, the compound consists essentially of compound:

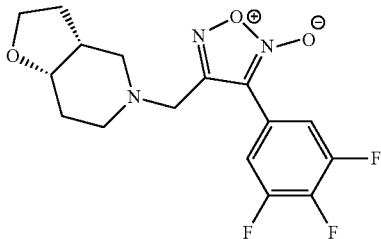

4-(((3aR,7aS)-hexahydrofuro[3,2-c]pyridin-5(4H)-yl)methyl)-3-(3,4,5-trifluorophenyl)-1,2,5-oxadiazole 2-oxide (AH-4-70)

In certain embodiments, the compound consists essentially of compound:

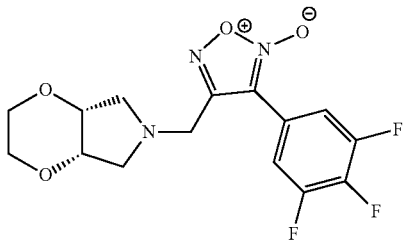

4-(((4aR,7aS)-hexahydro-6H-[1,4]dioxino[2,3-c]pyrrol-6-yl)methyl)-3-(3,4,5-trifluorophenyl)-1,2,5-oxadiazole 2-oxide (AH-4-71)

In certain embodiments, the compound consists essentially of compound:

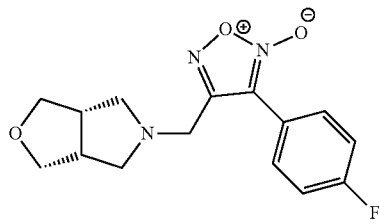

3-(4-fluorophenyl)-4-(((3aR,6aS)-tetrahydro-1H-furo[3,4-c]pyrrol-5(3H)-yl)methyl)-1,2,5-oxadiazole 2-oxide (AH-4-78)

In certain embodiments, the compound consists essentially of compound:

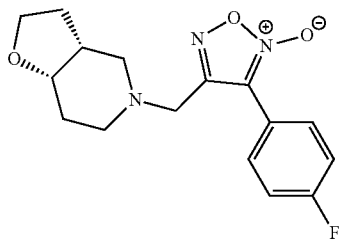 [SMILES: [O-][n+]1onc(CN2CC[C@@H]3OCC[C@@H]3C2)c1-c1ccc(F)cc1]

3-(4-fluorophenyl)-4-(((3aR,7aS)-hexahydrofuro[3,2-c]pyridin-5(4H)-yl)methyl)-1,2,5-oxadiazole 2-oxide (AH-4-79)

In certain embodiments, the compound consists essentially of compound:

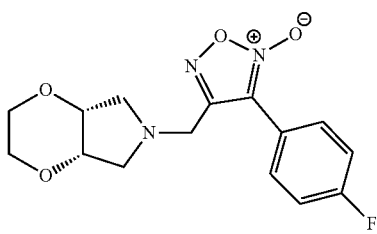 [SMILES: [O-][n+]1onc(CN2C[C@@H]3OCCO[C@@H]3C2)c1-c1ccc(F)cc1]

3-(4-fluorophenyl)-4-(((4aR,7aS)-hexahydro-6H-[1,4]dioxino[2,3-c]pyrrol-6-yl)methyl)-1,2,5-oxadiazole 2-oxide (AH-4-80)

In certain embodiments, the compound consists essentially of compound:

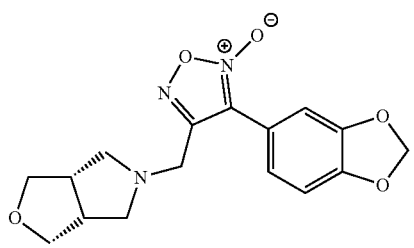

3-(benzo[d][1,3]dioxol-5-yl)-4-(((3aR,6aS)-tetrahydro-1H-furo[3,4-c]pyrrol-5(3H)-yl)methyl)-1,2,5-oxadiazole 2-oxide (AH-4-88)

In certain embodiments, the compound consists essentially of compound:

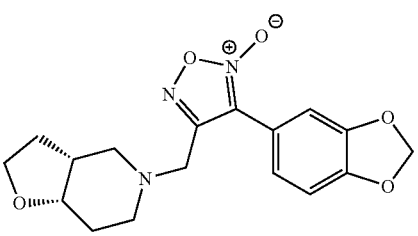 [SMILES: [O-][n+]1onc(CN2CC[C@@H]3OCC[C@@H]3C2)c1-c1ccc2c(c1)OCO2]

3-(benzo[d][1,3]dioxol-5-yl)-4-(((3aR,7aS)-hexahydrofuro[3,2-c]pyridin-5(4H)-yl)methyl)-1,2,5-oxadiazole 2-oxide (AH-4-89)

In certain embodiments, the compound consists essentially of compound:

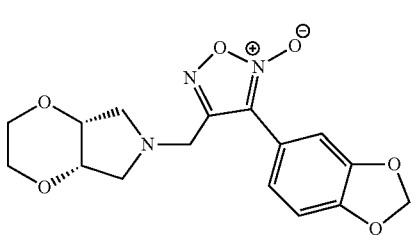 [SMILES: [O-][n+]1onc(CN2C[C@@H]3OCCO[C@@H]3C2)c1-c1ccc2c(c1)OCO2]

3-(benzo[d][1,3]dioxol-5-yl)-4-(((4aR,7aS)-hexa-hydro-6H-[1,4]dioxino[2,3-c]pyrrol-6-yl)methyl)-1,2,5-oxadiazole 2-oxide (AH-4-90)

In certain embodiments, the compound consists essentially of compound:

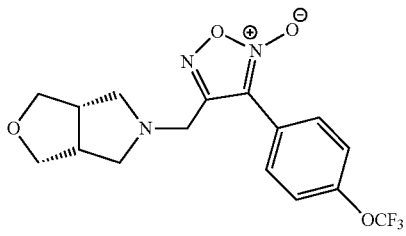

4-(((3aR,6aS)-tetrahydro-1H-furo[3,4-c]pyrrol-5(3H)-yl)methyl)-3-(4-(trifluoromethoxy)phenyl)-1,2,5-oxadiazole 2-oxide (AH-4-92)

In certain embodiments, the compound consists essentially of compound:

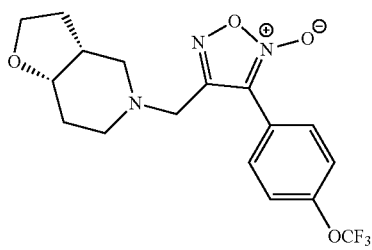 [SMILES: [O-][n+]1onc(CN2CC[C@@H]3OCC[C@@H]3C2)c1-c1ccc(OC(F)(F)F)cc1]

4-(((3aR,7aS)-hexahydrofuro[3,2-c]pyridin-5(4H)-yl)methyl)-3-(4-(trifluoromethoxy)phenyl)-1,2,5-oxadiazole 2-oxide (AH-4-93)

In certain embodiments, the compound consists essentially of compound:

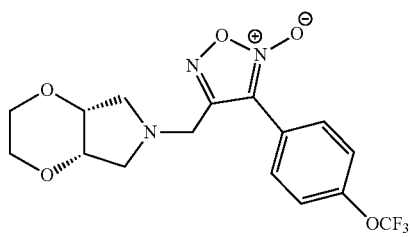 [SMILES: [O-][n+]1onc(CN2C[C@@H]3OCCO[C@@H]3C2)c1-c1ccc(OC(F)(F)F)cc1]

4-(((4aR,7aS)-hexahydro-6H-[1,4]dioxino[2,3-c]pyrrol-6-yl)methyl)-3-(4-(trifluoromethoxy)phenyl)-1,2,5-oxadiazole 2-oxide (AH-2-94)

Also provided is a pharmaceutical composition comprising an effective amount of a compound herein, and a pharmaceutically acceptable diluent, adjuvant, or excipient.

Also provided is a method of making a compound herein, the method comprising reducing a cinnamic acid to produce a cinnamyl alcohol; treating the cinnamyl alcohol in acetic acid with sodium nitrite to produce a furoxan alcohol; activating the furoxan alcohol with triphenyl phosphine and carbon tetrabromide to produce a brominated furoxan alcohol; substituting bromine in the brominated furoxan alcohol with a cap group electrophile to produce a 2-N-oxide furoxan compound; and stirring the 2-N-oxide furoxan compound in toluene for a period of time to produce a 4-N-oxide furoxan compound via microwave irradiation.

Also provided is a method of enhancing cognition in a subject, the method comprising administering an effective amount of a compound herein to a subject and enhancing cognition in the subject.

Also provided is a method of promoting neurorestorative effects in a subject, the method comprising administering an effective amount of a compound herein to a subject and promoting neurorestorative effects in the subject.

Also provided is a method of treating or ameliorating a neurodegenerative disorder, the method comprising administering an effective amount of a compound herein to a subject in need thereof and treating or ameliorating a neurodegenerative disorder in the subject. In certain embodiments, the neurodegenerative disorder is selected from the group consisting of Alzheimer's disease, dementia, stroke, traumatic brain injury (TBI), and chronic traumatic encephalopathy (CTE).

Also provided is a method of protecting against oxygen glucose deprivation (OGD), the method comprising administering an effective amount of a compound herein to a subject, and protecting against oxygen glucose deprivation in the subject.

Also provided is a method of reversing effects of NOS inhibition on pCREB, the method comprising administering an effective amount of a compound herein to a subject, and reversing effects of NOS inhibition on pCREB in the subject.

Also provided is a method of reversing memory impairment, the method comprising administering an effective amount of a compound herein, and reversing memory impairment in the subject.

Also provided is a method of improving memory impairment, the method comprising administering an effective amount of a compound herein to a subject, and improving memory impairment in the subject.

Also provided is a method of improving motor function performance, the method comprising administering an effective amount of a compound herein to a subject, and improving motor function performance in the subject.

Also provided is a kit for preparing a furoxan compound, the kit comprising a first container housing a cinnamic acid, and a second container housing one or more of a reducing agent, acetic acid, sodium nitrite, triphenyl phosphine, carbon tetrabromide, toluene, and an aryl or heteroaryl electrophile.

Also provided is a method of determining coverage or denial of health insurance reimbursement and/or payment for treatments of disease, the method comprising denying coverage or reimbursement for a treatment, where the treatment comprises administering a compound described herein.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 1B: Depiction of known furoxans.

FIG. 2B: Table 1, displaying the synthesis of non-limiting example compounds of Formula I. $^a$Reagents and conditions: i) ethyl chloroformate, TEA, then $NaBH_4$, MeOH, 45-95%; ii) $NaNO_2$, AcOH, 45-75%; iii) $CBr_4$, $PPh_3$, 75-95%; iv) $K_2CO_3$, DIPEA, DMF, 4-methylpiperidine for 31a-40a or 4-methylpiperidine-2,2,6,6-$d^4$ for 41a, 65-95%; v) toluene, reflux, 7 d, or toluene, µ-wave irradiation, 1 h.

(FIG. 5A). Incubations were placed in a temperature controlled HPLC autosampler and aliquots are analyzed by HPLC-UVvis periodically for 2-24 hr. Percent furoxan remaining was determined based on the area under the curve (AUC) of the HPLC UV-absorbance spectrum. Similarly, rat liver microsomes were incubated with 31b in the presence or absence of NADPH to determine microsomal stability (FIG. 5B). Warfarin and verapamil were used as slow and fast metabolizing controls.

FIG. 8A shows the treatment timeline, and FIG. 8B shows the results.

FIG. 9A shows the pMCAO study outline. FIG. 9B shows results of behavioral recovery assessed 4 h, 1 d, and 7 d after MCAO via rotarod. Latency to fall was normalized to 4 h post-infarct mean for each group and is represented as mean and s.e.m. (n=12). Analyzed using one way ANOVA analysis with Tukey's post-hoc test. FIG. 9C shows results of an expert blinded observer evaluation of sensory and motor deficits. Each of the seven tests included in the 28-point NDS was graded from 0-4, with higher scores indicating severe deficits (n=12). Compared using unpaired t-test. FIG. 9D shows the results of brain sections stained with TTC and measured infarct volume (n=8), compared using unpaired t-test. FIG. 9E shows BDNF levels assessed via WB using beta-actin loading control (n=3). Compared using unpaired t-test. For all data, *=p<0.05, =p<0.01, *=p<0.001.

FIG. 10: Table 2, showing sample and crystal data for 31b.

FIG. 11: Table 3, showing data collection and structure refinement for 31b.

FIG. 12: Table 4, showing atomic coordinates and equivalent isotropic atomic displacement parameters ($Å^2$) for 31b.

FIG. 13: Table 5, showing bond lengths (Å) for 31b.

FIG. 14: Table 6, showing bond angles (°) for 31b.

FIG. 15: Table 7, showing anisotropic atomic displacement parameters ($Å^2$) for 31b.

FIG. 16: Table 8, showing hydrogen atomic coordinates and isotropic atomic displacement parameters ($Å^2$) for 31b.

DETAILED DESCRIPTION

Figure 1A:
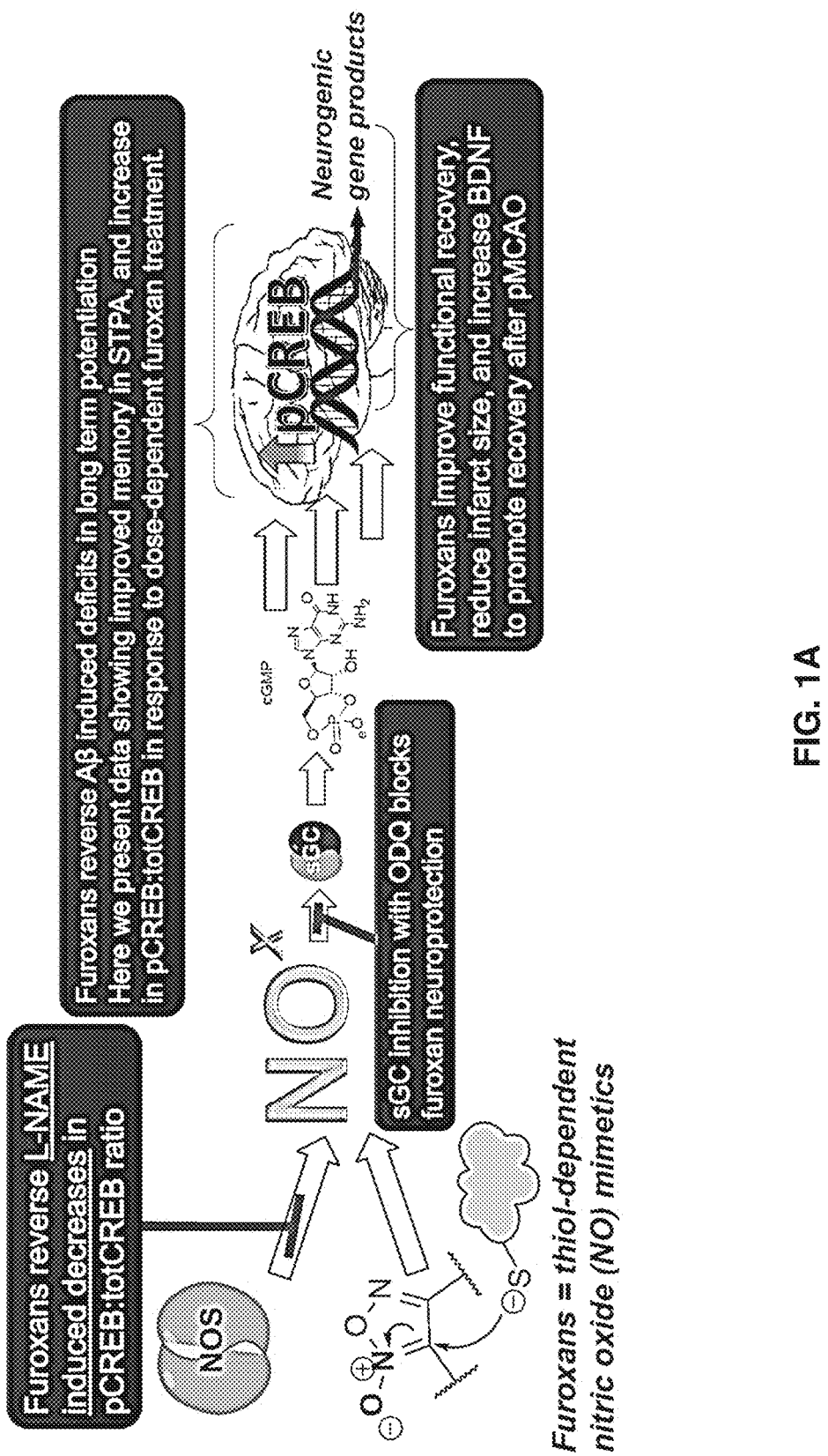
FIG. 1A: Summary of furoxan activity.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, certain terms are defined before further description of the present disclosure.

The term "amino" means —$NH_2$. The term "nitro" means —$NO_2$. The term "halo" designates —F, —Cl, —Br, or —I. The term "mercapto" means —SH. The term "cyano" means —CN. The term "silyl" means —$SiH_3$. The term "trimethylsilyl" means —$Si(CH_3)_3$. The term "hydroxyl" means —OH.

The term "alkyl" refers to a radical, functional group, or substituent derived from an alkane missing one hydrogen. Alkyl groups can be either acyclic alkyl groups having the formula $C_nH_{2n+1}$, where n is any positive integer, or cycloalkyl groups having the formula $C_nH_{2n-1}$, where n is any positive integer. The groups —$CH_3$, —$CH_2CH_3$, —$CH_2CH_2CH_3$, —$CH(CH_3)_2$, —$CH(CH_2)_2$, —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclopentyl, and cyclohexyl, are some non-limiting examples of alkyl groups.

The term "aryl" refers to a radical, functional group, or substitutent derived from an aromatic ring. Non-limiting examples of aryl groups are phenyl, napthyl, thienyl, quinolyl, indolyl, xylyl, and the radical derived from biphenyl. The term "aryl" also includes carbocyclic aryl groups, biaryl groups, and radicals derived from polycyclic fused hydrocarbons.

The term "heteroaryl" refers to a radical, functional group, or substituent derived from a heteroarene group missing one hydrogen. Heteroaryl groups are both heterocyclic (i.e., having one or more atoms other than carbon in at least one ring) and aromatic.

The term "heterocyclic amine" refers to a radical, functional group, or substituent containing at least one heterocyclic ring as well as at least one nitrogen-containing group. For purposes of clarity, the nitrogen-containing group can be part of the heterocyclic ring, or can be attached or the heterocyclic ring. Furthermore, the nitrogen in the nitrogen-containing group can be the heteroatom of the heterocyclic ring. Heterocyclic amines include piperidines, piperazines, thiomorpholines, morpholines, pyrrolidines, and the like.

The term "aralkyl" refers to a radical, functional group, or substituent having an aryl group united with an alkyl group. Non-limiting examples of aralkyls include phenylmethyl (benzyl) and phenylethyl.

The term "alkoxy" refers to a radical, functional group, or substituent having an alkyl group united with oxygen. Non-limiting alkoxy groups include —OCH$_3$, —OCH$_2$CH$_3$, —OCH$_2$CH$_2$CH$_3$, —OCH(CH$_3$)$_2$, and —OCH(CH$_2$)$_2$.

The term "aralkyloxy" refers to a radical, functional group, or substituent having an aryl group united with an alkyl group and with oxygen. Non-limiting aralkyloxy groups include ester-substituted aryl groups, such as methoxy phenyl groups.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

The term "heteroatom-substituted" when used to modify a class of organic radicals (e.g., alkyl, aryl, acyl, etc.), means that one, or more than one, hydrogen atom of that radical has been replaced by a heteroatom, or a heteroatom-containing group. Examples of heteroatoms and heteroatom-containing groups include: hydroxyl, cyano, alkoxy, =O, =S, —NO$_2$, —N(CH$_3$)$_2$, amino, or —SH.

Any of the above-defined functional groups can be substituted with one or more heteroatoms such as N, O, F, Cl, Br, I, Si, P, and S. For example, the following groups are all examples of heteroatom-substituted alkyl groups: trifluoromethyl, —CH—$_2$F, —CH$_2$Cl, —CH$_2$Br, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH(CH$_2$)$_2$, —CH$_2$OCH$_2$CF$_3$, —CH$_2$OCOCH$_3$, —CH$_2$NH$_2$, —CH$_2$NHCH$_3$, —CH$_2$N(CH$_3$)$_2$, —CH$_2$NHCH$_2$CH$_3$, —CH$_2$N(CH$_3$)CH$_2$CH$_3$, —CH$_2$NHCH$_2$CH$_2$CH$_3$, —CH$_2$NHCH(CH$_3$)$_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_2$CH$_2$I, —CH$_2$CH$_2$OH, CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH$_2$CH$_2$NHCH(CH$_2$)$_2$, —CH$_2$CH$_2$N(CH$_2$CH$_3$)$_2$, —CH$_2$CH$_2$NHCO$_2$C(CH$_3$)$_3$, and —CH$_2$Si(CH$_3$)$_3$. The following groups are examples or heteroatom-substituted aryl groups: groups derived from the compounds pyrrole, furan, thiophene, imidazole, oxazole, isoxazole, thiazole, isothiazole, triazole, pyrazole, pyridine, pyrazine, pyridazine, pyrimidine, and the like; —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$OH, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —C$_6$H$_4$CH$_2$CH=CH$_2$, —C$_6$H$_4$CF$_3$, —C$_6$H$_4$CN, —C$_6$H$_4$C≡CSi(CH$_3$)$_3$, —C$_6$H$_4$COH, —C$_6$H$_4$COCH$_3$, —C$_6$H$_4$COCH$_2$CH$_3$, —C$_6$H$_4$COCH$_2$CF$_3$, —C$_6$H$_4$COC$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, and imidazoyl. As another example, —OCH$_2$CF$_3$ is a heteroatom-substituted alkoxy group. Similarly, a heteroatom-substituted aralkyloxy has the structure —OAr, in which Ar is a heteroatom-substituted aralkyl.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Suitable pharmaceutically acceptable salts may also be formed by reacting the compounds of the present disclosure with an organic base such as methylamine, ethylamine, ethanolamine, lysine, ornithine, and the like. Other suitable salts are known to one of ordinary skill in the art.

It should be recognized that the particular anion or cation forming a part of any salt is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their e hods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "effective" means adequate to accomplish a desired, expected, or intended result.

General Description

Provided are furoxans, distinct from known furoxans, that, in some embodiments, are useful in the treatment of various neurological conditions, disorders, or injuries. Described herein is the design and synthesis of furoxans with neuroprotective activity in a cellular model of ischemia. Contrary to known furoxans, the furoxans herein demonstrate brain bioavailability, in vivo cognition enhancement (memory improvement), and in vivo neurorestorative effects in a model of stroke. In sum, the furoxans herein possess biological activity which provide efficacy in multiple neurodegenerative disorders, including Alzheimer's disease, stroke, traumatic brain injury (TBI), and chronic traumatic encephalopathy (CTE).

The furoxans herein are of the general structure of Formula I, shown as follows with the ring positions numbered:

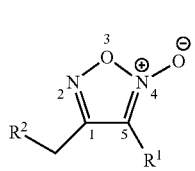

Formula I where $R^1$ is a substituted or unsubstituted aryl, heteroaryl, aralkyl, alkoxy, or aralkyloxy group, and $R^2$ is a substituted or unsubstituted heterocyclic amine. Non-limiting example $R^1$ and $R^2$ groups include those shown in Table 1 (FIG. 2B). $R^1$ can be, for example, a halogen-substituted aryl, a halogen-substituted aralkyl, an unsubstituted alkoxy, or an unsubstituted aryl. Non-limiting examples of $R^1$ include phenyl, 4-fluorophenyl, 4-bromophenyl, 4-clorophenyl, 4-tetrafluoromethylphenyl, 4-difluoromethoxyphenyl, 4-nitrophenyl, 4-tetrafluoromethyoxyphenyl, and 4-methylphenyl. $R^2$ can be, for example, an unsubstituted heterocyclic amine, a deuterium-substituted heterocyclic amine, or an alkyl-substituted heterocyclic amine. Any salt of Formula I, including but not limited to those defined above as examples of suitable pharmaceutically acceptable salts, is encompassed herein.

One non-limiting example compound of Formula I is compound 31b, which has the following structure:

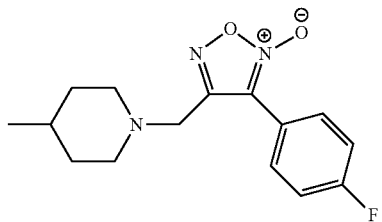

31b

Another non-limiting example compound of Formula I is compound 32b, which has the following structure:

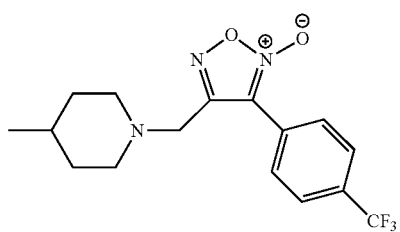

32b

Another non-limiting example compound of Formula I is compound 33b, which has the following structure:

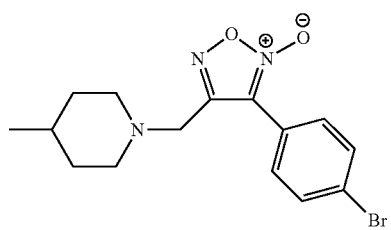

33b

Another non-limiting example compound of Formula I is compound 34b, which has the following structure:

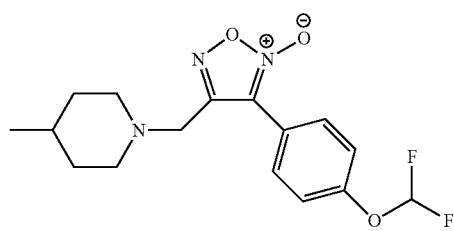

34b

Another non-limiting example compound of Formula I is compound 35b, which has the following structure:

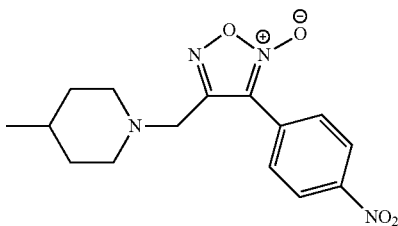

35b

Another non-limiting example compound of Formula I is compound 36b, which has the following structure:

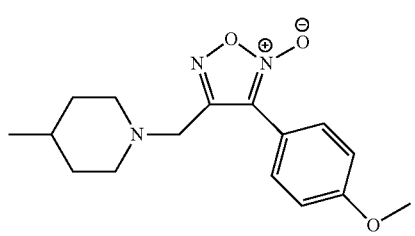

36b

Another non-limiting example compound of Formula I is compound 37b, which has the following structure:

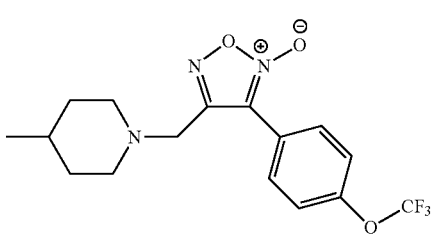

37b

Another non-limiting example compound of Formula I is compound 38b, which has the following structure:

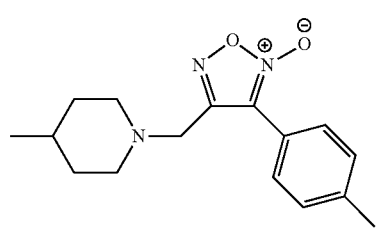

38b

Another non-limiting example compound of Formula I is compound 39b, which has the following structure:

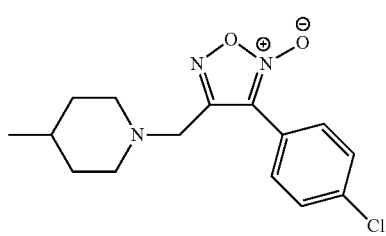

39b

Another non-limiting example compound of Formula I is compound 40b, which has the following structure:

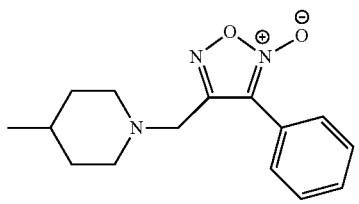

40b

Another non-limiting example compound of Formula I is compound 41b, which has the following structure:

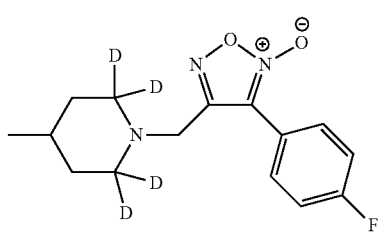

41b

As one example, compound 31b provides concentration dependent protection against oxygen glucose deprivation (OGD), reverses the effects of NOS inhibition on pCREB, reverses scopolamine induced memory impairment in step through passive avoidance (STPA), reverses neurologic deficit, and improves rotarod performance. In addition, compound 31b provides significant brain penetration.

Without wishing to be bound by theory, it is believed that favorable CNS penetration results from a series of inter-related properties, including: 1) balanced membrane permeability and solubility, 2) low propensity for efflux by Pglycoproteins (Pgp), and 3) adequate brain tissue partitioning to provide a sufficient level of unbound drug at the site of action. Behavior with regard to these properties is highly-dependent upon the intrinsic characteristics of the molecule being studied (i.e., molecular weight [MW], partition coefficient [c log P], and total polar surface area [tPSA]). Hence, developing molecules with appropriate physiochemical properties is important in CNS drug design. The furoxans described herein follow the design criteria of MW<450 g/mol, C log P 2.0-5.0, and tPSA 40-90. For comparison, these properties are highlighted for the known compounds in PRIOR ART FIG. 1B (red=property outside of the criteria, green=appropriate property).

Figure 2A:
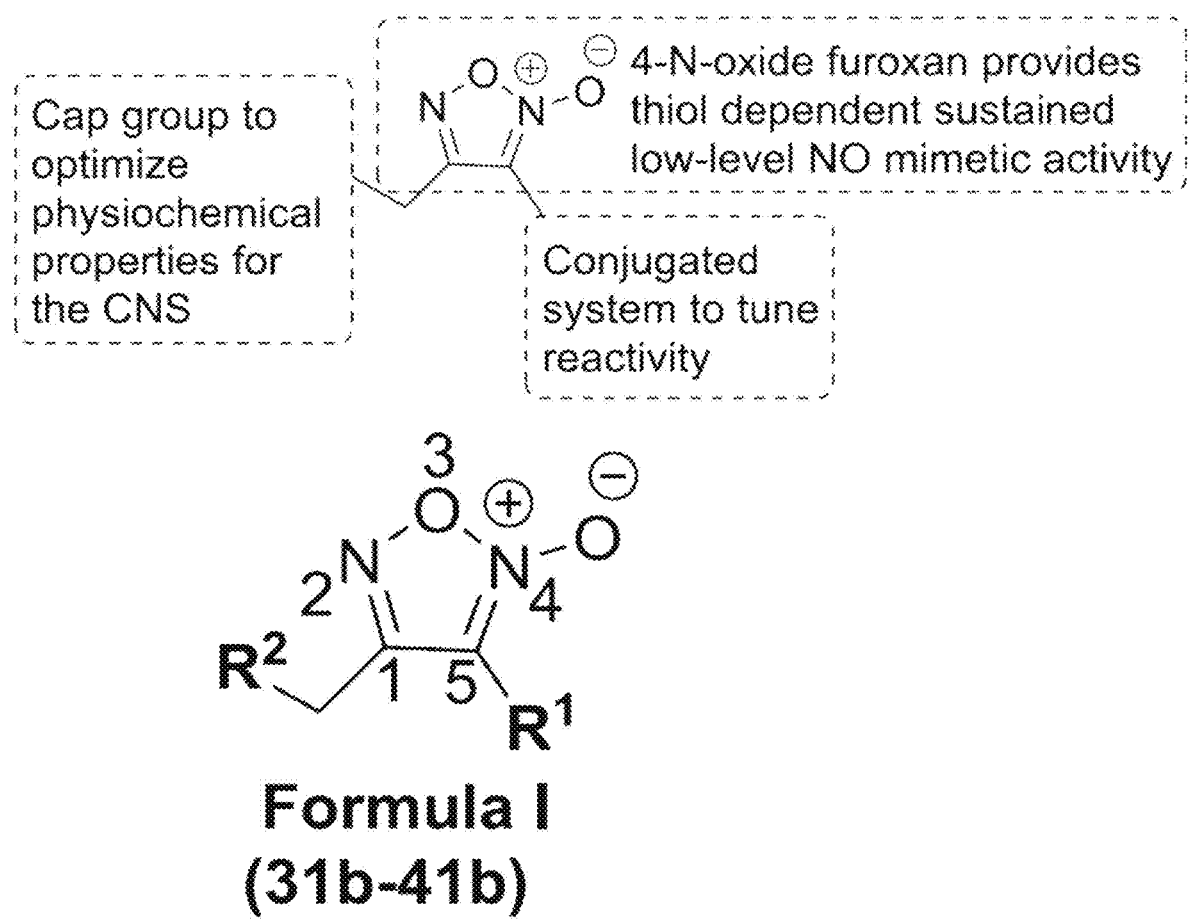
FIG. 2A: Structural information regarding Formula I.

The design motif of these agents is shown in FIG. 2. The unique molecular structure of furoxans allows for 'tunable' NO mimetic activity via modification at the conjugated C5 position (defined in Formula I shown in FIG. 2A), designated substituent $R^1$. A cap group, denoted as $R^2$, is used to impart appropriate physiochemical properties to provide sufficient access to the CNS. The compounds disclosed herein maintain a 4-N-oxide furoxan ring substituted with an aryl or heteroaryl system on the carbon adjacent to the N-oxide and a —$CH_2$— group opposite of the aryl system (Formula I). For simplicity at this point, Formula I provides a proper description of the requisite scaffold. According to Formula I, C1 is linked to the cap group, denoted as $R^2$, via a $CH_2$ group, and $R^1$ can be a variety of aryl or heteroaryl systems as long as the physicochemical properties of the complete structure obey the CNS design criteria. Specific embodiments may include, but are not limited to, the structures shown in Table 1 (FIG. 2B), the general synthetic scheme for which is given at the top of Table 1 (FIG. 2B).

The preparation of selected embodiments of Formula I is outlined in Table 1 and begins with the reduction of the commercially available cinnamic acids to the corresponding cinnamyl alcohols (1-10). The furoxan ring is prepared by treating the cinnamyl alcohols in acetic acid with sodium nitrite to yield the furoxan alcohols (11-20). Activation of the alcohol via triphenyl phosphine and carbon tetrabromide followed by substitution with an appropriate cap group electrophile provides the 2-N-oxide furoxans (31a-41a). The 2-N oxides are stirred in boiling toluene for 7 days, or irradiated with μ-waves while stirring in toluene for 1 hr, to yield the corresponding 4-N oxide furoxan final compounds (31b-41b). In these embodiments, 4-methylpiperidine or an isotope labeled 4-methylpiperidine-2,2,6,6-$d^4$ may be used as a cap group to provide final compounds which obey the design criteria described above. The presence of the tertiary nitrogen in these analogs allows for the preparation of pharmaceutically useful salts, as was carried out for 31b (scheme in Table 1, at top of FIG. 2B). The examples herein further describe the synthesis and characterization of these compounds.

Pharmaceutical compositions of the present disclosure comprise an effective amount of a compound of Formula I (an "active" compound), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating various neurodegenerative disorders and conditions such as, but not limited to: Alzheimer's disease, stroke, traumatic brain injury (TBI), and chronic traumatic encephalopathy (CTE). Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

It is further envisioned that the compounds and methods described herein can be embodied in the form of a kit or kits. A non-limiting example of such a kit is a kit for making a furoxan compound, the kit comprising cinnamic acid and one or more of reducing agent, acetic acid, sodium nitrite, triphenyl phosphine, carbon tetrabromide, toluene, and an aryl or heteroaryl electrophile in separate containers, where the containers may or may not be present in a combined configuration. Many other kits are possible, such as kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Embodiments of the present disclosure further include methods of determining coverage or denial of health insurance reimbursement and/or payment for treatments of disease comprising the compounds or compositions described herein. In certain embodiments, the treatment comprises a compound of Formula I, or a pharmaceutical composition containing a compound of Formula I, and a provider of health insurance denies coverage or reimbursement for the treatment.

EXAMPLES

In Vitro Neuroprotection

Figure 3A:
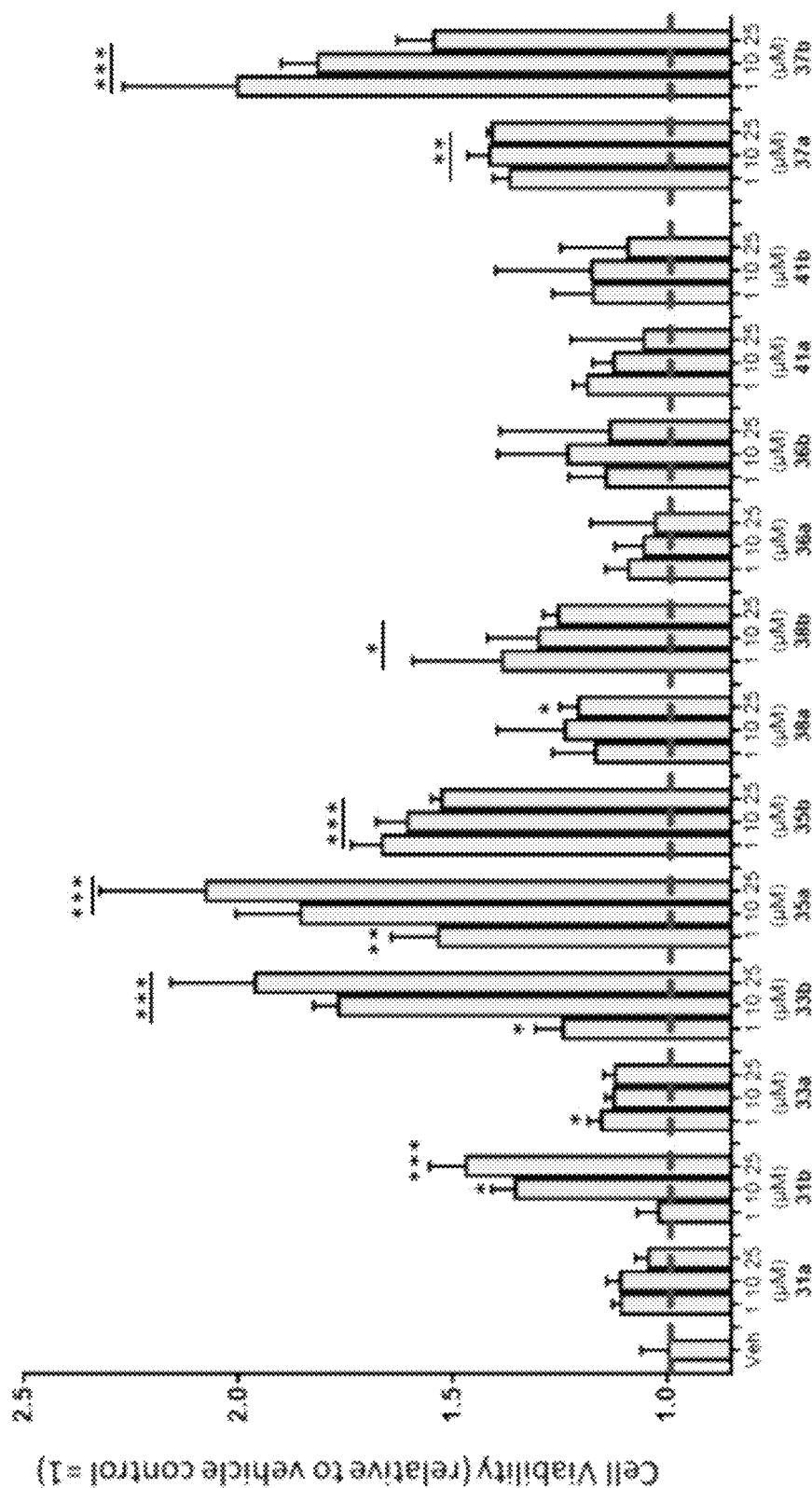
FIGS. 3A-3C: Neuroprotection (FIG. 3A), MTT treatment was used to assess cell viability (FIG. 3B), and pCREB modulation (FIG. 3C) of furoxan compounds. Neuroprotection assay workflow: expose PC12 cells to oxygen glucose deprivation (OGD) for 90 min→reoxygenate and add furoxan (1, 10, or 25 µM)→incubate for 24 hr→MTT readout of viability. Data represented as mean and s.e.m. (n=3). *=p<0.05, =p<0.01, *=p<0.001 compared to vehicle control using one way ANOVA analysis with Dunnett's post-hoc test. Red dashed line indicates threshold of vehicle effects. For pCREB modulation, 31b (25 µM) was examined (PC-12 cells, 48 hr incubation) in the following: without insult, with OGD, L-NAME.
Figure 3B:
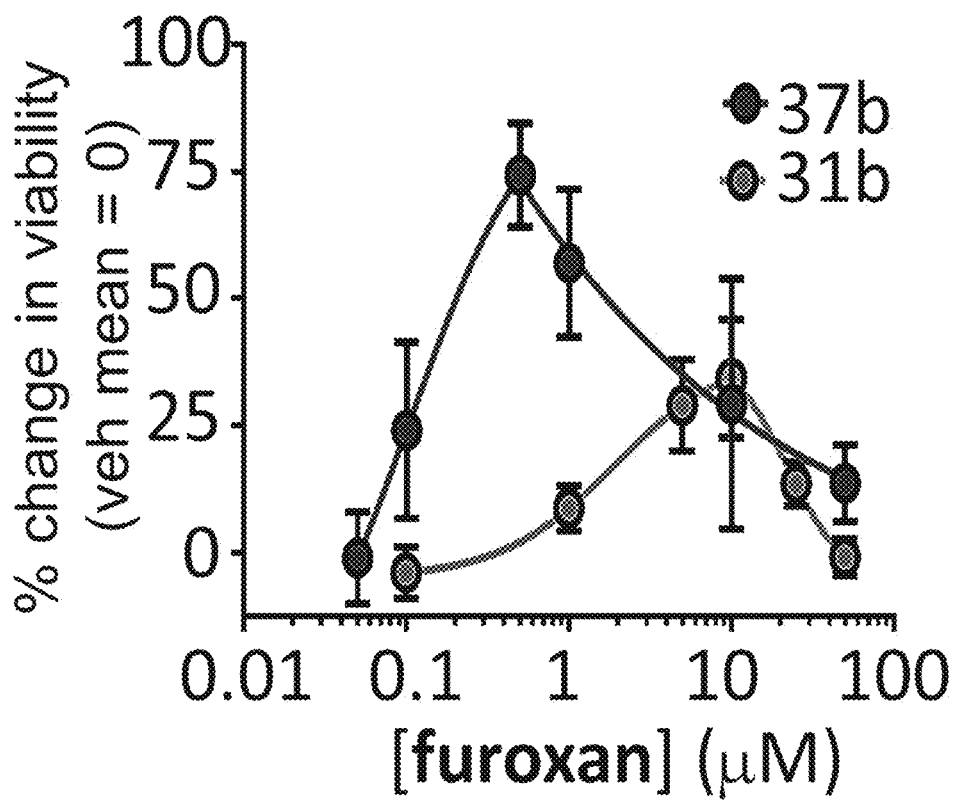
Figure 3C:
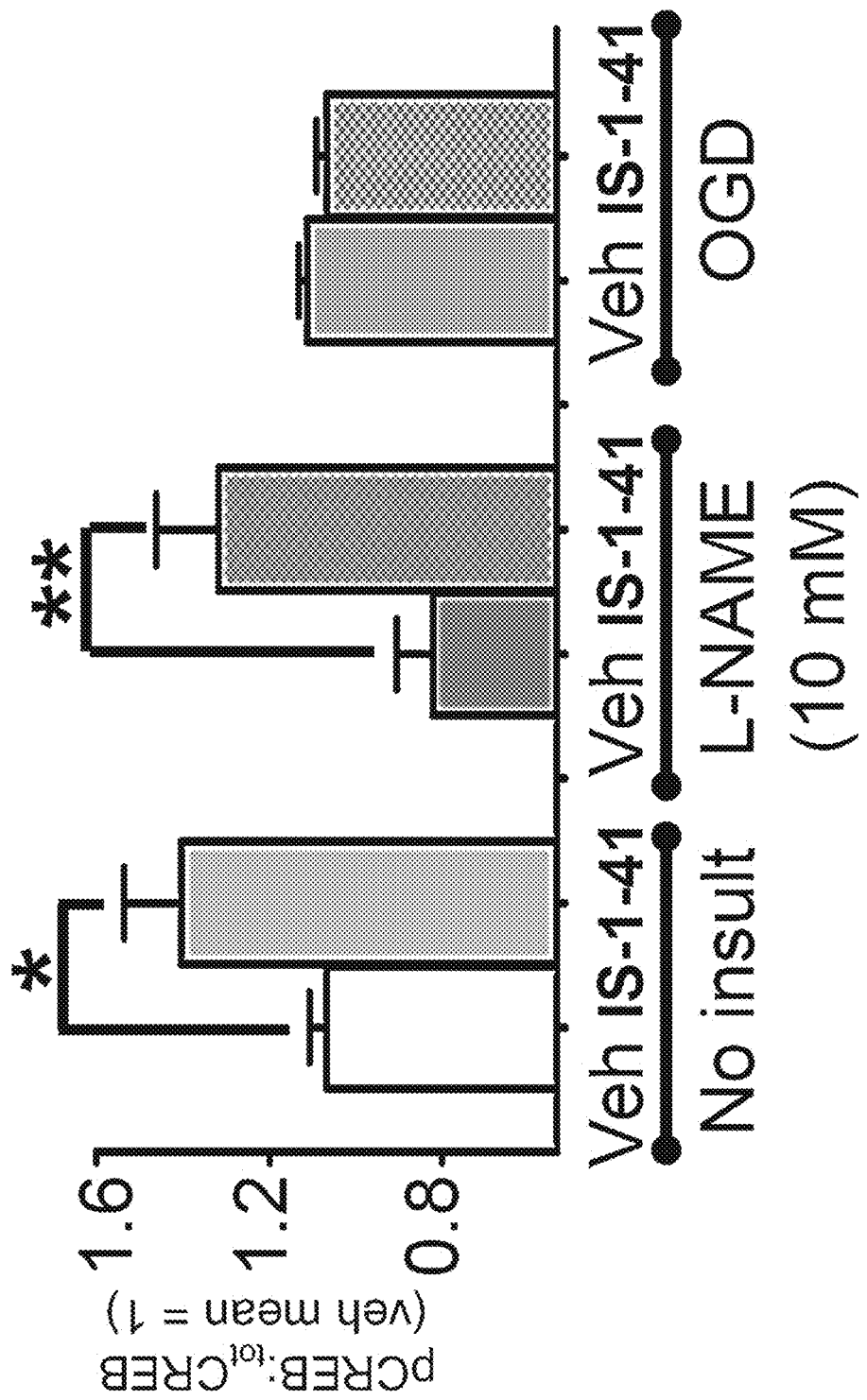

It has been shown that furoxans are protective against oxygen glucose deprivation (OGD), a commonly used cellular model of ischemic stroke. PC12 cells were submitted to OGD for 90 minutes followed by reoxygenation and treatment with varying concentrations of selected embodiments of compounds of Formula I (indicated in FIG. 3A). After 24 hr, MTT treatment was used to assess cell viability (FIG. 3B). Robust activity was observed for several analogs relative to the vehicle treated control (FIG. 3C). It has been shown previously that 4-N-oxides release NO at a much slower rate than corresponding 2-N-oxides. As can be seen in FIG. 2, in most instances the 4-N-oxides (31b, 33b, 38b, 36b, 41b, and 37b) outperform the corresponding 2-N-oxides (31a, 33a, 38a, 36a, 41a, and 37a). This indicates that slow NO release is beneficial and neuroprotective compared to fast NO release. Based on these results, 31b was chosen for in vivo evaluations.

In Vivo Activity in a Model of Cognitive Function

Figure 4A:
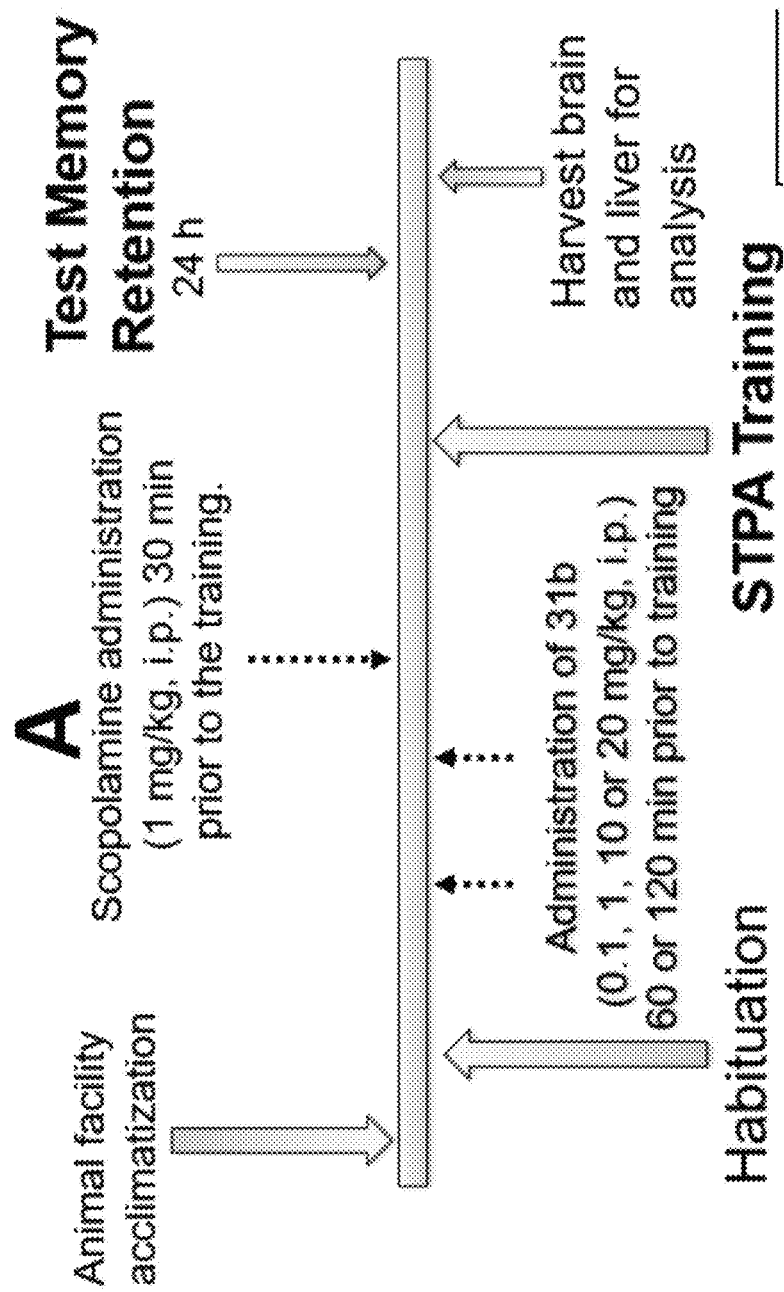
FIGS. 4A-4B: STPA experimental timeline (FIG. 4A), and results of Male C57BL/6 mice administered either vehicle or 31b via i.p. injection at 60 min or 120 min prior to training in STPA (FIG. 4B). Scopolamine (1 mg/kg) was administered 30 min prior to training. Memory retention was measured as latency to enter the dark compartment 24 h after training. Data represented as mean and s.e.m. (n=7-9). =p<0.01, *=p<0.001 compared to negative scopolamine treated control using one way ANOVA analysis with Dunnett's post-hoc test.

Step-through passive avoidance (STPA) assesses the ability of drugs to reverse hippocampal dependent aversive memory deficits induced by scopolamine (1 mg/kg, i.p.). Reversal of scopolamine-induced amnesia is not a sophisticated model, but it is well understood and remains a useful model for screening of drugs for procognitive actions. This paradigm allows for evaluation of furoxan neuromodulatory activity in vivo in an identical context to that previously used to demonstrate NO mimetic nitrate efficacy. The STPA apparatus consisted of an acrylic box with an illuminated compartment connected to a darkened compartment by a small guillotine door. Mice were placed in the illuminated side and were trained against their natural tendency to translocate to the dark side using an aversive stimulus (shock via electrified floor grading). Memory consolidation is measured as the latency times to enter the dark compartment 24 hr after training. FIG. 4A illustrates the STPA treatment timeline and results. Scopolamine treated mice showed significantly less latency to enter the dark compartment compared to wild-type mice (Scopolamine treated: 63.5 s±30 s versus vehicle treated: 270 s±30 s). 31b was capable of reversing scopolamine induced amnesia, with the most favorable outcome occurring when administered 2 hr prior to training at 20 mg/kg (latency=237 s±20 s). This behavioral data demonstrates that furoxans can be designed to possess neuromodulatory activity in vivo in a dose-dependent and time dependent manner. Additionally, improved activity at the longer 120 min time point may support the "attenuated" NO mimetic nature of the tested furoxans. This foundational data represents the first in vivo record of furoxans having abilities for treating dementia and neurodegenerative diseases. These results indicate that furoxans can cross the blood brain barrier and possess sufficient metabolic stability to provide neuromodulatory efficacy.

In Vitro Reactivity and Metabolism Studies

Figure 5A:
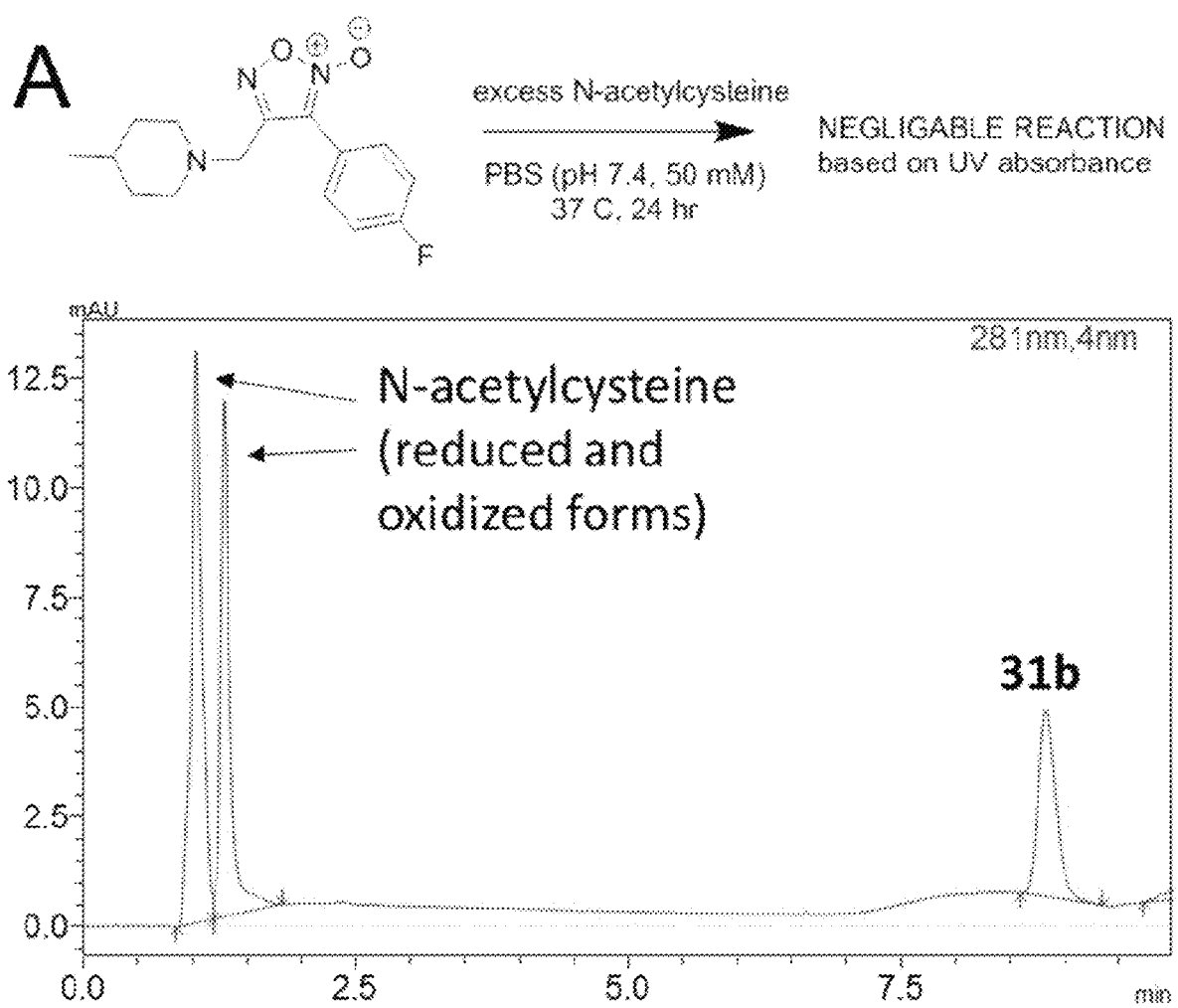
FIGS. 5A-5B: Thiol reactivity was analyzed via incubations containing 31b (250 µM) in the presence or absence of excess (5 mM) cysteine (or N-acetylcysteine [NAc]) in PBS (50 mM, pH 7.4) at 37° C.

Without wishing to be bound by theory, it is believed that furoxans require thiol attack to produce NO. High concentrations of thiols are ubiquitous in all cells, with the most abundant biological thiols being glutathione (GSH) and cysteine. Understanding the reactivity and metabolic stability of furoxans is important to demonstrate drug-likeness and development potential. In the examples herein, the ability to modulate reactivity of the furoxans by manipulating the electronic properties of the furoxan ring system is demonstrated. Thiol reactivity of 31b was assessed via incubations with excess thiol (N-acetylcysteine [NAc]) at physiological pH and temperature using a temperature controlled HPLC autosampler. Previously in this paradigm, furoxan half-life's ($t_{1/2}$) ranging from 15 min to >12 hr (depending on furoxan substitution) were observed. Here, 31b was observed to be significantly unreactive, with no measurable change in amount of 31b after 24 hr (FIG. 5A, UV-vis chromatogram). It is important to note that 31b has demonstrated NO/cGMP dependent efficacy in multiple in vitro and in vivo neurodegeneration models. Taken together, these observations indicate that bioactivation to produce NO under cellular conditions requires relatively reactive thiol species.

Metabolic stability is an important parameter for determining the drug-like properties of a molecule, especially when trying to develop attenuated furoxans which require reaction with thiols to produce an effect. The metabolism of 31b in the presence of rat liver microsomes (RLM) was studied. Verapamil and warfarin were used as well-characterized controls. 31b was found to have a RLM $t_{1/2}$ of approximately 11 min. This is significantly shorter than anticipated, with the knowledge that 31b is able to reverse scopolamine induced aversive memory deficits in vivo when administered 2 hr prior to step-through passive avoidance training (STPA). 31b is extremely stable in the presence of general cellular thiols, such as GSH and cysteine. Therefore, phase 1 heme-dependent oxidoreductase activity of CYP enzymes is believed to be primarily responsible for this short $t_{1/2}$.

Figure 4B:
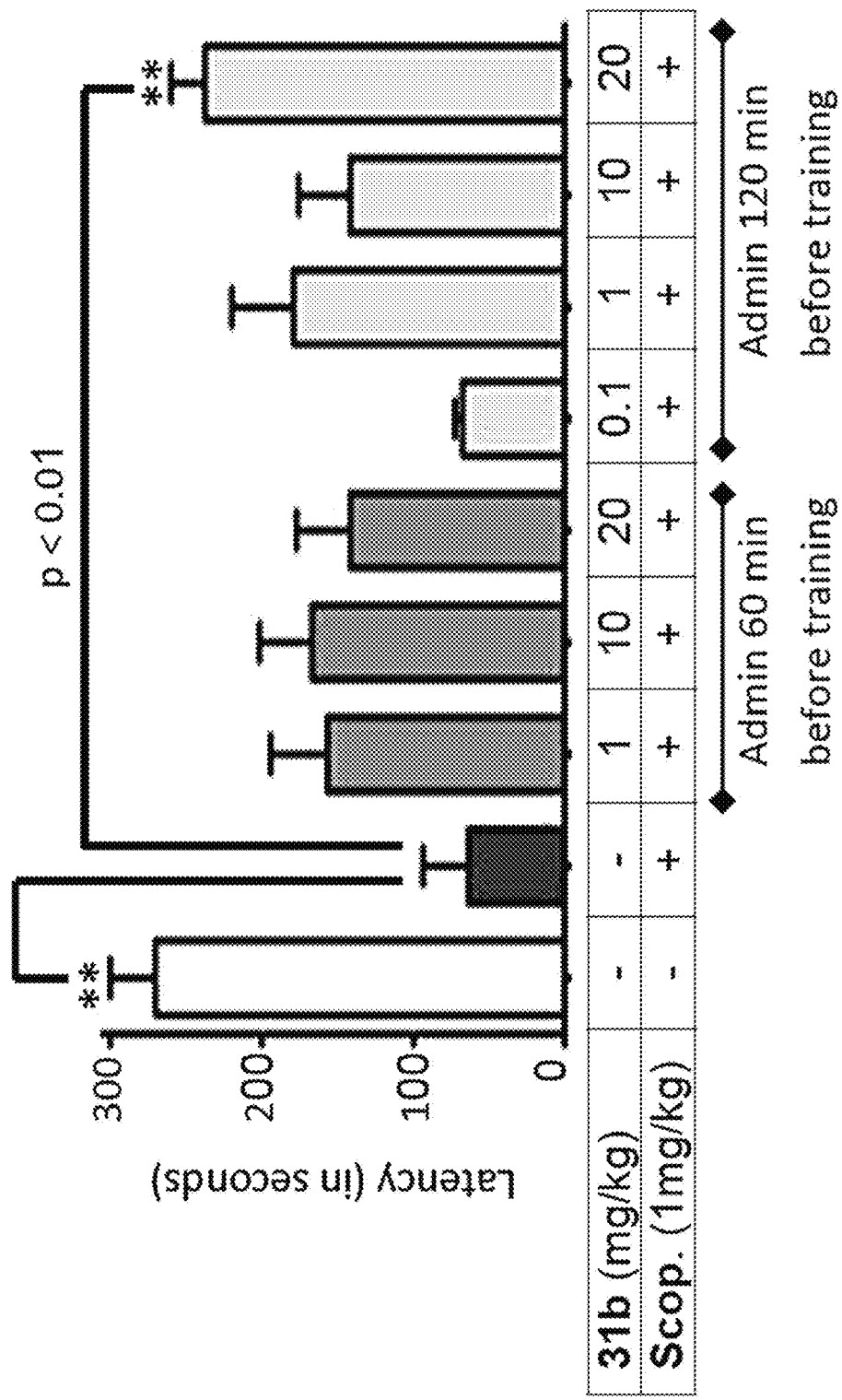
Figure 5B:
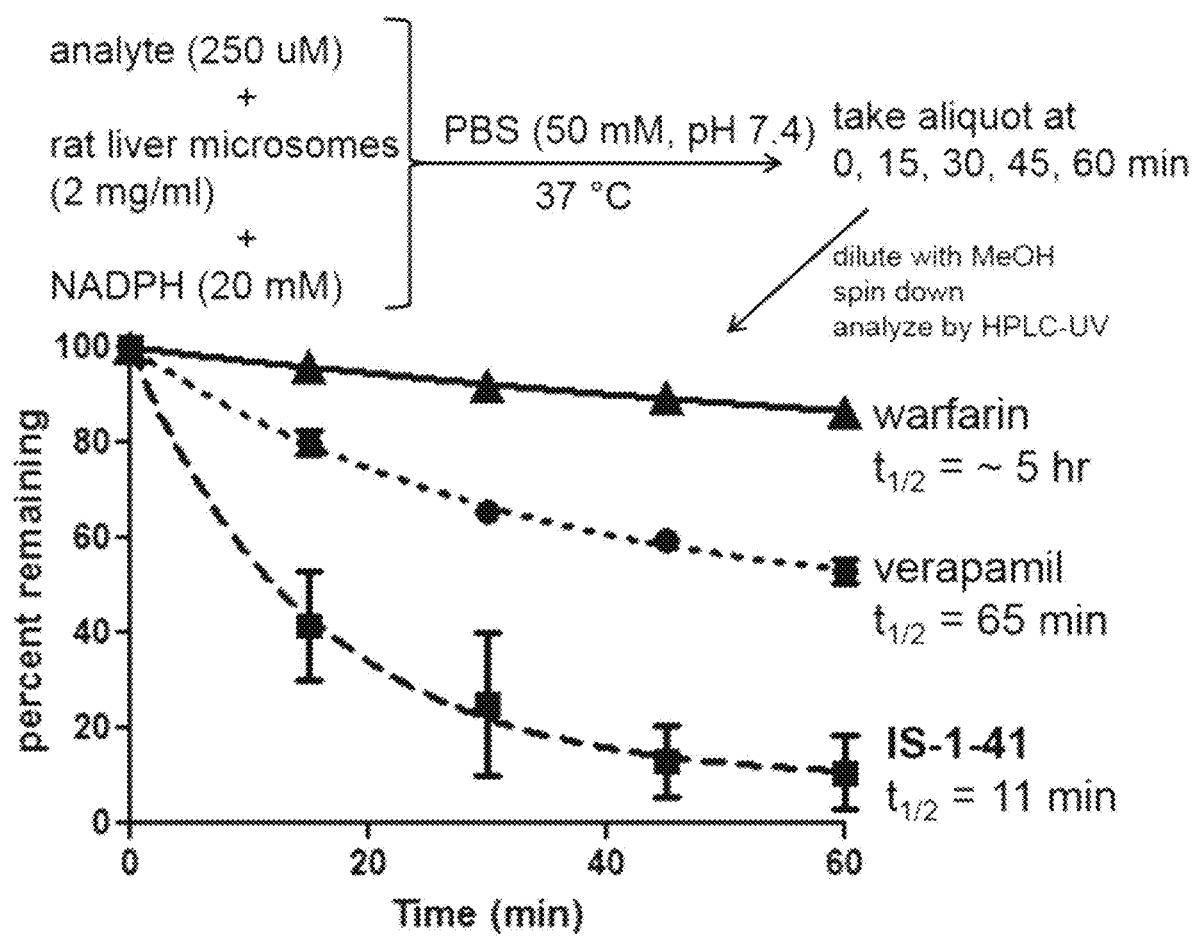

In Vivo Pharmacokinetic Studies 31b was administered to mice and specimens were processed according to FIG. 4A. Levels of 31b were determined in the plasma and forebrain after intraperitoneal (ip) and oral (po) administration at varying post-administration time points (1, 2, or 12 hr [N=4 per cohort]). Selected sacrifice times were intended to define the in vivo metabolic stability of 31b while also mimicking previous behavioral studies in which 31b (20 mg/kg) reversed scopolamine induced memory deficits when administered 2 hr prior to behavioral training. A deuterated (d⁴) analog of 31b, designated 41b, was synthesized for LC-MS studies. Deuterated internal standards are required for absolute quantitation via LC-MS/MS and are desirable for because they have identical physiochemical properties to their non-deuterated kin, but may be distinguished based on molecular weight. Inclusion of 41b allows for control of extraction efficiency, technique proficiency, and instrumentation sensitivity. Extraction methodology and tandem LC-MS/MS parameters (optimized MRM transitions) were developed and validated via extraction of blank brain tissue spiked with 31b and 41b to develop a calibration curve. In this initial evaluation, the appropriate forebrain and plasma samples were spiked with a fixed concentration of 41b, homogenized in extraction buffer, applied to a solid phase resin cartridge, eluted, concentrated, reconstituted, and analyzed via MRM monitoring using LC-MS/MS. 31b was observed in all drug-treated animals, including detectable levels after 12 h (FIG. 4B). In vivo $t_{1/2}$ for brain and plasma measurements are shown in FIG. 5. In each instance, the $t_{1/2}$ appears to be between 50 min-110 min. There were no significant differences in levels of 31b in the brain (B) versus plasma (P), with an average B:P ratio of 1.6 (±0.8). Noticeably, the drug was found in significantly higher amounts in ip-treated mice compared to those administered via oral gavage. Without wishing to be bound by theory, it is believed that low oral bioavailability of 31b is the result of rapid 1st pass metabolism, since the microsomal stability studies indicate poor hepatic stability. The use of common dosage form strategies likely results in improved oral bioavailability. Alternative administration routes, including intranasal, are also believed to result in high brain bioavailability based on the relativity high lipophilicity of the embodiments tested. This demonstration of a furoxan crossing the blood brain barrier is significant. Moreover, the physiochemical properties proposed as being appropriate for CNS drugs are appropriate. The long residence time of the furoxan (visible in the brain after 12 hr), indicates an ideal scenario for daily dosing.

In Vivo Pharmacodynamic Effects

Figure 6A:
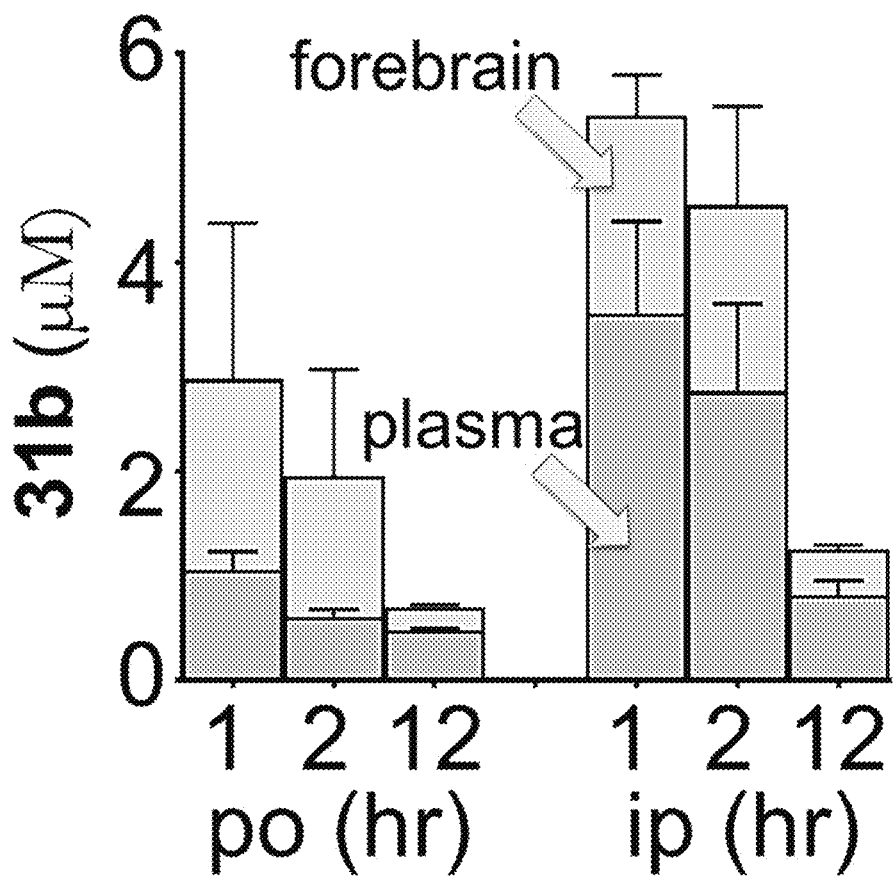
FIGS. 6A-6C: The ratio of the AUC of the MRM transition for 31b versus 41b was calculated and the resulting values were normalized based on total protein concentration of samples (determined by Bradford assay). N=4 per group. Data shown as SEM, analysis by one way ANOVA with Tukey's post-test. *=p<0.05. Half-life's were calculated based on first order exponential decay.
Figure 6B:
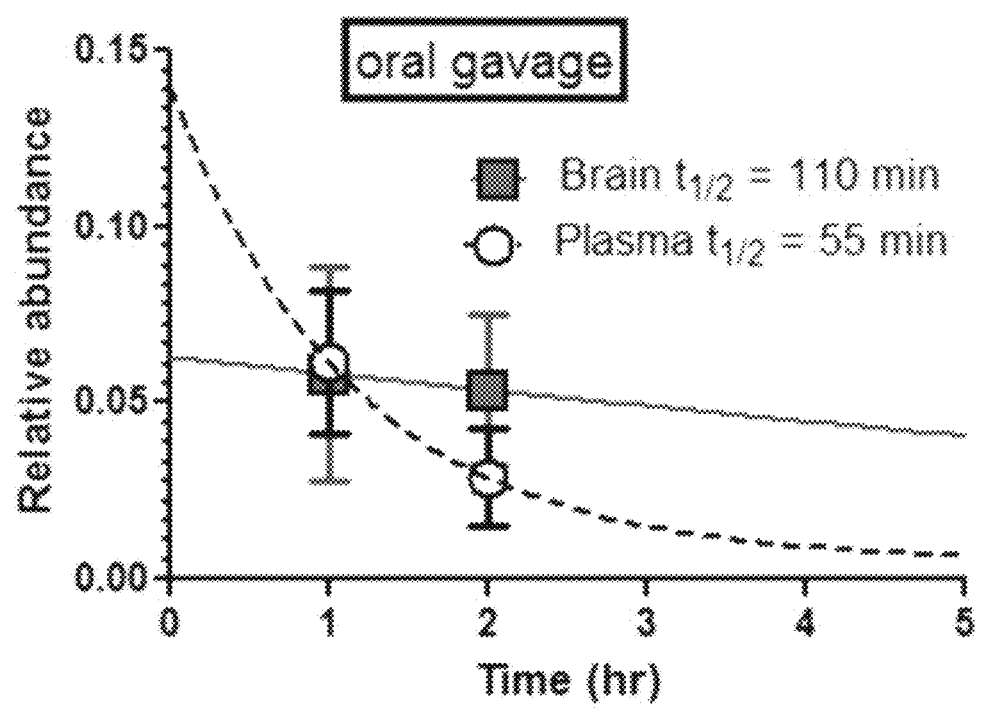
Figure 6C:
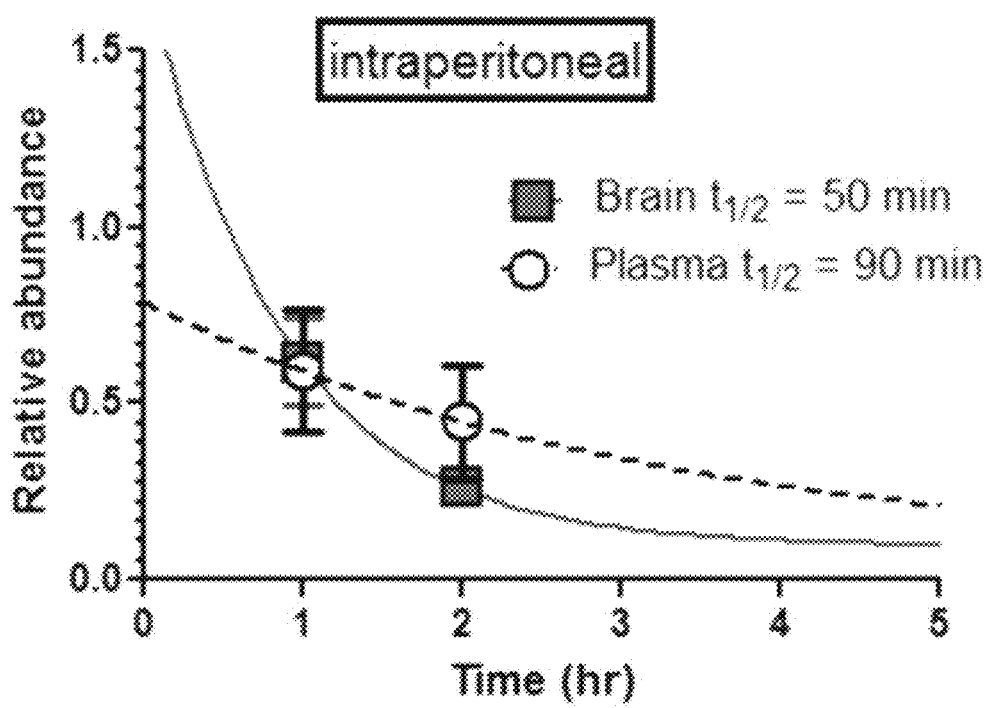
Figure 7:
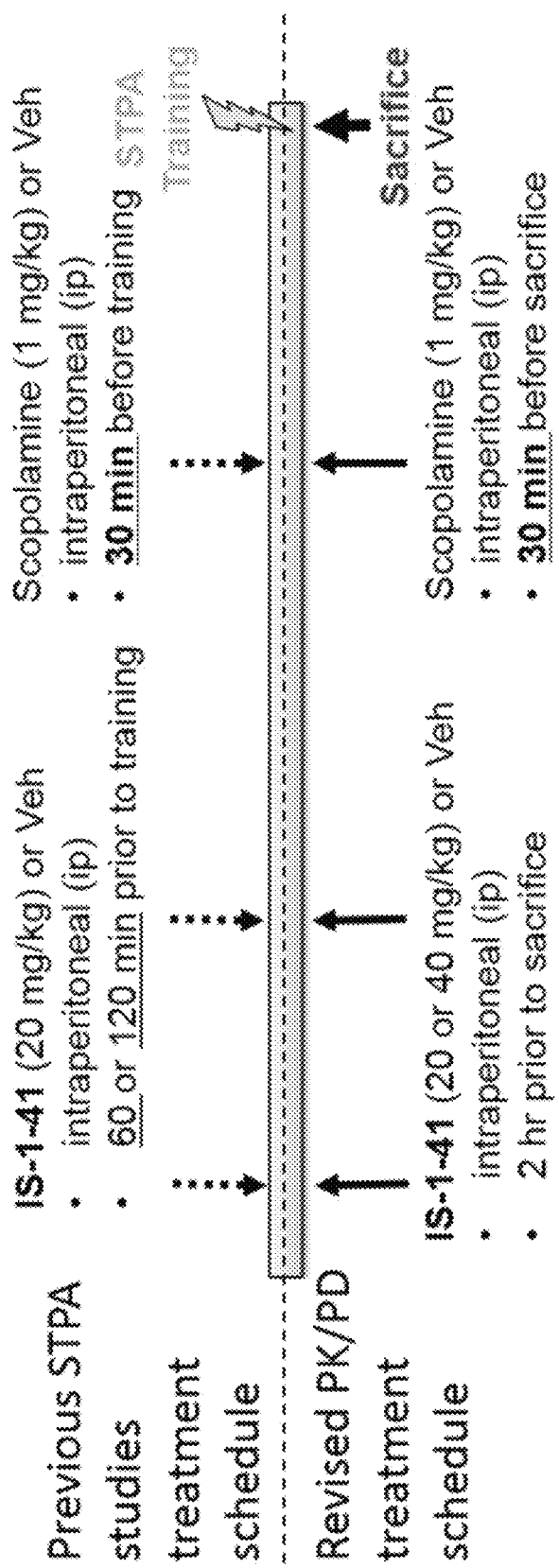
FIG. 7: PD study overview (compared to STPA study).

Without wishing to be bound by theory, it is believed that transcriptional activation of CREB (via phosphorylation) is required for memory consolidation. Phosphorylation of CREB's chief regulatory site (Ser-133) is required for function. Therefore, CREB phosphorylation at Ser-133 was focused on. Note: pCREB must be measured relative to total CREB (tCREB) in the system of interest. The hippocampus specifically, which is the chief brain region responsible for learning and memory, was focused on. Hippocampal homogenates from the cohorts in FIGS. 6A-6C were normalized by Bradford assay and pCREB:tCREB analyzed by ELISA. The recorded pCREB:tCREB ratios are given in FIG. 5. In these experiments, a cholinergic insult was induced in an identical fashion to the STPA studies (using scopolamine), which should lower pCREB levels compared to the vehicle and allow for reversal by 31b to be measured. A second dose quantity of 31b (40 mg/kg) was examined. Based on low hepatic stability in the PK study, only ip administration was performed in these experiments. A marked decrease in the hippocampal pCREB:tCREB ratio in scopolamine treated mice was observed, which trends toward reversal by 31b (FIGS. 6A-6C). The inherent variability in the mice pCREB and tCREB levels was greater than expected when calculating the sample size. It was attempted to set the cohort size (N=4) to be appropriate for both PK and PD studies. Indeed, based on the cumulative evidence, an N of 7-8 per cohort strengthens statistical significance.

Figure 8A:
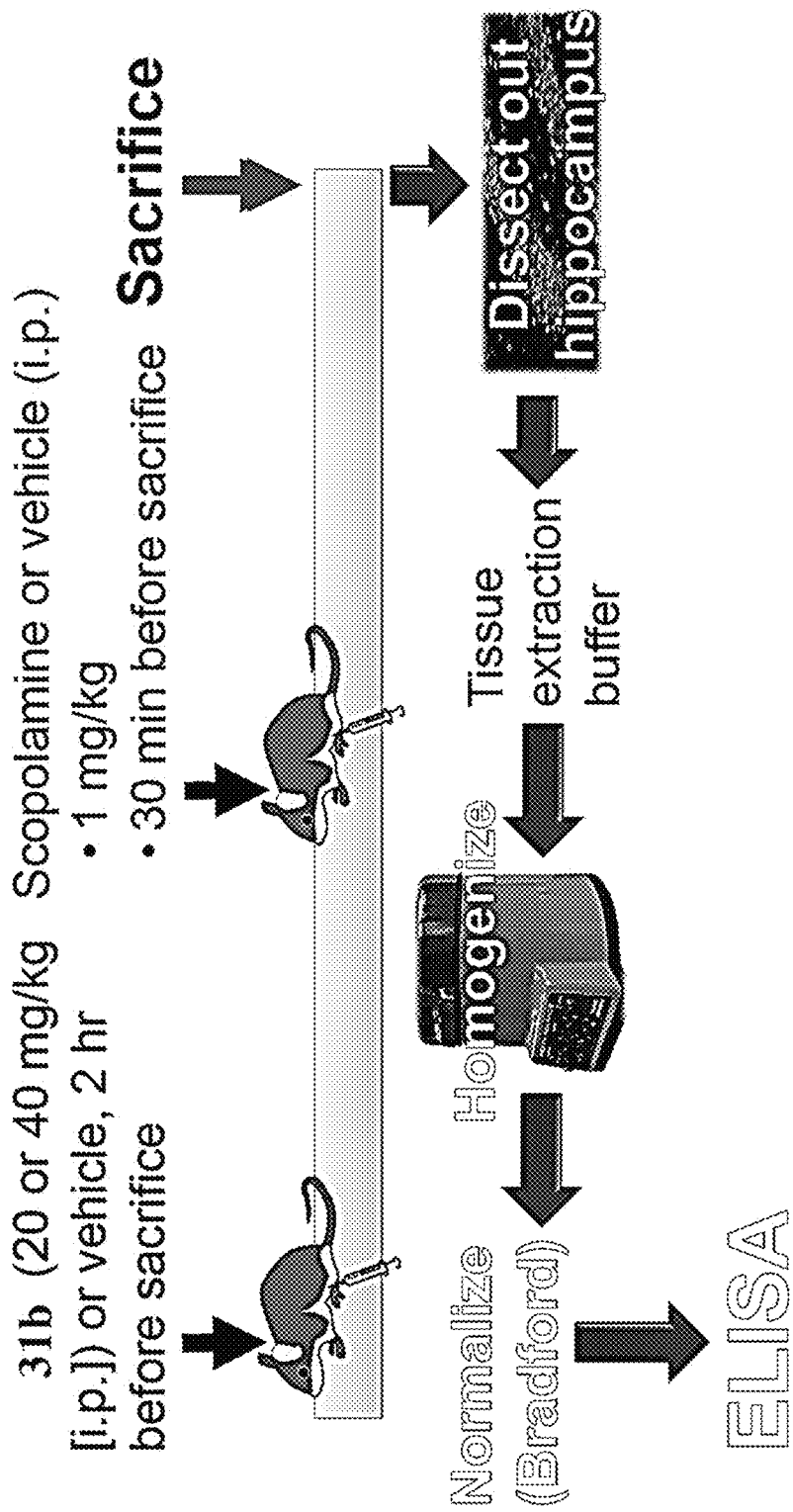
FIGS. 8A-8B: Dissected out hippocampus was homogenized according to procedure used for forebrain processing described above. Resulting homogenate was analyzed by ELISA. Resulting values were and pCREB:tCREB calculated. N=4 per group for Veh and 40 mg/kg cohorts. N=6 for scopolamine and 20 mg/kg. Data shown as SEM, analysis by one way ANOVA with Tukey's post-test. *=p<0.05.
Figure 8B:
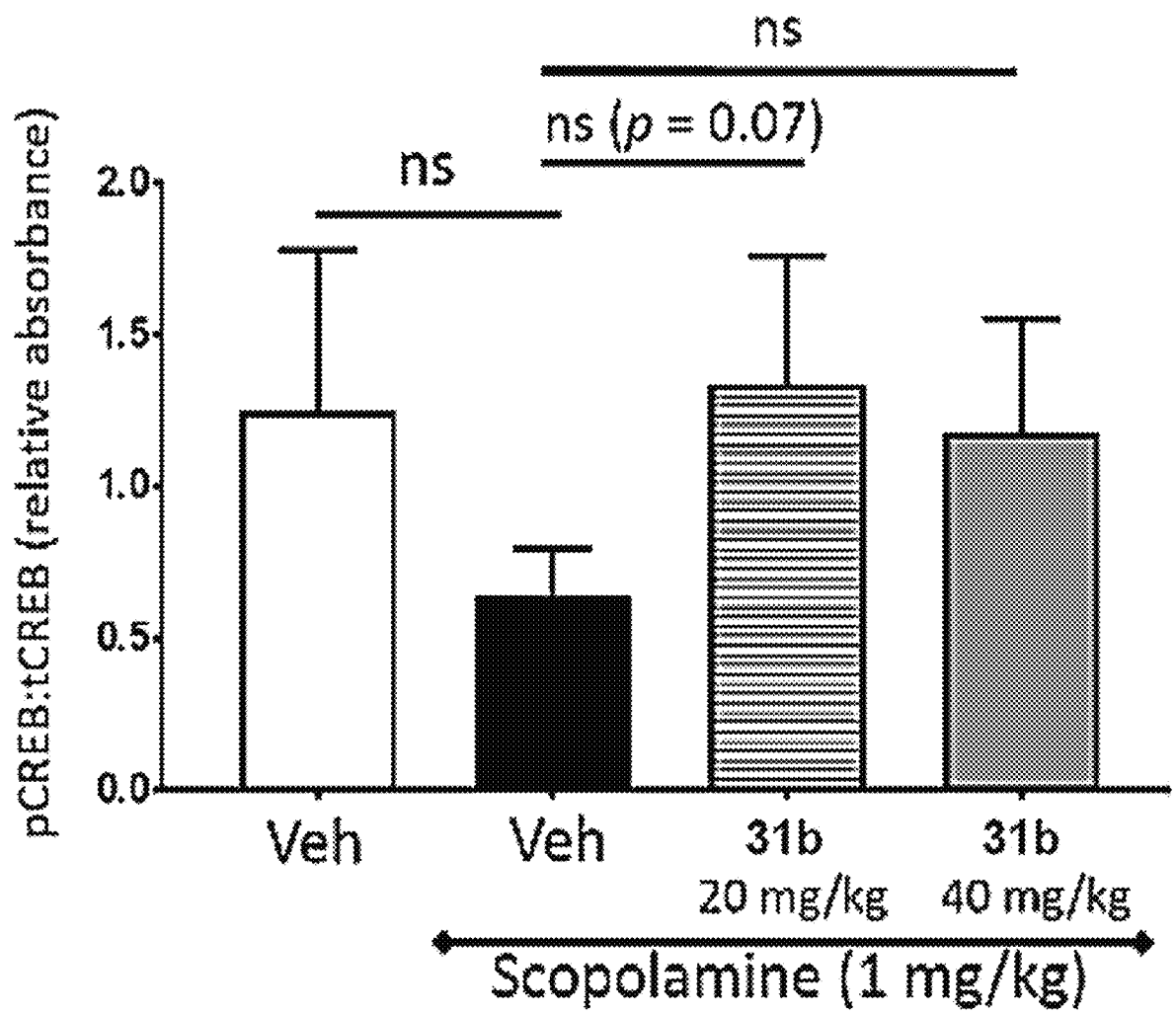

Hippocampal homogenate was analyzed by ELISA and resulting values were used to calculate $_{Ser133}$pCREB:$_{total}$CREB. FIG. 8A shows the treatment timeline for this experiment. FIG. 8B shows the results of this experiment.

Figure 9A:
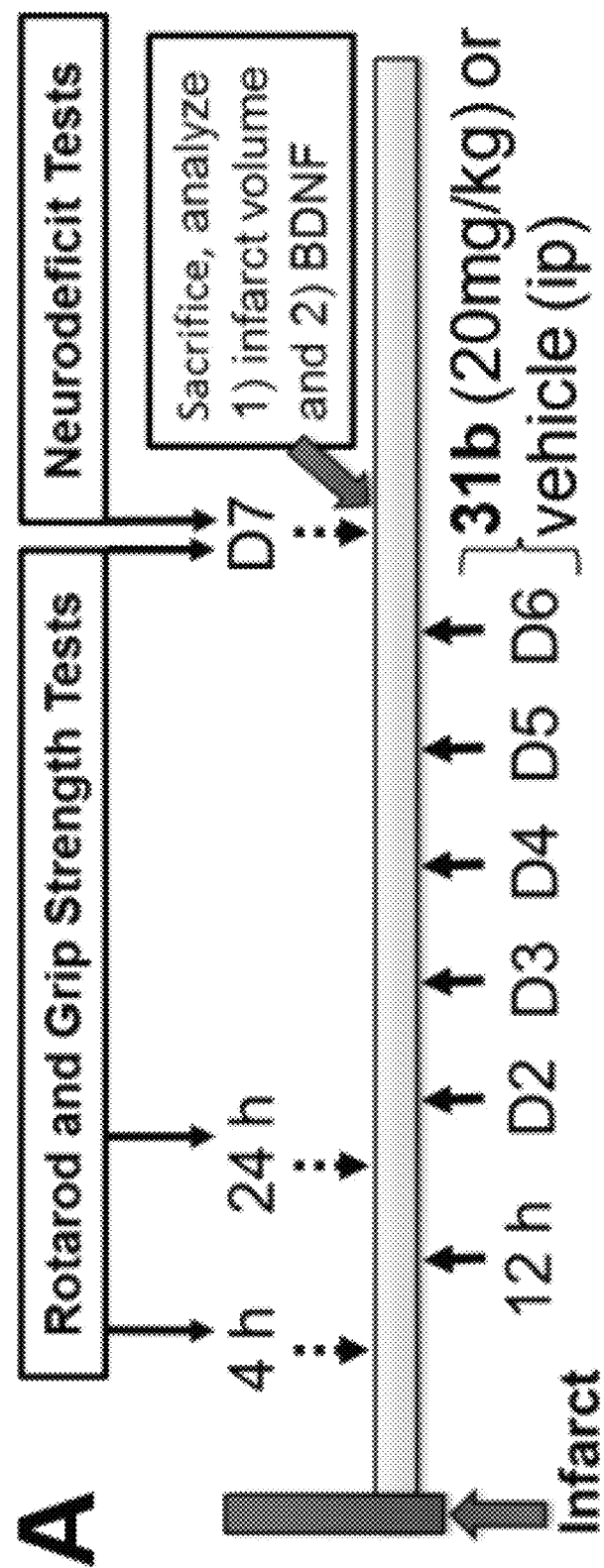
FIGS. 9A-9E: Evaluation of the furoxan 31b.
Figure 9B:
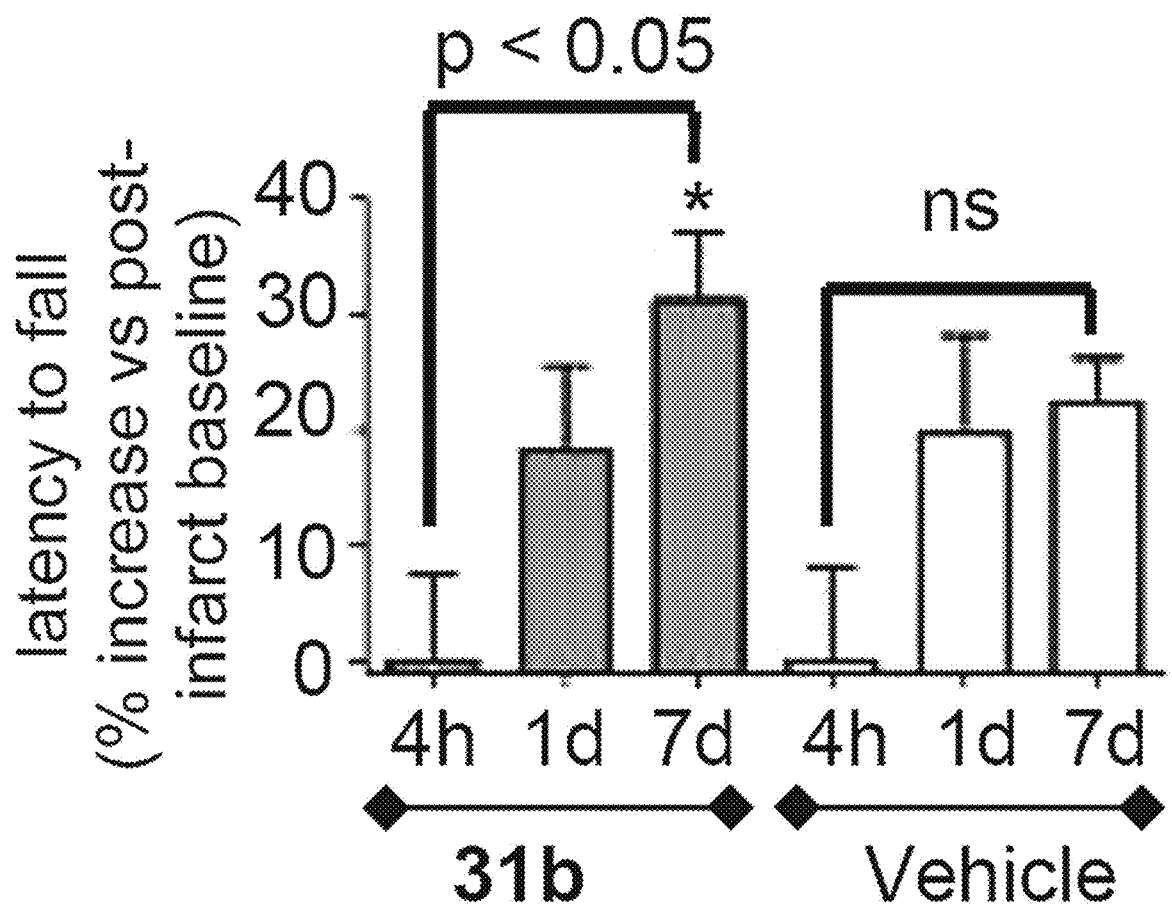
Figure 9C:
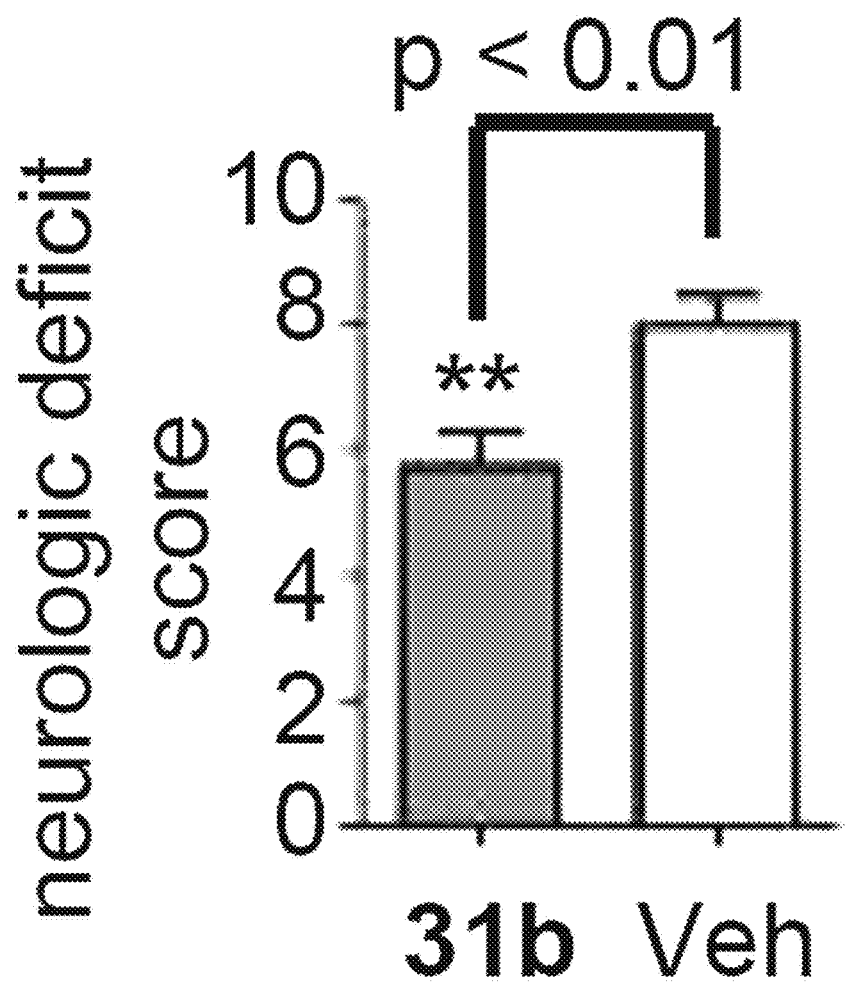
Figure 9D:
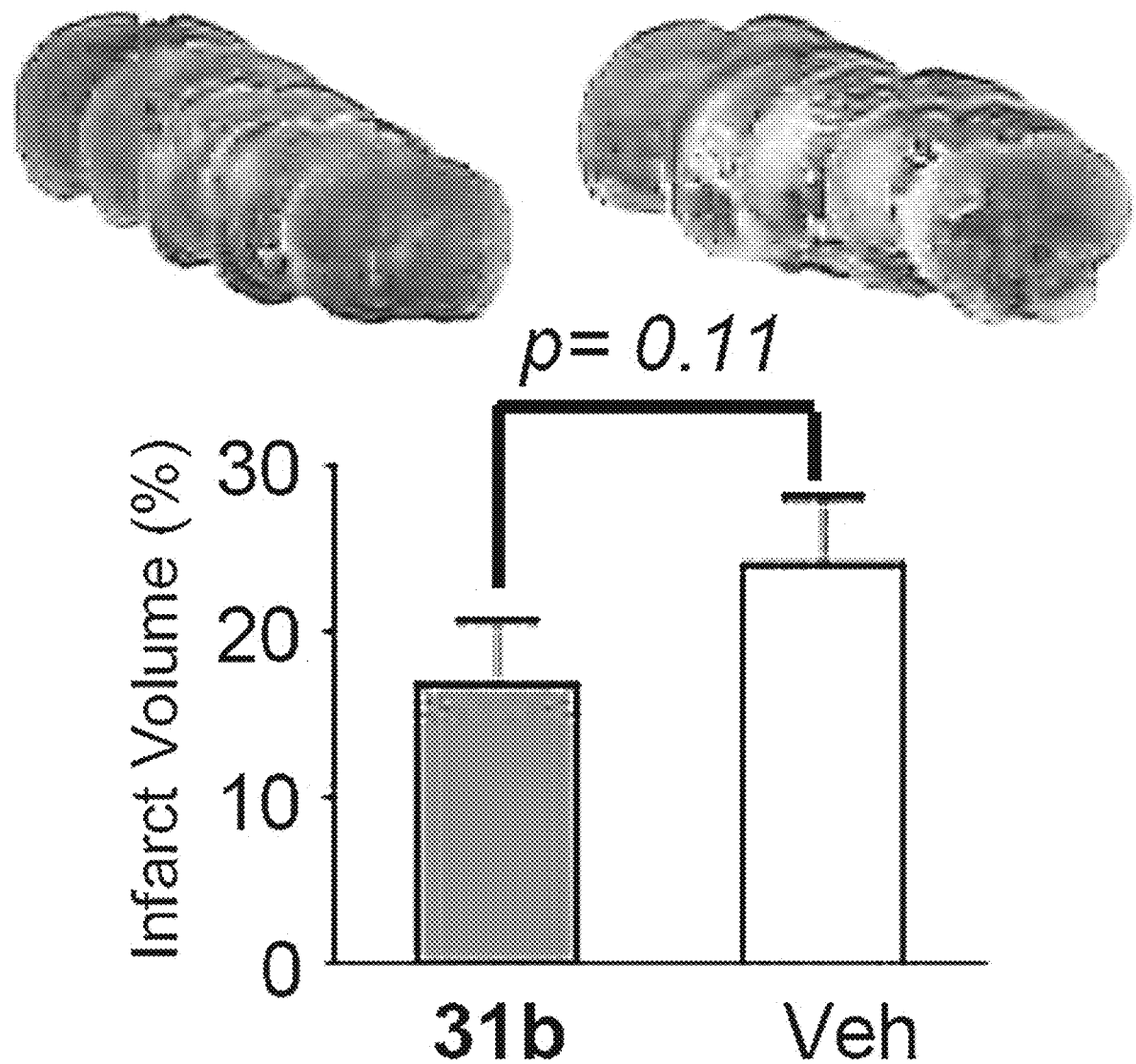
Figure 9E:
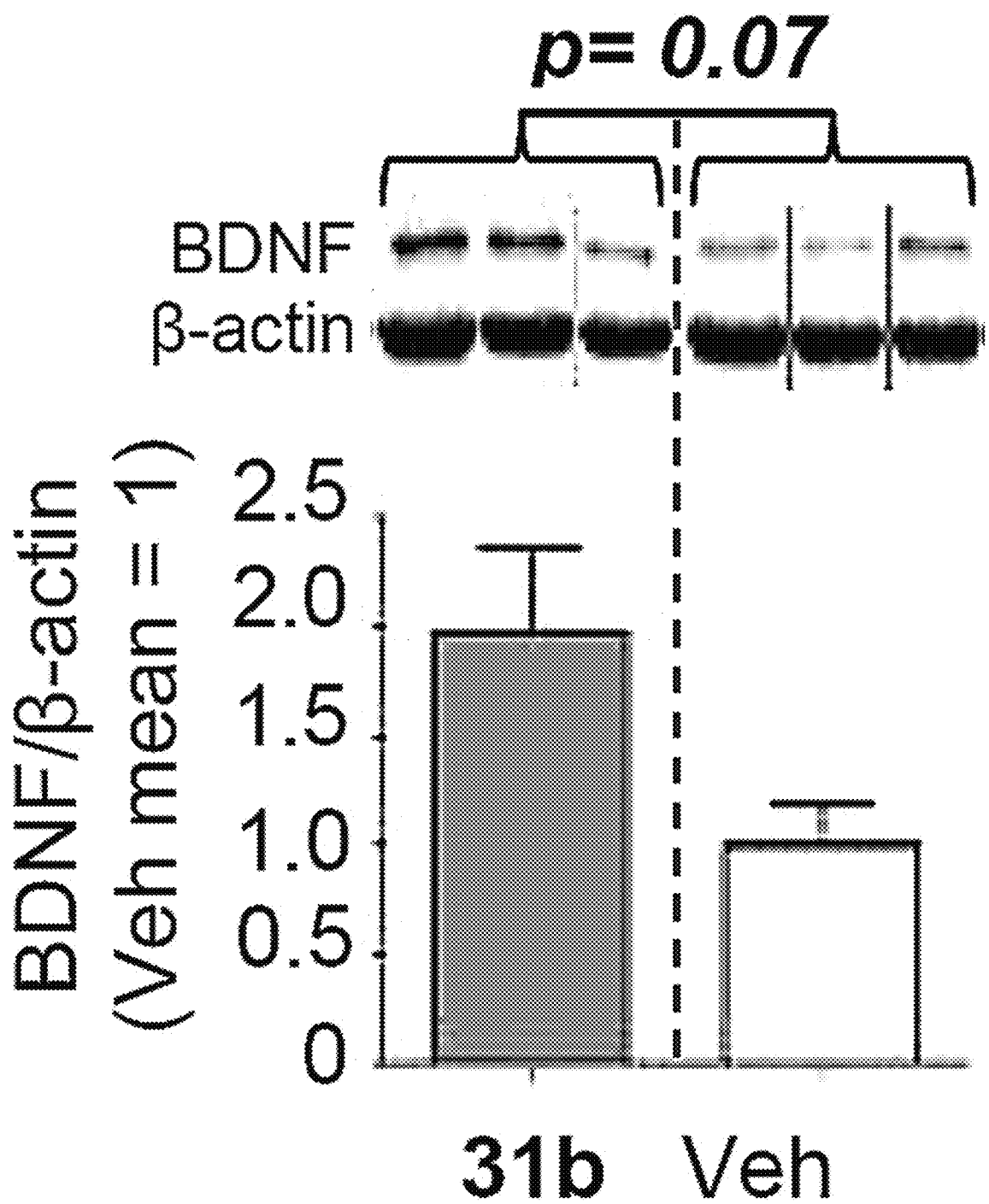

In Vivo Efficacy in a Model of Stroke 31b (20 mg/kg, i.p.) was administered once daily for 6 days beginning 12 hr after permanent MCAO (pMCAO, FIG. 9A). pMCAO was chosen rather than 2-VO because pMCAO is much simpler and more reliable (pMCAO-no loss of animals vs 2-VO~30% lethality 7 days post-op). Ultimately, this model allowed for the provision of evidence of neuroprotective efficacy and effect on BDNF. 31b provided significant improvement in behavioral functional recovery on day 7 based on experiments using the rotarod (FIG. 9B) and neurologic deficit scoring (NDS, FIG. 9C). Infarct volume was reduced by ~30% and BDNF was observed at double the levels of control animals, though a larger N is needed to validate statistical significance (unpaired t-test: infarct p=0.11; BDNF p=0.07).

Methods

Synthesis and Characterization

General Reduction Procedure

The appropriate cinnamic acid (1 eq) was dissolved in anhydrous tetrahydrofuran (THF, 20 mL) and brought to 0° C. under argon. TEA (1 eq) was added dropwise over two minutes and left to stir for another five minutes. Ethyl chloroformate (1 eq) was added dropwise over 5 minutes which gave yield to a white solid. The solution was then filtered through a glass filter. NaBH₄ (3.8 eq) was added portion wise to the filtrate. The reaction was quenched with MeOH (20 mL) added over thirty minutes using a syringe pump and stirred overnight. HCl (1N, 30 mL) was added dropwise over thirty minutes until solution became acidic. The reaction is then extracted with $CH_2Cl_2$ (3×50 mL) and washed with brine (1×100 mL). The concentrated mixture was purified by column chromatography (mobile phase: hexane:ethyl acetate) to give the corresponding cinnamyl alcohol.

(E)-3-(4-fluorophenyl)prop-2-en-1-ol (1)

Synthesized using the general procedure with the following values: (E)-3-(4-fluorophenyl)acrylic acid (2.06 g, 12.4 mmol); TEA (1.26 g, 12.4 mmol); ethyl chloroformate (1.35 g, 12.4 mmol); NaBH₄ (4.70 g, 123.98 mmol); afforded 1 as white solid (762.40 mg, 40.31%). NMR (CDCl₃, 400 MHz): δ 7.36-7.33 (qd, 2H, J=12 Hz); 7.03-6.99 (t); 6.60-6.56 (d, 1H, J=16 Hz); 6.32-6.25 (m); 4.33-4.31 (d, 2H, J=8 Hz).

(E)-3-(4-(trifluoromethyl)phenyl)prop-2-en-1-ol (2)

Synthesized using the general procedure with the following values: (E)-3-(4-(trifluoromethyl)phenyl)acrylic acid (2.00 g, 9.25 mmol); TEA (936.28 mg, 9.25 mmol); ethyl chloroformate (1.00 g, 9.25 mmol); NaBH₄ (1.33 g, 35.16 mmol); afforded 2 as white solid (1.84 g, 98.29%). ¹H NMR (CDCl₃, 400 MHz): δ 7.57-7.55 (2H, d, J=8 Hz); 7.47-7.45 (2H, d, J=8 Hz); 6.68-6.64 (1H, d, J=16 Hz); 6.48-6.42 (1H, m); 4.37-4.35 (2H, d, J=6.7 Hz).

(E)-3-(4-bromophenyl)prop-2-en-1-ol (3)

Synthesized using the general procedure with the following values: (E)-3-(4-bromophenyl)acrylic acid (3.00 g, 13.21 mmol); TEA (1.34 g, 13.21 mmol); ethyl chloroformate (1.43 g, 13.21 mmol); NaBH$_4$ (1.9 g, 50.21 mmol); afforded 3 as white solid (2.27 g, 81.63%). NMR (CDCl$_3$, 400 MHz): δ 7.44-7.42 (d, 2H, J=8 Hz); 7.25-7.23 (d, 2H, J=8 Hz); 6.57-6.53 (d, 1H, J=16 Hz); 6.38-6.31 (m); 4.32-4.30 (d, 2H, J=8 Hz).

(E)-3-(4-(difluoromethoxy)phenyl)prop-2-en-1-ol (4)

Synthesized using the general procedure with the following values: (E)-3-(4-(difluoromethoxy)phenyl)acrylic acid (1.14 g, 5.32 mmol); TEA (540 mg, 5.32 mmol); ethyl chloroformate (579 mg, 5.32 mmol); NaBH$_4$ (2.3 g, 60.68 mmol); afforded 4 as white solid (923 mg, 86.30%). $^1$H NMR (CDCl$_3$, 400 MHz): δ 7.34-7.32 (2H, d, J=8.0 Hz); 7.05-7.03 (2H, d, J=8.0 Hz); 6.68-6.49 (2H, m); 6.32-6.25 (1H, m); 4.31-4.30 (2H, d, J=5.6 Hz).

(E)-3-(4-nitrophenyl)prop-2-en-1-ol (5)

Synthesized using the general procedure with the following values: (E)-3-(4-nitrophenyl)acrylic acid (3.00 g, 15.3 mmol); TEA (1.73 g, 17.1 mmol); ethyl chloroformate (1.85 g, 17.1 mmol); NaBH$_4$ (2.17 g, 59.0 mmol); afforded 5 as yellow solid (1.24 g, 44.53%). $^1$H NMR (CDCl$_3$, 400 MHz): δ 8.22-8.16 (q, 2H); 7.55-7.50 (q, 2H); 6.77-6.70 (t, 1H); 6.60-6.52 (m, 1H); 4.43-4.41 (d, 2H, J=8.8 Hz).

(E)-3-(4-methoxyphenyl)prop-2-en-1-ol (6)

Synthesized using the general procedure with the following values: (E)-3-(4-methoxyphenyl)acrylic acid (3.00 g, 16.84 mmol); TEA (1.7 g, 16.84 mmol); ethyl chloroformate (1.83 g, 16.84 mmol); NaBH$_4$ (4.46 g, 117.85 mmol); afforded 6 as white solid (1.95 g, 70.67%). NMR (DMSO, 400 MHz): δ 7.37-7.35 (2H, d, J=8 Hz); 6.90-6.88 (2H, d, J=8 Hz); 6.52-6.48 (1H, d, J=16 Hz); 6.26-6.19 (1H, m); 4.11-4.1 (2H, d, J=4 Hz); 3.75 (3H, s).

(E)-3-(4-(trifluoromethoxy)phenyl)prop-2-en-1-ol (7)

Synthesized using the general procedure with the following values: (E)-3-(4-(trifluoromethoxy)phenyl)acrylic acid (3.00 g, 12.92 mmol); TEA (1.31 g, 12.92 mmol); ethyl chloroformate (1.40 g, 12.92 mmol); NaBH$_4$ (1.71 g, 45.23 mmol); afforded 7 as white solid (2.44 g, 86.42%). $^1$H NMR (DMSO, 400 MHz): δ 7.62-7.60 (2H, d, J=8 Hz); 7.36-7.34 (2H, d, J=8 Hz); 6.69-6.65 (1H, d, J=16 Hz); 6.53-6.47 (1H, m); 4.21-4.20 (2H, d, J=4 Hz).

(E)-3-(p-tolyl)prop-2-en-1-ol (8)

Synthesized using the general procedure with the following values: (E)-3-(ptolyl) acrylic acid (3.04 g, 18.74 mmol); TEA (1.90 g, 18.74 mmol); ethyl chloroformate (2.03 g, 18.74 mmol); NaBH$_4$ (2.69 g, 71.23 mmol); afforded 8 as white solid (1.57 g, 56.52%). $^1$H NMR (CDCl$_3$, 400 MHz): δ 7.28-7.26 (d, 2H, J=8 Hz); 7.13-7.11 (d, 2H, J=8 Hz); 6.59-6.55 (d, 1H, J=16 Hz); 6.34-6.27 (m); 4.30-4.28 (d, 2H, J=8 Hz); 2.33 (s, 1H).

(E)-3-(4-chlorophenyl)prop-2-en-1-ol (9)

Synthesized using the general procedure with the following values: (E)-3-(4-chlorophenyl)acrylic acid (2.00 g, 10.95 mmol); TEA (1.11 g, 10.95 mmol); ethyl chloroformate (1.19 g, 10.95 mmol); NaBH$_4$ (1.57 g, 41.62 mmol); afforded 9 as white solid (1.30 g, 70.60%). $^1$H NMR (CDCl$_3$, 400 MHz): δ 7.31-7.26 (d, 4H, J=8); 6.58-6.54 (d, 1H, J=16); 6.36-6.30 (m, 1H); 4.32-4.31 (d, 2H, J=4.8).

General Cyclization Procedure

The appropriate cinnamyl alcohol (1 eq) was dissolved in AcOH:DMF (1:1) and brought to 0° C. under argon. Sodium nitrite (10 eq) was then added. The reaction was stirred for 1 hr at 0° C. The reaction mixture was heated, at 40° C. sodium nitrite was added (5 eq) then continued to heat the reaction gradually to 80° C. over 1.5 hours. The reaction was diluted with ice water, and extracted with EA (3×50 mL). Combined organic layers were washed with brine (1×100 mL). The organic layer was then concentrated by rotary evaporation. The concentrated mixture was purified using column chromatography (mobile phase: hexane:ethyl acetate) to give the corresponding furoxan.

4-(4-fluorophenyl)-3-(hydroxymethyl)-1,2,5-oxadiazole 2-oxide (11)

Synthesized using the general procedure with the following values: 1 (762 mg, 5.01 mmol); NaNO$_2$ (5.19 g, 75.15 mmol); afforded 11 as yellow solid (278 mg, 26.37%). $^1$H NMR (CDCl$_3$, 400 MHz): δ7.92-7.88 (2H, qd, J=16 Hz); 7.31-7.29 (2H, t,); 4.78 (2H, s).

3-(hydroxymethyl)-4-(4-(trifluoromethyl)phenyl)-1,2,5-oxadiazole 2-oxide (12)

Synthesized using the general procedure with the following values: 2 (1.51 g, 7.47 mmol); NaNO$_2$ (5.15 g, 74.69 mmol); afforded 12 as yellow solid (699 mg, 35.95%). $^1$H NMR (CDCl$_3$, 400 MHz): δ8.24-8.22 (2H, d, J=8 Hz); 8.02-8.0 (2H, d, J=8 Hz); 4.76-4.72 (2H, d, J=16 Hz); 4.01 (1H, s).

4-(4-bromophenyl)-3-(hydroxymethyl)-1,2,5-oxadiazole 2-oxide (13)

Synthesized using the general procedure with the following values: 3 (1.11 g, 5.21 mmol); NaNO$_2$ (5.39 g, 78.14 mmol); afforded 13 as reddish brown solid (993 mg, 70.35%). NMR (CDCl$_3$, 400 MHz): δ 7.96-7.95 (2H, d, J=4 Hz); 7.85-7.80 (2H, d, J=20 Hz); 4.65 (2H, s).

4-(4-(difluoromethoxy)phenyl)-3-(hydroxymethyl)-1,2,5-oxadiazole 2-oxide (14)

Synthesized using the general procedure with the following values: 4 (923 mg, 4.61 mmol); NaNO$_2$ (2.47 g, 35.80 mmol); afforded 14 as yellow solid (306 mg, 25.72%). $^1$H NMR (CDCl$_3$, 400 MHz): δ 7.88-7.86 (2H, d, J=8.4 Hz); 7.30-7.28 (2H, d, J=8.4 Hz); 6.80-6.43 (1H, m); 4.73 (2H, s).

3-(hydroxymethyl)-4-(4-nitrophenyl)-1,2,5-oxadiazole 2-oxide (15)

Synthesized using the general procedure with the following values: 5 (778 mg, 4.34 mmol); NaNO$_2$ (4.49 g, 65.15 mmol); afforded 15 as yellow solid (439 mg, 42.68%). $^1$H NMR (DMSO, 400 MHz): δ 8.46-8.44 (2H, d, J=8 Hz); 8.20-8.18 (2H, d, J=8 Hz); 4.58 (2H, s).

3-(hydroxymethyl)-4-(4-methoxyphenyl)-1,2,5-oxadiazole 2-oxide (16)

Synthesized using the general procedure with the following values: 6 (1.88 g, 11.45 mmol); NaNO$_2$ (7.89 g, 114.49 mmol); afforded 16 as yellow solid (523 mg, 20.59%). $^1$H NMR (CDCl$_3$, 400 MHz): δ7.92-7.90 (2H, d, J=8 Hz); 7.21-7.19 (2H, d, J=8 Hz); 6.03 (1H, s); 4.57 (2H, s); 3.89 (1H, s).

3-(hydroxymethyl)-4-(4-(trifluoromethoxy)phenyl)-1,2,5-oxadiazole 2-oxide (17)

Synthesized using the general procedure with the following values: 7 (2.33 g, 10.68 mmol); NaNO$_2$ (7.37 g, 106.79 mmol); afforded 17 as yellow solid (538 mg, 18.25%). $^1$H NMR (CDCl$_3$, 400 MHz): δ8.12-8.10 (2H, d, J=8 Hz); 7.69-7.67 (2H, d, J=8 Hz); 6.06 (1H, s); 4.61 (2H, s).

3-(hydroxymethyl)-4-(p-tolyl)-1,2,5-oxadiazole 2-oxide (18)

Synthesized using the general procedure with the following values: 8 (2.28 g, 15.23 mmol); NaNO$_2$ (10.60 g, 153.84 mmol); afforded 18 as yellow solid (687 mg, 21.68%). $^1$H NMR (CDCl$_3$, 400 MHz): δ7.69-7.68 (2H, d, J=4 Hz); 7.33-7.31 (2H, d, J=8 Hz); 4.7 (2H, s); 2.47-2.36 (4H, qd, J=44 Hz).

4-(4-chlorophenyl)-3-(hydroxymethyl)-1,2,5-oxadiazole 2-oxide (19)

Synthesized using the general procedure with the following values: 9 (1.67 g, 9.90 mmol); NaNO$_2$ (13.67 g, 198.08 mmol); afforded 19 as yellow solid (495 mg, 22.05%). $^1$H NMR (CDCl$_3$, 400 MHz): δ7.81-7.79 (2H, d, J=4 Hz); 7.53-7.51 (2H, d, J=8 Hz); 4.72 (2H, s).

3-(hydroxymethyl)-4-phenyl-1,2,5-oxadiazole 2-oxide (20)

Synthesized using the general procedure with the following values: 10 (1.00 g, 7.45 mmol); NaNO$_2$ (5.14 g, 74.53 mmol); afforded 20 as yellow solid (727 mg, 50.87%). $^1$H NMR (CDCl$_3$, 400 MHz): δ 7.81-7.80 (2H, m); 7.59-7.56 (3H, m); 4.745 (2H, s).

General Bromination Procedure

The appropriate furoxan (1 eq) was dissolved in anhydrous CH$_2$Cl$_2$ at 0° C. under argon. PPh$_3$ (1.2 eq) was added in one portion. Reaction was stirred for 15 mins. CBr$_4$ (1.2 eq) was added in 2 portions, ice bath removed and reaction maintained at room temp for 2 hr. The concentrated mixture was purified by column chromatography (mobile phase: hexanes: ethyl acetate) to give the corresponding furoxans.

3-(bromomethyl)-4-(4-fluorophenyl)-1,2,5-oxadiazole 2-oxide (21)

Synthesized using the general procedure with the following values: 11 (408 mg, 2.12 mmol); PPh$_3$ (668 mg, 2.55 mmol); CBr$_4$ (844 mg, 2.55 mmol); afforded 21 as a yellow solid (306 mg, 57.8%). $^1$H NMR (CDCl$_3$, 400 MHz): δ 7.83-7.79 (2H, qd); 7.31-7.29 (2H, t); 4.40 (2H, s).

3-(bromomethyl)-4-(4-(trifluoromethyl)phenyl)-1,2,5-oxadiazole 2-oxide (22)

Synthesized using the general procedure with the following values: 12 (877.30 mg, 3.37 mmol); PPh$_3$ (1.06 g, 4.05 mmol); CBr$_4$ (1.34 g, 4.05 mmol); afforded 22 as yellow solid (366 mg, 33.55%). $^1$H NMR (CDCl$_3$, 400 MHz): δ 7.98-7.96 (2H, d, J=8.4 Hz); 7.88-7.86 (2H, d, J=8.4 Hz); 4.45 (2H, s).

3-(bromomethyl)-4-(4-bromophenyl)-1,2,5-oxadiazole 2-oxide (23)

Synthesized using the general procedure with the following values: 13 (772 mg, 2.85 mmol); PPh$_3$ (897 mg, 3.42 mmol); CBr$_4$ (1.13 g, 3.42 mmol); afforded 23 as yellow solid (554 mg, 58.25%). $^1$H NMR (CDCl$_3$, 400 MHz): δ 7.79-7.76 (2H, m); 7.60-7.57 (2H, m); 4.39 (2H, s).

3-(bromomethyl)-4-(4-(difluoromethoxy)phenyl)-1,2,5-oxadiazole 2-oxide (24)

Synthesized using the general procedure with the following values: 14 (306 mg, 1.19 mmol); PPh$_3$ (373 mg, 1.42 mmol); CBr$_4$ (579 mg, 1.42 mmol); afforded 24 as white oil (334 mg, 81%). $^1$H NMR (CDCl$_3$, 400 MHz): δ 7.81-7.79 (2H, d, J=8.4 Hz); 7.33-7.31 (2H, d, J=8.4 Hz); 6.80-6.44 (1H, m); 4.38 (2H, s).

3-(bromomethyl)-4-(4-nitrophenyl)-1,2,5-oxadiazole 2-oxide (25)

Synthesized using the general procedure with the following values: 15 (440 mg, 1.86 mmol); PPh$_3$ (583.39 mg, 2.23 mmol); CBr$_4$ (737.61 mg, 2.23 mmol); afforded 25 as yellow solid (390 mg, 70.16%). $^1$H NMR (CDCl$_3$, 400 MHz): δ 8.47-8.45 (2H, d, J=8.8 Hz); 8.05-8.03 (2H, d, J=8.8 Hz); 4.43 (2H, s).

3-(bromomethyl)-4-(4-methoxyphenyl)-1,2,5-oxadiazole 2-oxide (26)

Synthesized using the general procedure with the following values: 16 (523 mg, 2.35 mmol); PPh$_3$ (1.00 g, 3.81 mmol); CBr$_4$ (1.26 g, 3.81 mmol); afforded 26 as yellow oil (578 mg, 86.1%). $^1$H NMR (CDCl$_3$, 400 MHz): δ 7.76-7.74 (2H, d, J=8.0 Hz); 7.11-7.09 (2H, d, J=8.0 Hz); 4.42 (2H, s); 3.91 (3H, s).

3-(bromomethyl)-4-(4-(trifluoromethyoxy)phenyl)-1,2,5-oxadiazole 2-oxide (27)

Synthesized using the general procedure with the following values: 17 (538 mg, 1.95 mmol); PPh$_3$ (1.00 g, 3.82 mmol); CBr$_4$ (1.27 g, 3.82 mmol); afforded 27 as slightly yellow solid (558 mg, 84.5%). $^1$H NMR (CDCl$_3$, 400 MHz): δ 7.90-7.88 (2H, d, J=8.0 Hz); 7.47-7.46 (2H, d, J=4 Hz); 4.43 (2H, s).

3-(bromomethyl)-4-(p-tolyl)-1,2,5-oxadiazole 2-oxide (28)

Synthesized using the general procedure with the following values: 18 (650 mg, 3.15 mmol); PPh$_3$ (992 mg, 3.78 mmol); CBr$_4$ (1.25 g, 3.78 mmol); afforded 28 as white solid (605 mg, 71.3%). $^1$H NMR (CDCl$_3$, 400 MHz): δ 7.69-7.67 (2H, d, J=8.4 Hz); 7.40-7.38 (2H, d, J=8.0 Hz); 4.40 (2H, s); 2.46 (3H, s).

3-(bromomethyl)-4-(4-cholophenyl)-1,2,5-oxadiazole 2-oxide (29)

Synthesized using the general procedure with the following values: 19 (711 mg, 3.14 mmol); PPh$_3$ (988 mg, 3.76 mmol); CBr₄ (1.25 g, 3.76 mmol); afforded 29 as yellow oil (477 mg, 52.46%). ¹H NMR (CDCl₃, 400 MHz): δ 7.77-7.75 (2H, d, J=8.4 Hz); 7.59-7.57 (2H, d, J=8.8 Hz); 4.40 (2H, s).

3-(bromomethyl)-4-phenyl-1,2,5-oxadiazole 2-oxide (30)

Synthesized using the general procedure with the following values: 20 (303 mg, 1.58 mmol); PPh₃ (496 mg, 1.89 mmol); CBr₄ (627 mg, 1.89 mmol); afforded 23 as a yellow solid (230 mg, 57.26%). ¹H NMR (CDCl₃, 400 MHz): δ 7.80-7.78 (2H, m); 7.60-7.57 (3H, m); 4.41 (2H, s).

General Substitution Procedure

The appropriate furoxan (1 eq) was dissolved in organic solvent (as specified in quantities) under argon at temperature (as specified in quantities). 4-methylpiperidine (1.1 eq) was added, neat, in one portion. Immediately following, base (as specified in quantities) (1.1 eq) was added in one portion. The reaction was stirred for 15 minutes, then purified using column chromatography (mobile phase: hexane:ethyl acetate) to give the corresponding furoxan. Using TEA as the base gave the optimized reaction yields.

4-(4-fluorophenyl)-3-((4-methylpiperidin-1-yl)methyl)-1,2,5-oxadiazole 2-oxide (31a)

Synthesized using the general procedure with the following values: 21 (1.6 g, 5.86 mmol) was dissolved in DMF (20 mL) at 50° C.; K₂CO₃ (972 mg, 7.03 mmol); 4-methylpiperidine (697 mg, 7.03 mmol); afforded 31a as yellow oil (1.57 g, 91.5%). ¹H NMR (CDCl₃, 400 MHz): δ 8.11-8.07 (2H, m); 7.23-1.18 (2H, m); 3.47 (2H, s); 2.83-2.80 (2H, d, J=11.6 Hz); 2.22-2.15 (2H, td); 1.67-1.64 (2H, d, J=12.8 Hz); 1.40 (1H, m); 1.26-1.19 (2H, m); 0.94-0.93 (3H, d, J=6.4 Hz). ¹³C NMR (CDCl₃, 100 MHz): 165.67, 163.17, 156.84, 130.54-130.45, 123.36-123.33, 116.35-116.13, 53.65, 50.53, 34.21, 30.35, 21.69.

3-((4-methylpiperidin-1-yl)methyl)-4-(4-trifluoromethyl)phenyl)-1,2,5-oxadiazole 2-oxide (32a)

Synthesized using the general procedure using the following values: 22 (300 mg, 0.93 mmol) was dissolved in DMF (2 mL) and heated to 100° C.; K₂CO₃ (141 mg, 1.02 mmol); 4-methylpiperidine (101 mg, 1.02 mmol); afforded 32a as white, crystalline solid (240 mg, 75.7%). ¹H NMR (CDCl₃, 400 MHz): δ 8.26-8.24 (2H, d, J=8 Hz); 7.80-7.78 (2H, d, J=8.4 Hz); 3.49 (2H, s); 2.83-2.80 (2H, d, J=12 Hz); 2.23-2.17 (2H, m); 1.68-1.65 (2H, d, J=12.8 Hz); 1.42-1.40 (1H, m); 1.25-1.18 (2H, m); 0.96-0.93 (3H, m). ¹³C NMR (CDCl₃, 100 MHz): 156.61, 132.92-132.71, 130.50, 128.72, 126.08-126.01, 124.60, 122.79, 53.68, 50.53, 34.16, 30.32, 21.72.

4-(4-bromophenyl)-3-(4-methylpiperidin-1-yl)methyl)-1,2,5-oxadiazole 2-oxide (33a)

Synthesized using the general procedure using the following values: 23 (300 mg, 0.90 mmol) was dissolved in DMF (2 mL) and heated to 100° C.; K₂CO₃ (137 mg, 0.99 mmol); 4-methylpiperidine (98.00 mg, 0.99 mmol); afforded 33a as white solid (178 mg, 56.1%). ¹H NMR (CDCl₃, 400 MHz): δ 7.98-7.95 (2H, m); 7.67-7.64 (2H, m); 3.46 (2H, s); 2.81-2.78 (2H, d, J=11.6 Hz); 2.21-2.15 (2H, m); 1.66-1.63 (2H, d, J=12.8 Hz); 1.42-1.38 (1H, m); 1.22-1.15 (2H, m); 0.94-0.92 (3H, d, J=6.4 Hz). ¹³C NMR (CDCl₃, 100 MHz): 156.91, 132.38, 129.79, 125.96-125.80, 112.90, 53.66, 50.51, 34.17, 30.33, 21.75.

4-(4-(difluoromethoxy)phenyl)-34(4-methylpiperidin-1-yl)methyl)-1,2,5-oxadiazole 2-oxide (34a)

Synthesized using the general procedure using the following values: 24 (270 mg, 0.84 mmol) in DMF (2 mL) and heated to 100° C.; K₂CO₃ (139 mg, 1.01 mmol); 4-methylpiperidine (100 mg, 1.01 mmol); afforded 34a as yellow solid (235 mg, 82%). ¹H NMR (CDCl₃, 400 MHz): δ 8.12-8.10 (2H, d, J=8.8 Hz); 7.27-7.25 (2H, d, J=8.8 Hz); 6.79-6.43 (1H, m); 3.47 (2H, s); 2.82-2.79 (2H, d, J=11.2 Hz); 2.21-2.16 (2H, t); 1.67-1.64 (2H, d, J=12 Hz); 1.42-1.39 (2H, m); 1.26-1.16 (2H, m); 0.94-0.93 (3H, d, J=6.4 Hz). ¹³C NMR (CDCl₃, 100 MHz): 156.81, 153.09, 130.08, 124.12, 119.82, 117.19, 115.46, 113.73, 112.98, 53.67, 50.49, 34.15, 30.32, 21.73.

3-((4-methylpiperidin-1-yl)methyl)-4-(4-nitrophenyl)-1,2,5-oxadiazole 2-oxide (35a)

Synthesized using the general procedure using the following values: 25 (388 mg, 1.29 mmol) in DCM (1.5 mL) and DMF (0.8 mL) and heated to 35° C.; TEA (393 mg; 3.88 mmol); 4-methylpiperdine (154 mg, 1.55 mmol); afforded 35a as light yellow solid (313 mg, 75.99%); ¹H NMR (CDCl₃, 400 MHz): δ 8.34-8.34 (4H, m); 3.52 (2H, s); 2.84-2.81 (2H, d, J=11.2 Hz); 2.25-2.19 (2H, t); 1.70-1.67 (2H, d, J=13.2 Hz); 1.44-1.41 (2H, m); 1.27-1.18 (2H, m); 0.96-0.94 (3H, d, J=6.4 Hz). ¹³C NMR (CDCl₃, 100 MHz): 156.11, 149.46, 133.23, 129.58, 124.37, 112.79, 53.87, 50.82, 34.35, 30.50, 21.87.

4-(4-methoxyphenyl)-34(4-methylpiperdin-1-yl)methyl)-1,2,5-oxadiazole 2-oxide (36a)

Synthesized using the general procedure using the following values: (26) (550 mg, 1.93 mmol) in DMF (5 mL) and heated to 70° C.; K₂CO₃ (497 mg, 3.60 mmol); 4-methylpiperidine (357 mg, 3.60 mmol); afforded 36a as white, slightly yellow solid (563 mg, 96.2%). ¹H NMR (CDCl₃, 400 MHz): δ 7.91-7.89 (2H, d, J=8.8 Hz); 6.94-6.92 (2H, d, J=8.8 Hz); 3.79 (3H, s); 3.39 (2H, s); 2.74-2.71 (2H, d, J=11.6 Hz); 2.11-2.06 (2H, t); 1.57-1.54 (2H, d, J=12.8 Hz); 1.32-1.29 (2H, m); 1.17-1.12 (2H, m); 0.85-0.83 (3H, d, J=6.8 Hz). ¹³C NMR (CDCl₃, 100 MHz): 161.75, 157.45, 129.79, 199.39, 114.49, 133.24, 55.44, 53.68, 50.54, 34.20, 30.36, 21.78.

3-((4-methylpiperdin-1-yl)methyl)-4-(4-(trifluoromethoxy)phenyl)-1,2,5-oxadiazole 2-oxide (37a)

Synthesized using the general procedure using the following values: 27 (500 mg, 1.47 mmol) in DMF (5 mL) and heated to 70° C.; K₂CO₃ (408 mg, 2.95 mmol); 4-methylpiperdine (293 mg, 2.95 mmol); afforded 37a as white solid (492 mg, 93.5%). ¹H NMR (CDCl₃, 400 MHz): δ 8.19-8.16 (2H, d, J=12 Hz); 7.39-7.38 (2H, d, J=4.0 Hz); 3.50 (2H, s); 2.84-2.82 (2H, d, J=8 Hz); 2.23-2.20 (2H, m); 1.69-1.67 (2H, d, J=8.0 Hz); 1.44-1.41 (1H, m); 1.26-1.19 (2H, m); 0.96-0.95 (3H, d, J=4.0 Hz). ¹³C NMR (CDCl₃, 100 MHz): 156.61, 115.16, 130.09, 125.62, 122.94, 121.27, 121.23, 119.51, 112.92, 53.67, 34.16, 30.96, 30.33, 21.72, 11.49.

3-((4-methylpiperdin-1-yl)methyl)-4-(p-tolyl)-1,2,5-oxadiazole 2-oxide (38a)

Synthesized using the general procedure using the following values: 28 (178 mg, 0.66 mmol) in DCM (1 mL) and carried out at room temperature; TEA (201 mg, 1.98 mmol); 4-methylpiperidine (66 mg, 0.66 mmol); afforded 38a as white solid (141 mg, 74.39%). $^1$H NMR (CDCl$_3$, 400 MHz): δ 7.95-7.94 (2H, d); 7.35-7.34 (2H, d); 3.5 (2H, s); 2.84-2.82 (2H, d); 2.46-2.44 (3H, s); 2.21-2.17 (2H, m); 1.67-1.65 (2H, d); 1.41-1.26 (1H, s); 1.24-1.20 (2H, m); 0.95-0.94 (3H, d). $^{13}$C NMR (CDCl$_3$, 100 MHz): 157.76, 141.38, 129.79, 128.11, 124.19, 113.28, 53.68, 50.48, 34.20, 30.35, 21.78-21.54.

4-(4-chlorophenyl)-34(4-methylpiperidin-1-yl)methyl)-1,2,5-oxadiazole 2-oxide (39a)

Synthesized using the general procedure using the following values: 29 (476 mg, 1.64 mmol) in DCM (1.5 mL) heated to 35° C.; TEA (499 mg, 4.93 mmol); 4-methylpiperidine (196 mg, 1.97 mmol); afforded 39a as pale, yellow solid. $^1$H NMR (CDCl$_3$, 400 MHz): δ 8.15-8.13 (2H, d, J=8.8 Hz); 7.61-7.59 (2H, d, J=8.8 Hz); 3.52 (2H, s); 2.91-2.88 (2H, d, J=11.6 Hz); 2.31-2.26 (2H, m); 1.76-1.73 (2H, d, J=12 Hz); 1.35-1.28 (1H, m); 1.04-1.02 (3H, d, J=6.4 Hz). $^{13}$C NMR (CDCl$_3$, 100 MHz): 156.84, 137.39, 129.59, 129.41, 125.50, 112.95, 53.66, 50.51, 34.17, 30.33, 21.74.

3((4-methylpiperidin-1-yl)methyl)-4-phenyl-1,2,5-oxadiaozle 2-oxide (40a)

Synthesized using the general procedure using the following values: (30) (245 mg, 0.96 mmol) in 20 mL DMF and heated to 100° C.; K$_2$CO$_3$ (146 mg, 1.06 mmol); 4-methylpiperidine (105 mg, 1.06 mmol); afforded 40a as white solid (198 mg, 75.4%). $^1$H NMR (CDCl$_3$, 400 MHz): δ 8.04-8.02 (2H, d, J=9.6 Hz); 7.54-7.52 (2H, d, J=6.4 Hz); 3.48 (2H, s); 2.82-2.79 (2H, d, J=11.6 Hz); 2.20-2.14 (2H, m); 1.65-1.62 (2H, d, J=14 Hz); 1.39-1.37 (2H, m); 1.25-1.12 (2H, m); 0.93-0.91 (3H, d, J=6.8 Hz). $^{13}$C NMR (CDCl$_3$, 100 MHz): 157.70, 130.96, 129.01, 128.38, 128.20, 127.10, 113.11, 53.64, 50.47, 34.18, 30.32, 21.70.

General Tautomerization Procedure

The appropriate furoxan was dissolved in toluene (15 mL) and refluxed for 7 days under argon. The resulting mix of tautomers was purified using reverse phase column chromatography (mobile phase: 25 mM ammonia formate, 0.1% formic acid: methanol, 0.1% formic acid). Reported yields indicated isolated yields of purity greater than 95%, as indicated by HPLC UV analysis at 254 nm.

3-(4-fluorophenyl)-44(4-methylpiperidin-1-yl)methyl)-1,2,5 oxadizole 2-oxide (31b)

Synthesized using the general procedure with the following values: (31a) (1.56 g, 5.35 mmol); afforded 31b (556 mg, 35.64%). $^1$H NMR (CDCl$_3$, 400 MHz): δ 8.23-8.19 (2H, m); 7.26-7.18 (2H, m); 3.55 (2H, s); 2.94-2.92 (2H, d, J=11.6 Hz); 2.20-2.14 (2H, t); 1.69-1.66 (2H, d, J=13.6 Hz); 1.57 (1H, s); 1.44-1.42 (2H, m); 1.25-1.20 (2H, m); 0.95-0.93 (3H, d, J=6.8 Hz). $^{13}$C NMR (CDCl$_3$, 100 MHz):164.39, 162.72, 154.47, 130.56, 130.50, 119.29, 119.27, 116.21, 116.02, 115.06, 53.59, 53.49, 34.22, 30.52, 21.76.

4-((4-methylpiperdin-1-yl)methyl)-3-(4-(trifluoromethyl)phenyl)-1,2,5-oxadiazole 2 oxide (32b)

Synthesized using the general procedure with the following values: 32a (100 mg, 0.29 mmol); afforded 32b: $^1$H NMR (CDCl$_3$, 400 MHz): δ 8.39-8.37 (2H, d, J=8.0 Hz); 7.80-7.79 (2H, d, J=4.0 Hz); 3.60 (2H, s); 2.97-2.95 (2H, d, J=8.0 Hz); 1.72-1.70 (2H, d, J=8.0 Hz); 1.46-1.45 (1H, m); 1.28-0.20 (3H, m); 0.97-0.96 (2H, d, J=4.0 Hz). $^{13}$C NMR (CDCl$_3$, 100 MHz): 154.40, 128.54, 125.80, 125.77, 125.75, 114.77, 53.59, 53.46, 34.21, 30.50, 21.74.

3-(4-bromophenyl)-44(4-methylpiperdin-1-yl)methyl)-1,2,5-oxadiazole 2 oxide (33b)

Synthesized using the general procedure with the following values: 33a (100 mg, 1 eq); afforded 33b. $^1$H NMR (CDCl$_3$, 400 MHz): δ 8.13-8.11 (2H, d); 7.68-7.67 (2H, d); 3.57 (2H, s); 2.95-2.94 (2H, d); 2.21-2.17 (2H, t); 1.71-1.69 (2H, d); 1.46-1.44 (1H, m); 1.28-1.19 (2H, m); 0.97-0.96 (3H, d). $^{13}$C NMR (CDCl$_3$, 100 MHz): 154.38, 132.17, 129.69, 124.89, 122.19, 115.19, 53.58-53.47, 34.21, 30.51, 21.76.

3-(4-(difluoromethoxy)phenyl)-4-((4-methylpiperidin-1-yl)methyl)-1,2,5-oxadiazole 2-oxide (34b)

Synthesized using the general procedure with the following values: $^1$H NMR (CDCl$_3$, 400 MHz): δ 8.24-8.22 (2H, d, J=9.2 Hz); 7.26-7.24 (2H, d, J=7.6 Hz); 6.78-6.41 (1H, t); 3.55 (2H, s); 2.95-2.92 (2H, d, J=12); 2.20-2.15 (2H, t); 1.69-1.66 (2H, d, J=12.4); 1.57 (2H, s); 1.25-1.20 (2H, m); 0.95-0.94 (3H, d, J=6.4 Hz). $^{13}$C NMR (CDCl$_3$, 100 MHz): 154.45, 152.26, 130.07, 120.26, 119.60, 117.20, 115.46, 114.99, 113.73, 53.60-53.47, 34.23, 30.52, 21.76.

3-(4-methoxyphenyl)-4-((methylpiperidin-1-yl)methyl)-1,2,5-oxadiazole 2-oxide (36b)

Synthesized using the general procedure with the following values: $^1$H NMR (CDCl$_3$, 400 MHz): δ 8.12-8.10 (2H, d, J=8.8 Hz); 7.03-7.01 (2H, d, J=8.8 Hz); 3.87 (3H, s); 3.54 (2H, s); 2.96-2.93 (2H, d, J=11.6 Hz); 2.19-2.13 (2H, t); 1.69-1.66 (2H, d, J=12.4 Hz); 1.43-1.41 (2H, m); 1.28-1.18 (2H, m); 0.95-0.93 (3H, d, J=6.4 Hz). $^{13}$C NMR (CDCl$_3$, 100 MHz): 160.99, 154.60, 129.80, 115.56, 115.20, 114.33, 55.42, 53.61-53.50, 34.24, 30.55, 21.79.

4-((4-methylpiperidin-1-yl)methyl)-3-(4-(trifluoromethoxy)phenyl)-1,2,5-oxadiazole 2-oxide (37b)

Synthesized using the general procedure with the following values: $^1$H NMR (CDCl$_3$, 400 MHz): 8.30-8.29 (2H, d, J=4.0 Hz); 7.38-7.29 (2H, d, J=36.0 Hz); 3.59 (2H, s); 2.96-2.95 (2H, d, J=4.0 Hz); 2.22-2.18 (2H, t); 1.72-1.69 (2H, d, J=12.0 Hz); 1.48-1.43 (1H, m); 1.28-1.22 (2H, m); 0.97-0.96 (3H, d, J=4.0 Hz). $^{13}$C NMR (CDCl$_3$, 100 MHz): 154.42, 150.29, 130.05, 121.83, 121.22, 121.07, 119.51, 114.82, 53.59-53.45, 34.21, 30.51, 21.74.

4-((4-methylpiperdin-1-yl)methyl)-3-(p-tolyl)-1,2,5-oxadiazole 2-oxide (38b)

Synthesized using the general procedure with the following values: 38a (119.00 mg, 0.41 mmol) afforded 38b (12.4 mg, 10.42%). $^1$H NMR (CDCl$_3$, 400 MHz): δ 8.03-8.02 (2H, d, J=4.0 Hz); 7.33-7.32 (2H, d, J=4.0 Hz); 3.55 (2H, s);

2.96-2.94 (2H, d, J=8.0 Hz); 2.42 (3H, s); 2.18-2.14 (2H, t); 1.68-1.66 (2H, d, J=8.0 Hz); 1.42 (1H, s); 1.26-1.20 (2H, m); 0.95-0.94 (3H, d, J=4.0 Hz). $^{13}$C NMR (CDCl$_3$, 100 MHz): 154.65, 140.73, 129.60, 128.05, 120.21, 115.66, 53.60, 53.45, 34.24, 30.54, 21.79, 21.54.

3-(4-chlorophenyl)-4-(4-methylpiperidin-1-yl) methyl)-1,2,5-oxadiazole 2-oxide (39b)

Synthesized using the general procedure with the following values: 39a (338.40 mg, 1.10 mmol) afforded 39b as pale, yellow solid (28.9 mg, 8.54%). $^1$H NMR (CDCl$_3$, 400 MHz): δ 8.18-8.17 (2H, d, J=4.0 Hz); 7.52-7.50 (2H, d, J=8.0 Hz); 3.57 (2H, s); 2.95-2.93 (2H, d, J=8.0 Hz); 2.21-2.17 (3H, m); 1.70-1.68 (2H, d, J=8.0 Hz); 1.46-1.42 (1H, m); 1.27-1.19 (3H, m); 0.97-0.95 (3H, d, J=4.0 Hz). $^{13}$C NMR (CDCl$_3$, 100 MHz): 154.41, 136.49, 129.51, 129.19, 121.70, 114.98, 53.58, 53.47, 34.21, 30.97, 30.51, 21.75.

4-((4-methylpiperdin-1-yl)methyl)-3-phenyl-1,2,5-oxadiazole 2-oxide (40b)

Synthesized using the general procedure with the following values: 40a (250 mg, 0.91 mmol) afforded 40b as pale, yellow solid (53 mg, 21.2%). $^1$H NMR (CDCl$_3$, 400 MHz): δ 8.15-8.14 (2H, d, J=4.0 Hz); 7.55-7.49 (3H, m); 3.58 (2H, s); 2.98-2.96 (2H, d, J=8.0 Hz); 2.20-2.16 (2H, m); 1.70-1.68 (2H, d, J=8.0 Hz); 1.45-1.41 (1H, m); 1.28-1.21 (2H, m); 0.97-0.95 (2H, d, J=8.0 Hz). $^{13}$C NMR (CDCl$_3$, 100 MHz): 154.65, 130.37, 128.87, 128.18, 123.22, 115.59, 53.61, 53.41, 34.23, 30.54, 21.79.

Radiolabeled Synthesis
Radiolabeled Substitution Procedure

All radiolabeled reagents were purchased from commercially available sources and used without further purification. 21 (255 mg, 0.93 mmol) was dissolved in DCM (5 mL) while stirring at r. t. under argon. A stirred solution of TEA (283 mg, 2.80 mmol) and 4-methylpiperidine-2,2,6,6-d$^4$ (100 mg, 0.93 mmol) was added to the 21 solution. The reaction was stirred for 10 minutes, then purified using column chromatography (mobile phase: hexane:ethyl acetate) to give 41a (255 mg, 91%).

4-(4-fluorophenyl)-34(4-methylpiperidin-1-yl-2,2,6, 6-d4)methyl)-1,2,5-oxadiazole 2-oxide (41a)

$^1$H NMR (CDCl$_3$, 400 MHz): δ 8.10-8.09 (2H, t); 7.24-7.21 (2H, t); 3.49 (2H, s); 1.67-1.64 (2H, dd); 1.43-1.39 (1H, m); 1.22-1.18 (2H, t); 0.95-0.94 (3H, d, J=4.0 Hz). 13C NMR (CDCl$_3$, 100 MHz): 165.23, 163.56, 156.89, 130.51, 130.45, 123.24, 123.22, 116.37, 116.22, 113.04, 53.07-52.54, 50.40, 34.05, 30.24, 21.77.

Radiolabeled Tautomerization Procedure 41a (215 mg, 0.73 mmol) was dissolved in toluene (5 mL) and refluxed for 6 days to afford 41b. Separation was carried out according to the general procedure.

3-(4-fluorophenyl)-44(4-methylpiperidin-1-yl-2,2,6, 6-d4)methyl)-1,2,5-oxadiazole 2-oxide (31d)

$^1$H NMR (CDCl$_3$, 400 MHz): δ 8.24-8.21 (2H, m); 7.24-7.21 (2H, t); 3.57 (2H, s); 1.69-1.67 (2H, dd); 1.46-1.44 (1H, m); 1.24-1.19 (2H, t); 0.97-0.96 (3H, d, J=4.0 Hz). $^{13}$C NMR (CDCl$_3$, 100 MHz): 164.38, 162.71, 130.56-130.50, 119.30, 119.28, 116.20, 116.06, 115.05, 53.35, 52.99, 52.46, 34.10, 30.42, 21.79.

Crystal Structure Characterization of 31b

FIGS. 10-16 show results of the characterization of the crystal structure of 31b.

A clear colorless irregular prism-like specimen of $C_{15}H_{18}FN_3O_2$, having approximate dimensions of 0.058 mm×0.156 mm×0.270 mm, was used for the X-ray crystallographic analysis. The X-ray intensity data were measured. The integration of the data using a monoclinic unit cell yielded a total of 26380 reflections to a maximum θ angle of 33.11° (0.65 Å resolution), of which 5531 were independent (average redundancy 4.769, completeness=95.1%, Rint=4.72%, Rsig=4.02%) and 4041 (73.06%) were greater than 2σ(F2). The final cell constants of a=11.3374(14) Å, b=7.2234(9) Å, c=18.825(2) Å, β=97.601(2)°, volume=1528.1(3) Å3, are based upon the refinement of the XYZ-centroids of reflections above 20σ(I). The final anisotropic full-matrix least-squares refinement on F2 with 255 variables converged at R1=5.17%, for the observed data and wR2=14.18% for all data. The methyl group (C15) is disordered. The occupancy of the C15 atoms was refined to be 50% and then fixed. They are refined with isotropic atomic displacement parameters; the bonded hydrogen atoms were calculated on idealized hydrogens and refined as riding atoms. The goodness-of-fit was 1.012. The largest peak in the final difference electron density synthesis was 0.487 e–/Å3 and the largest hole was −0.540 e–/Å3 with an RMS deviation of 0.058 e$^-$/Å$^3$. On the basis of the final model, the calculated density was 1.266 g/cm$^3$ and F(000), 616 e$^-$.

Step Through Passive Avoidance (STPA)

All procedures were performed under the approved IACUC protocol #108451. Male C57BL/6 mice (Envigo), N=9 per group, were habituated at the animal facility for at least 14 days. Ear tags were applied and animals weighed. 2 hr prior to the drug adminstration the mice were individually acclimated to the illuminated compartment to assess tendency to enter the dark chamber (measured in seconds). In this phase no shock was be delivered. All mice moved readily into the dark compartment and demonstrated a mean latency to enter the dark chamber of <30 seconds, which is considered to be normal behavior. The mice were then administered either vehicle (95 [0.9% NaCl]:5 [DMSO]) or 31b (0.1, 1, 10, or 20 mg/kg) via i.p. injection (50 μL) at 1 h or 2 h prior to training. Scopolamine (1 mg/kg, i.p.) or vehicle (0.9% NaCl) was administered 30 min prior to training. Mice were individually placed into the light compartment and upon translocation to the dark compartment the guiltine door closed and the mice were trained by delivering a mild adversive stimulus (0.5 mA) via the electrified floor grading of the dark chamber. Each mouse was held in the dark chamber for 30 seconds, then returned to their cage for 120 seconds before the second training session. Mice which did not enter the dark chamber after 300 seconds during the second training phase were lightly pushed to the dark side. Memory retention was measured 24 hours after training by placing the same mouse in the light chamber and measuring latency to enter the dark chamber (no aversive stimulus is delivered during the retention test). Data was analyzed by one way ANOVA analysis with Dunnett's post-hoc test.

In Vitro Reactivity and Metabolism Analysis

Temperature controlled autosampler. LC utilized a Kinetex-core column (Phenomenex): 2.6 um C18 100 A, 100×4.6 mm.

HPLC method: solvents, H$_2$O [0.1% FA]—solvent A; MeOH [0.1% FA]—solvent B; flow rate 1.0 mL/min. Gradient: t=2 min, 5% B; t=6 min, 95% B; t=7.0 min, 95% B; t=7.01, 5% B. Stop time: 10 min. As described above, thiol reactivity was analyzed via incubations containing the furoxan (250 μM) in the presence or absence of excess (5 mM) cysteine (or N-acetylcysteine [NAc]) in PBS (50 mM, pH 7.4) at 37° C. Incubations were placed in a temperature controlled HPLC autosampler and aliquots were analyzed by HPLC-UVvis periodically for 2-24 hr. Percent furoxan remaining was determined based on the area under the curve (AUC) of the HPLC UV-absorbance spectrum. Similarly, rat liver microsomes were incubated with 31b in the presence or absence of NADPH to determine microsomal stability. Warfarin and verapamil were used as slow and fast metabolizing controls.

Pharmacokinetic Analysis

Forebrain tissue (~30 mg) was homogenized in 1 ml of tissue extraction buffer (Invitrogen) containing a protease inhibitor cocktail (PIC). 100 μL of the resulting homogenate (or 100 μL of plasma) was spiked with 2% Formic acid (200 μL, containing 41b [0.5 μM]—internal standard) and vortexed for 1 min. The mixture was applied to an Evolute Express ABN column (Biotage) and filtered through via vacuum filtration. The matrix was washed with $dH_2O$ (1 mL) and analytes eluted with MeOH (1 mL). The resulting extract was evaporated to dryness by passing over air and reconstituted in $ACN/dH_2O$ (100 μL). A 10 μL injection was analyzed by LC-MS/MS. Analysis was carried out on a Shimadzu Nexera XR HPLC coupled with a Shimadzu 8050 triple quadrupole mass spectrometer. LC utilized a Kinetex-core column (Phenomenex): 2.6 um C18 100 A, 100×4.6 mm. HPLC Method: solvents, $H_2O$ [0.1% FA]—solvent A; MeOH [0.1% FA]—solvent B; flow rate 1.0 mL/min (utilized Tsplitter, mass spectrometer effective flow rate 0.4 mL/min). Gradient: t=2 min, 5% B; t=6 min, 95% B; t=7.0 min, 95% B; t=7.01, 5% B. Stop time 10 min. Diverter valve was utilized and eluent only averted to MS from 5 min-8 min. Quantity was determined based on the AUC of the internal standard versus the AUC of the analyte peak.

Permanent Middle Carotid Artery Occlusion

Locomotor activity was evaluated by means of a rotarod task by a person blinded to the treatment groups. Mice were placed on a horizontal rod (Columbus Instruments, OH) that was made to rotate at 1 rpm with an acceleration rate of 1 rpm every 10 s until the animal fell from the rod. Each animal was tested three times per trial. All the animals were trained on the rotarod assembly prior to surgery. The duration for which each animal was able to stay on the accelerating rod was recorded as the latency to fall and registered manually. Locomotor activity was monitored 4 h before, 24 h, postsurgery and 7 days after p-MCAO surgery Grip strength was evaluated by holding the mice by tails and placing their forelimbs on a specially designed pull bar assemblies (Grip strength meter, Columbus Instruments, OH). Peak amount of force animals exert was displayed on the digital display and noted. Each animal was tested three times per trial at 4 h before, 2 and 7 days after p-MCAO surgery. NDS were evaluated by an optimized 28-point score pattern. A person blinded to the treatment evaluated NDS 7 days after p-MCAO; the evaluation included both sensory and motor deficits, such as body symmetry, gait, climbing, circling behavior, front limb symmetry, compulsory circling, and whisker response. Each of the seven tests included in the 28-point NDS was graded from 0 to 4, with higher scores indicating severe deficits. Animals from all the groups were euthanized 7 days after p-MCAO. Brains were dissected out and sliced into five 2-mm-thick coronal sections before incubating in 1% triphenyltetrazolium chloride (TTC) (Sigma Co., MI). The infarct area was estimated from five slices of each brain, measuring rostral and caudal sides of each individual slice in conjunction with the thickness and expressed as a percentage of the volume of the contralateral hemisphere. A person blinded to the treatment groups measured the infarct volume with the help of ImageJ software provided by NIH.

Synthesis of Heterocyclic Amines 4-((4-methylpiperidin-1-yl)methyl)-3-(3-(trifluoromethoxy)phenyl)-1,2,5-oxadiazole 2-oxide (AH-4-52)

$^1$H NMR (CDCl$_3$, 600 MHz): δ 8.36 (1H, s); 8.19-8.17 (1H, m); 7.60-7.57 (1H, t); 7.38-7.36 (1H, dt, J=8.3 Hz); 3.59 (2H, s); 2.97-2.95 (2H, d, J=11.6 Hz); 2.22-2.17 (2H, td); 1.71-1.69 (2H, d, J=14.0 Hz); 1.47-1.43 (1H, m); 1.29-1.22 (2H, m); 0.97-0.96 (3H, d, J=6.5 Hz). $^{13}$C NMR (CDCl$_3$, 600 MHz): 154.3, 149.4, 130.4, 126.1, 125.2, 123.1, 121.8, 121.3, 119.6, 114.7, 53.6, 53.5, 34.0, 30.5, 21.7. Measured purity at 254 nm: 99.5%; 282 nm: 99.3%.

4-(azepan-1-ylmethyl)-3-(3-(trifluoromethoxy)phenyl)-1,2,5-oxadiazole 2-oxide (AH-4-53)

$^1$H NMR (CDCl$_3$, 600 MHz): δ 8.32 (1H, s); 8.21-8.19 (1H, m); 7.60-7.57 (1H, t); 7.39-7.37 (1H, dt; J=8.3 Hz); 3.75 (2H, s); 2.79-2.77 (4H, t); 1.69-1.67 (4H, br); 1.64-1.61 (4H, m). $^{13}$C NMR (CDCl$_3$, 600 MHz): 155.1, 149.5, 130.3, 126.1, 125.3, 122.9, 121.7, 121.3, 119.6, 114.7, 55.2, 54.8, 53.0, 28.1, 26.8. Measured purity at 254 nm: 95.7%; 282 nm: 97.9%.

4-(((3aR,6aS)-tetrahydro-1H-furo[3,4-c]pyrrol-5 (3H)-yl)methyl)-3-(3-(trifluoromethoxy)phenyl)-1,2, 5-oxadiazole 2-oxide (AH-4-54)

$^1$H NMR (CDCl$_3$, 600 MHz): δ 8.22 (1H, s); 8.15-8.14 (1H, m), 7.60-7.57 (1H, t); 7.338-7.36 (1H, dt, J=8.3 Hz); 3.93-3.90 (2H, q), 3.76 (2H, s); 3.49-3.47 (2H, dd, J=4.7 Hz); 2.89-2.87 (2H, m); 2.78-2.76 (2H, q); 2.62-2.59 (2H, dd, J=6.6 Hz). $^{13}$C NMR (CDCl$_3$, 600 MHz): 154.5, 149.5, 130.5, 125.9, 125.0, 123.0, 121.3, 121.2, 114.3, 73.8, 58.7, 49.9, 43.6. Measured purity at 254 nm: 98.4%; 282 nm: 98.4%.

4-(((3aR,7aS)-hexahydrofuro[3,2-c]pyridin-5(4H)-yl)methyl)-3-(3-(trifluoromethoxy)phenyl)-1,2,5-oxadiazole 2-oxide (AH-4-55)

$^1$H NMR (CDCl$_3$, 600 MHz): δ 8.31 (1H, s); 8.16-8.15 (1H, m); 7.60-7.58 (1H, t); 7.38-7.37 (1H, dt, J=8.3 Hz); 4.03-3.99 (1H, q); 3.89-3.85 (2H, m); 3.65-3.57 (2H, q); 2.77-2.74 (1H, m); 2.69-2.65 (1H, m); 2.48-2.43 (1H, td); 2.34-2.29 (1H, br); 2.15-2.12 (1H, t); 2.07-2.00 (2H, m); 1.93-1.87 (1H, m); 1.69-1.65 (1H, m). $^{13}$C NMR (CDCl$_3$, 600 MHz): 154.0, 149.4, 130.5, 126.0, 125.2, 123.1, 121.6, 121.3, 119.6, 114.6, 74.6, 66.1, 53.9, 53.3, 48.6, 37.3, 29.7, 27.7. Measured purity at 254 nm: 94.5%; 282 nm: 97.6%.

4-(((4aR,7a5)-hexahydro-6H-[1,4]dioxino[2,3-c] pyrrol-6-yl)methyl)-3-(3-(trifluoromethoxy)phenyl)-1,2,5-oxadiazole 2-oxide (AH-4-56)

$^1$H NMR (CDCl$_3$, 600 MHz): δ 8.16(1H, s); 8.09-8.07 (1H, d, J=8.0 Hz); 7.60-7.57 (1H, t); 7.37-7.36 (1H, dt, J=8.3 Hz); 4.18-4.15 (2H, quint); 3.89 (2H, s); 3.86-3.82 (2H, m); 3.64-3.61 (2H, m); 3.03-3.02 (4H, d, J=5.2 Hz). $^{13}$C NMR (CDCl$_3$, 600 MHz): 154.5, 149.5, 130.6, 126.0, 125.0, 123.0, 121.3, 121.1, 119.6, 114.3, 73.3, 62.6, 54.2, 51.0. Measured purity at 254 nm: 95.0%; 282 nm: 95.7%.

3-(4-bromo-3-fluorophenyl)-4-((4-methylpiperidin-1-yl)methyl)-1,2,5-oxadiazole 2-oxide (AH-4-58)

$^1$H NMR (CDCl$_3$, 600 MHz): δ 8.75-8.74 (1H, dd, J=4.4 Hz); 8.21-8.19 (1H, m); 7.30-7.27 (1H, t); 3.57 (2H, s); 2.98-2.96 (2H, d, J=11.6 Hz); 2.24-2.20 (2H, td); 1.73-1.71 (2H, d, J=14.0 Hz); 1.48-1.45 (1H, m); 1.34-1.27 (2H, m); 0.99-0.98 (3H, d, J=6.6 Hz). $^{13}$C NMR (CDCl$_3$, 600 MHz): 160.7, 159.0, 154.3, 134.6, 128.60, 128.55, 120.80, 120.77, 117.1, 117.0, 114.1, 109.8, 109.7, 53.5, 53.4, 34.2, 30.5, 21.8. Measured purity at 254 nm: 98.9%; 282 nm: 98.6%.

4-(azepan-1-ylmethyl)-3-(4-bromo-3-fluorophenyl)-1,2,5-oxadiazole 2-oxide (AH-4-59)

$^1$H NMR (CDCl$_3$, 600 MHz): δ8.71-8.70 (1H, dd, J=4.4 Hz); 8.25-8.22 (1H, m); 7.30-7.28 (1H, t); 3.73 (2H, s); 2.80-2.78 (4H, t); 1.72-1.70 (4H, br); 1.67-1.64 (4H, m). $^{13}$C NMR (CDCl$_3$, 600 MHz): 160.7, 159.0, 155.0, 134.2, 128.60, 128.55, 120.85, 120.82, 117.1, 116.9, 114.2, 109.9, 109.8, 54.8, 52.9, 28.2, 26.8. Measured purity at 254 nm: 99.1%; 282 nm: 99.6%.

3-(4-bromo-3-fluorophenyl)-4-(((3aR,6aS)-tetrahydro-1H-furo[3,4-c]pyrrol-5(3H)-yl)methyl)-1,2,5-oxadiazole 2-oxide (AH-4-60)

$^1$H NMR (CDCl$_3$, 600 MHz): δ8.58-8.56 (1H, dd, J=4.3 Hz); 8.19-8.17 (1H, m); 7.30-7.28 (1H, t); 3.96-3.93 (2H, q); 3.74 (2H, s); 3.55-3.53 (2H, dd, J=4.6 Hz); 2.91-2.88 (2H, m); 2.76-2.73 (2H, m); 2.69-2.67 (2H, dd, J=7.0 Hz). $^{13}$C NMR (CDCl$_3$, 600 MHz): 160.8, 159.1, 154.4, 133.9, 128.6, 128.5, 120.61, 120.59, 117.3, 117.1, 113.8, 110.0, 109.9, 74.1, 58.7, 49.9, 43.6. Measured purity at 254 nm: 97.6%; 282 nm: 99.1%.

3-(4-bromo-3-fluorophenyl)-4-(((3aR,7aS)-hexahydrofuro[3,2-c]pyridin-5(4H)-yl)methyl)-1,2,5-oxadiazole 2-oxide (AH-4-61)

$^1$H NMR (CDCl$_3$, 600 MHz): δ8.72-8.70 (1H, dd, J=4.4 Hz); 8.20-8.17 (1H, m); 7.31-7.28 (1H, t); 4.04-4.00 (1H, q); 3.90-3.85 (2H, m); 3.62-3.55 (2H, q); 2.79-2.75 (1H, m); 2.72-2.69 (1H, m); 2.50-2.45 (1H, td); 2.38-2.33 (1H, br); 2.16-2.12 (1H, t); 2.10-2.04 (2H, m); 1.99-1.93 (1H, m); 1.70-1.65 (1H, m). $^{13}$C NMR (CDCl$_3$, 600 MHz): 160.7, 159.0, 154.0, 134.3, 128.50, 128.45, 120.76, 120.74, 117.2, 117.0, 114.0, 109.8, 109.7, 74.6, 66.1, 53.8, 53.3, 48.5, 37.4, 29.8, 27.9. Measured purity at 254 nm: 99.5%; 282 nm: 99.4%.

3-(4-bromo-3-fluorophenyl)-4-(((4aR,7aS)-hexahydro-6H-[1,4]dioxino[2,3-c]pyrrol-6-yl)methyl)-1,2,5-oxadiazole 2-oxide (AH-4-62)

$^1$H NMR (CDCl$_3$, 600 MHz): δ8.54-8.52 (1H, dd, J=4.3 Hz); 8.13-8.10 (1H, m); 7.30-7.27 (1H, t); 4.20-4.17 (2H, quint); 3.88-3.84 (4H, m); 3.65-3.61 (2H, q); 3.06-3.01 (4H, m). $^{13}$C NMR (CDCl$_3$, 600 MHz): 160.8, 159.1, 154.4, 134.1, 128.7, 128.6, 120.62, 120.60, 117.3, 117.1, 113.7, 110.0, 109.9, 73.3, 62.7, 54.2, 50.9. Measured purity at 254 nm: 99.3%; 282 nm: 99.7%.

4-((4-methylpiperidin-1-yl)methyl)-3-(3,4,5-trifluorophenyl)-1,2,5-oxadiazole 2-oxide (AH-4-67)

$^1$H NMR (CDCl$_3$, 600 MHz): δ8.23-8.19 (2H, m); 3.59 (1H, s); 2.97-2.95 (2H, d, J=11.7 Hz); 2.25-2.21 (2H, td); 1.74-1.72 (2H, d, J=14.1 Hz); 1.50-1.45 (1H, m); 1.30-1.23 (2H, m); 0.99-0.98 (3H, d, J=6.6 Hz). $^{13}$C NMR (CDCl$_3$, 600 MHz): 154.0, 152.28, 152.25, 152.21, 152.18, 150.62, 150.59, 150.55, 141.5, 139.8, 119.3, 119.2, 113.8, 113.1, 113.0, 112.92, 112.89, 53.5, 53.4, 34.1, 30.5, 21.7. Measured purity at 254 nm: 99.1%; 282 nm: 99.3%.

4-(azepan-1-ylmethyl)-3-(3,4,5-trifluorophenyl)-1,2,5-oxadiazole 2-oxide (AH-4-68)

$^1$H NMR (CDCl$_3$, 600 MHz): δ8.27-8.25 (2H, m); 3.75 (2H, s); 2.80-2.78 (4H, t); 1.72-1.70 (4H, br); 1.66-1.64 (4H, m). $^{13}$C NMR (CDCl$_3$, 600 MHz): 154.7, 152.29, 152.26, 152.3, 152.20, 150.64, 150.61, 150.57, 150.54, 141.5, 139.8, 119.32, 119.29, 119.26, 113.9, 112.99, 112.95, 112.86, 112.83, 55.1, 54.7, 53.0, 28.2, 28.1, 26.8. Measured purity at 254 nm: 99.3%; 282 nm: 99.4%.

4-(((3aR,6aS)-tetrahydro-1H-furo[3,4-c]pyrrol-5(3H)-yl)methyl)-3-(3,4,5-trifluorophenyl)-1,2,5-oxadiazole 2-oxide (AH-4-69)

$^1$H NMR (CDCl$_3$, 600 MHz): δ8.17-8.13 (2H, m); 3.95-3.93 (2H, q); 3.75 (2H, s); 3.54-3.52 (2H, dd, J=5.0 Hz); 2.92-2.89 (2H, m); 2.76-2.73 (2H, m); 2.69-2.67 (2H, dd, J=7.2 Hz). $^{13}$C NMR (CDCl$_3$, 600 MHz): 154.2, 152.36, 152.33, 152.29, 152.27, 150.70, 150.67, 150.63, 150.61, 141.6, 141.5, 139.99, 139.89, 119.12, 119.09, 119.06, 119.02, 228.99, 118.96, 113.5, 74.2, 58.8, 49.8, 43.5. Measured purity at 254 nm: 95.9%; 282 nm: 97.5%.

4-(((3aR,7aS)-hexahydrofuro[3,2-c]pyridin-5(4H)-yl)methyl)-3-(3,4,5-trifluorophenyl)-1,2,5-oxadiazole 2-oxide (AH-4-70)

$^1$H NMR (CDCl$_3$, 600 MHz): δ8.21-8.17 (2H, m); 4.05-4.01 (1H, q); 3.90-3.86 (2H, m); 3.64-3.57 (2H, q); 2.78-2.75 (1H, m); 2.51-2.47 (1H, td); 2.35-2.32 (1H, br); 2.19-2.15 (1H, t); 2.10-2.03 (2H, m); 1.95-1.89 (1H, m); 1.71-1.66 (1H, m). $^{13}$C NMR (CDCl$_3$, 600 MHz): 153.7, 152.31, 152.28, 152.24, 152.21, 150.65, 150.62, 150.58, 150.55, 141.5, 139.8, 119.25, 119.22, 119.18, 113.7, 112.93, 112.90, 112.80, 112.77, 74.5, 66.1, 53.8, 53.2, 48.4, 37.3, 29.7, 27.7. Measured purity at 254 nm: 99.7%; 282 nm: 99.7%.

4-(((4aR,7aS)-hexahydro-6H-[1,4]dioxino[2,3-c]pyrrol-6-yl)methyl)-3-(3,4,5-trifluorophenyl)-1,2,5-oxadiazole 2-oxide (AH-4-71)

$^1$H NMR (CDCl$_3$, 600 MHz): δ8.10-8.07 (2H, m); 4.21-4.19 (2H, quint); 3.88 (2H, s); 3.87-3.83 (2H, m); 3.66-3.62 (2H, m); 3.06-3.04 (2H, dd, J=10.2 Hz); 3.00-2.97 (2H, m). $^{13}$C NMR (CDCl$_3$, 600 MHz): 154.2, 152.34, 152.31, 152.27, 152.24, 150.68, 150.65, 150.61, 150.59, 141.70, 141.60, 139.99, 139.89, 119.15, 119.12, 119.09, 119.05, 119.02, 118.99, 113.5, 112.97, 112.93, 112.84, 112.80, 73.2, 62.6, 54.2, 50.9. Measured purity at 254 nm: 99.8%; 282 nm: 99.8%.

3-(4-fluorophenyl)-4-(((3aR,6aS)-tetrahydro-1H-furo[3,4-c]pyrrol-5(3H)-yl)methyl)-1,2,5-oxadiazole 2-oxide (AH-4-78)

$^1$H NMR (CDCl$_3$, 600 MHz): δ8.19-8.16 (2H, m); 7.24-7.21 (2H, m); 3.94-3.92 (2H, q); 3.74 (2H, s); 3.46-3.44 (2H, dd, J=4.6 Hz); 2.88-2.86 (2H, m); 2.74-2.72 (2H, m); 2.63-2.61 (2H, dd, J=6.9 Hz). $^{13}$C NMR (CDCl$_3$, 600 MHz): 164.1, 162.8, 154.7, 130.4, 130.3, 119.08, 119.06, 116.3, 116.2, 114.7, 74.1, 58.7, 49.9, 43.6. Measured purity at 254 nm: 99.3%; 282 nm: 99.6%.

3-(4-fluorophenyl)-4-(((3aR,7aS)-hexahydrofuro[3,2-c]pyridin-5(4H)-yl)methyl)-1,2,5-oxadiazole 2-oxide (AH-4-79)

$^1$H NMR (CDCl$_3$, 600 MHz): δ8.21-8.17 (2H, m); 7.24-7.21 (2H, m); 4.03-3.99 (2H, q); 3.88-3.84 (2H, m); 3.63-3.56 (2H, q); 2.77-2.73 (1H, m); 2.68-2.64 (1H, m); 2.47-2.42 (1H, td); 2.30-2.28 (1H, br); 2.14-2.11 (1H, t); 2.08-1.99 (2H, m); 1.91-1.86 (1H, m); 1.68-1.64 (1H, m). $^{13}$C NMR (CDCl$_3$, 600 MHz): 164.4, 162.7, 154.2, 130.43, 130.37, 119.24, 119.22, 116.3, 116.3, 114.9, 74.6, 66.1, 53.9, 53.3, 48.6, 37.4, 29.7, 27.9. Measured purity at 254 nm: 99.6%; 282 nm: 99.7%.

3-(4-fluorophenyl)-4-(((4aR,7aS)-hexahydro-6H-[1,4]dioxino[2,3-c]pyrrol-6-yl)methyl)-1,2,5-oxadiazole 2-oxide (AH-4-80)

$^1$H NMR (CDCl$_3$, 600 MHz): δ8.11-8.09 (2H, m); 7.24-7.22 (2H, m); 4.17-4.15 (2H, quint); 3.88 (2H, s); 3.85-3.81 (2H, m); 3.65-3.61 (2H, m); 3.03-3.02 (4H, m). $^{13}$C NMR (CDCl$_3$, 600 MHz): 164.4, 162.7, 154.6, 130.34, 130.29, 119.09, 119.07, 116.4, 116.3, 114.6, 73.4, 62.7, 54.3, 51.0. Measured purity at 254 nm: 99.3%; 282 nm: 99.5%.

3-(benzo[d][1,3]dioxol-5-yl)-4-(((3aR,6aS)-tetrahydro-1H-furo[3,4-c]pyrrol-5 (3H)-yl)methyl)-1,2,5-oxadiazole 2-oxide (AH-4-88)

$^1$H NMR (CDCl$_3$, 600 MHz): δ7.75-7.74 (2H, d, J=1.7 Hz); 7.71-7.69 (1H, dd, J=6.5 Hz); 6.95-6.94 (1H, d, J=8.2 Hz); 6.07 (2H, s); 3.96-3.94 (2H, q); 3.73 (2H, s); 3.48-3.46 (2H, dd, J=4.4 Hz); 2.88-2.86 (2H, br); 2.73-2.70 (2H, m); 2.65-2.63 (2H, dd, J=7.2 Hz). $^{13}$C NMR (CDCl$_3$, 600 MHz): 154.7, 149.3, 148.2, 122.8, 116.3, 115.7, 108.8, 108.3, 101.7, 74.1, 58.6, 49.8, 43.6. Measured purity at 254 nm: 98.2%; 282 nm: 98.6%.

3-(benzo[d][1,3]dioxol-5-yl)-4-(((3aR,7aS)-hexahydrofuro[3,2-c]pyridin-5(4H)-yl)methyl)-1,2,5-oxadiazole 2-oxide (AH-4-89)

$^1$H NMR (CDCl$_3$, 600 MHz): δ7.774-7.772 (1H, d, J=1.3 Hz); 7.73-7.71 (1H, dd, J=6.8 Hz); 6.96-6.95 (1H, d, J=8.2 Hz); 6.07 (2H, s); 4.03-3.99 (1H, q); 3.89-3.84 (2H, m); 3.60-3.53 (2H, q); 2.78-2.75 (1H, q); 2.68-2.66 (1H, m); 2.47-2.42 (1H, td); 2.32-2.31 (1H, br); 2.15-2.11 (1H, t); 2.08-1.99 (2H, m); 1.94-1.89 (1H, m); 1.70-1.65 (1H, m). $^{13}$C NMR (CDCl$_3$, 600 MHz): 154.2, 149.2, 148.2, 122.9, 116.4, 115.5, 108.8, 108.3, 101.7, 74.7, 66.1, 53.9, 53.2, 48.5, 37.4, 29.7, 27.9. Measured purity at 254 nm: 96.8%; 282 nm: 97.1%.

3-(benzo[d][1,3]dioxol-5-yl)-4-(((4aR,7aS)-hexahydro-6H-[1,4]dioxino[2,3-c]pyrrol-6-yl)methyl)-1,2,5-oxadiazole 2-oxide (AH-4-90)

$^1$H NMR (CDCl$_3$, 600 MHz): δ7.66-7.65 (1H, d, J=1.7 Hz); 7.61-7.60 (1H, dd, J=6.5 Hz); 6.96-6.95 (1H, d, J=8.2 Hz); 6.07 (2H, s); 4.18-4.15 (2H, quint); 3.86-3.83 (4H, m); 3.64-3.62 (2H, m); 3.04-3.02 (4H, m). $^{13}$C NMR (CDCl$_3$, 600 MHz): 154.6, 149.3, 148.3, 122.9, 116.3, 115.2, 108.9, 108.2, 101.7, 73.4, 62.7, 54.3, 51.0. Measured purity at 254 nm: 97.9%; 282 nm: 98.3%.

4-(((3aR,6aS)-tetrahydro-1H-furo[3,4-c]pyrrol-5 (3H)-yl)methyl)-3-(4-(trifluoromethoxy)phenyl)-1,2,5-oxadiazole 2-oxide (AH-4-92)

$^1$H NMR (CDCl$_3$, 600 MHz): δ8.25-8.24 (2H, d, J=9.0 Hz); 7.38-7.37 (2H, d, J=8.3 Hz); 3.94-3.92 (2H, q); 3.75 (2H, s); 3.47-3.45 (2H, dd, J=4.8 Hz); 2.88 (2H, br); 2.76-2.73 (2H, m); 2.64-2.62 (2H, dd, J=7.1 Hz). $^{13}$C NMR (CDCl$_3$, 600 MHz): 154.6, 150.4, 129.9, 122.9, 121.6, 121.2, 119.5, 117.8, 114.5, 74.1, 58.8, 49.9, 43.6. Measured purity at 254 nm: 99.7%; 282 nm: 99.5%.

4-(((3aR,7aS)-hexahydrofuro[3,2-c]pyridin-5(4H)-yl)methyl)-3-(4-(trifluoromethoxy)phenyl)-1,2,5-oxadiazole 2-oxide (AH-4-93)

$^1$H NMR (CDCl$_3$, 600 MHz): δ8.27-8.26 (2H, d, J=8.9 Hz); 7.39-7.37 (2H, d, J=8.3 Hz); 4.03-3.99 (2H, q); 3.88-3.84 (2H, m); 3.64-3.57 (2H, q); 2.77-2.74 (1H, q); 2.68-2.66 (1H, m); 2.48-2.43 (1H, td); 2.30-2.29 (1H, br); 2.15-2.12 (1H, t); 2.08-2.00 (2H, m); 1.91-1.85 (1H, m); 1.68-1.63 (1H, m). $^{13}$C NMR (CDCl$_3$, 600 MHz): 154.1, 150.3, 129.9, 122.9, 121.8, 121.2, 121.1, 119.5, 117.8, 114.8, 74.6, 66.1, 53.9, 53.3, 48.6, 37.4, 29.7, 27.9. Measured purity at 254 nm: 99.6%; 282 nm: 99.5%.

4-(((4aR,7aS)-hexahydro-6H-[1,4]dioxino[2,3-c]pyrrol-6-yl)methyl)-3-(4-(trifluoromethoxy)phenyl)-1,2,5-oxadiazole 2-oxide (AH-2-94)

$^1$H NMR (CDCl$_3$, 600 MHz): δ8.19-8.17 (2H, m); 7.39-7.37 (2H, d, J=8.3 Hz); 4.18-4.15 (2H, quint); 3.89 (2H, s); 3.85-3.81 (2H, m); 3.65-3.61 (2H, m); 3.03-3.02 (4H, d, J=5.1 Hz). $^{13}$C NMR (CDCl$_3$, 600 MHz): 154.6, 150.3, 129.9, 122.9, 121.6, 121.2, 119.5, 117.8, 114.4, 73.3, 62.7, 54.3, 51.0. Measured purity at 254 nm: 99.1%; 282 nm: 99.3%.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising Formula I:

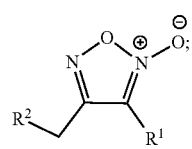

Formula I wherein:

R¹ is a substituted or unsubstituted aryl group; and

R² is a substituted or unsubstituted heterocyclic amine wherein the heterocyclic amine does not contain more than one N, where N is attached to the CH₂ group of Formula I.

2. The compound of claim 1, wherein the heterocyclic amine includes piperidines, piperazines, thiomorpholines, morpholines, and pyrrolidines.

3. The compound of claim 1, wherein R² is a deuterium-substituted heterocyclic amine.

4. The compound of claim 1, wherein R¹ is selected from the group consisting of phenyl, 4-fluorophenyl, 4-bromophenyl, 4-clorophenyl, 4-tetrafluoromethylphenyl, 4-difluoromethoxyphenyl, 4-nitrophenyl, 4-tetrafluoromethyoxyphenyl, and 4-methylphenyl.

5. The compound of claim 1, wherein the compound is compound:

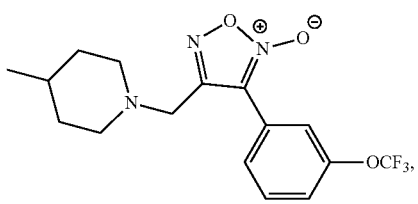 [SMILES: CC1CCN(Cc2no[n+]([O-])c2-c2cccc(OC(F)(F)F)c2)CC1]

4-((4-methylpiperidin-1-yl)methyl)-3-(3-(trifluoromethoxy)phenyl)-1,2,5-oxadiazole 2-oxide (AH-4-52).

6. The compound of claim 1, wherein the compound is compound:

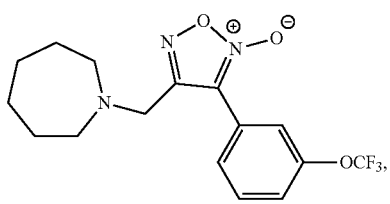 [SMILES: [O-][n+]1onc(CN2CCCCCC2)c1-c1cccc(OC(F)(F)F)c1]

4-(azepan-1-ylmethyl)-3-(3-(trifluoromethoxy)phenyl)-1,2,5-oxadiazole 2-oxide (AH-4-53).

7. The compound of claim 1, wherein the compound is compound:

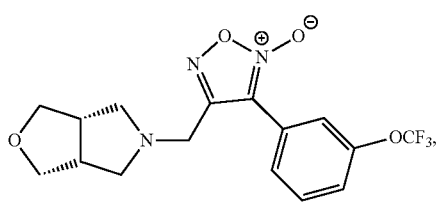

4-(((3aR,6aS)-tetrahydro-1H-furo[3,4-c]pyrrol-5(3H)-yl)methyl)-3-(3-(trifluoromethoxy)phenyl)-1,2,5-oxadiazole 2-oxide (AH-4-54).

8. The compound of claim 1, wherein the compound is compound:

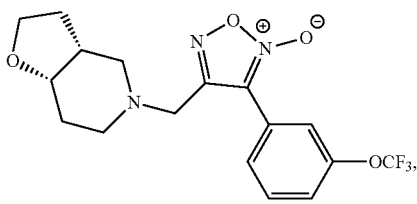 [SMILES: [O-][n+]1onc(CN2CC[C@@H]3OCC[C@@H]3C2)c1-c1cccc(OC(F)(F)F)c1]

4-(((3aR,7aS)-hexahydrofuro[3,2-c]pyridin-5(4H)-yl)methyl)-3-(3-(trifluoromethoxy)phenyl)-1,2,5-oxadiazole 2-oxide (AH-4-55).

9. The compound of claim 1, wherein the compound is compound:

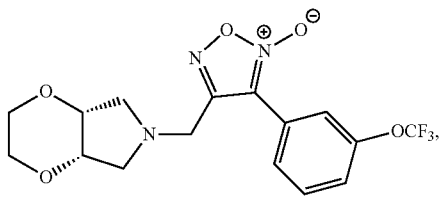 [SMILES: [O-][n+]1onc(CN2C[C@@H]3OCCO[C@@H]3C2)c1-c1cccc(OC(F)(F)F)c1]

4-(((4aR,7aS)-hexahydro-6H-[1,4]dioxino[2,3-c]pyrrol-6-yl)methyl)-3-(3-(trifluoromethoxy)phenyl)-1,2,5-oxadiazole 2-oxide (AH-4-56).

10. The compound of claim 1, wherein the compound is compound:

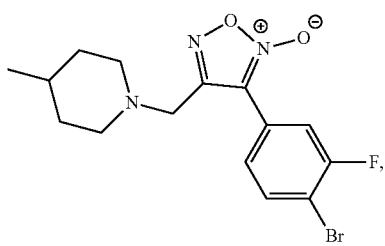 [SMILES: CC1CCN(Cc2no[n+]([O-])c2-c2ccc(Br)c(F)c2)CC1]

3-(4-bromo-3-fluorophenyl)-4-((4-methylpiperidin-1-yl)methyl)-1,2,5-oxadiazole 2-oxide (AH-4-58).

11. The compound of claim 1, wherein the compound is compound:

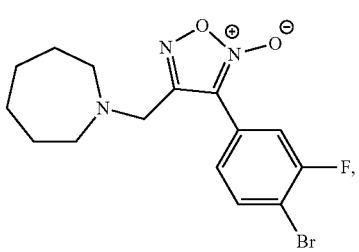 [SMILES: [O-][n+]1onc(CN2CCCCCC2)c1-c1ccc(Br)c(F)c1]

4-(azepan-1-ylmethyl)-3-(4-bromo-3-fluorophenyl)-1,2,5-oxadiazole 2-oxide (AH-4-59).

12. The compound of claim 1, wherein the compound is compound:

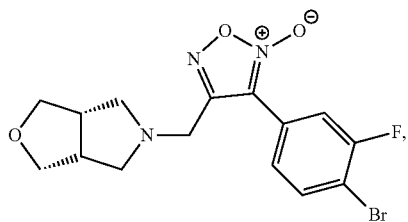

3-(4-bromo-3-fluorophenyl)-4-(((3aR,6aS)-tetrahydro-1H-furo[3,4-c]pyrrol-5(3H)-yl)methyl)-1,2,5-oxadiazole 2-oxide (AH-4-60).

13. The compound of claim 1, wherein the compound is compound:

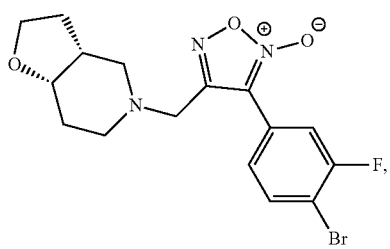 [SMILES: [O-][n+]1onc(CN2CC[C@@H]3OCC[C@@H]3C2)c1-c1ccc(Br)c(F)c1]

3-(4-bromo-3-fluorophenyl)-4-(((3aR,7aS)-hexahydrofuro[3,2-c]pyridin-5(4H)-yl)methyl)-1,2,5-oxadiazole 2-oxide (AH-4-61).

14. The compound of claim 1, wherein the compound is compound:

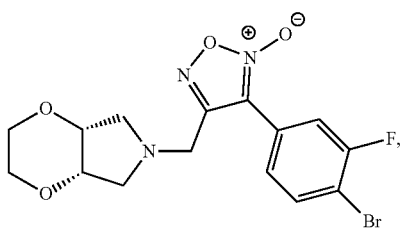 [SMILES: [O-][n+]1onc(CN2C[C@@H]3OCCO[C@@H]3C2)c1-c1ccc(Br)c(F)c1]

3-(4-bromo-3-fluorophenyl)-4-(((4aR,7aS)-hexahydro-6H-[1,4]dioxino[2,3-c]pyrrol-6-yl)methyl)-1,2,5-oxadiazole 2-oxide (AH-4-62).

15. The compound of claim 1, wherein the compound is compound:

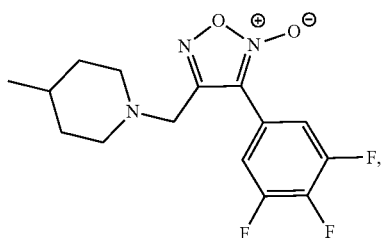 [SMILES: CC1CCN(Cc2no[n+]([O-])c2-c2cc(F)c(F)c(F)c2)CC1]

4-((4-methylpiperidin-1-yl)methyl)-3-(3,4,5-trifluorophenyl)-1,2,5-oxadiazole 2-oxide (AH-4-67).

16. The compound of claim 1, wherein the compound is compound:

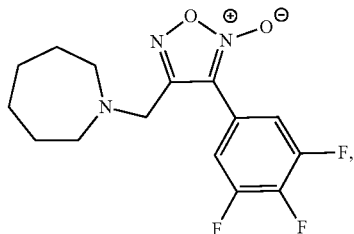 [SMILES: [O-][n+]1onc(CN2CCCCCC2)c1-c1cc(F)c(F)c(F)c1]

4-(azepan-1-ylmethyl)-3-(3,4,5-trifluorophenyl)-1,2,5-oxadiazole 2-oxide (AH-4-68).

17. The compound of claim 1, wherein the compound is compound:

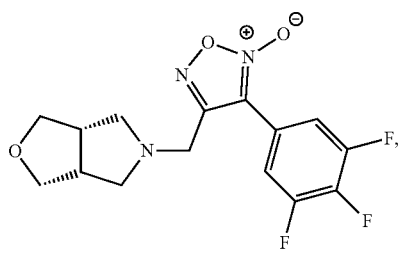

4-(((3aR,6aS)-tetrahydro-1H-furo[3,4-c]pyrrol-5(3H)-yl)methyl)-3-(3,4,5-trifluorophenyl)-1,2,5-oxadiazole 2-oxide (AH-4-69).

18. The compound of claim 1, wherein the compound is compound:

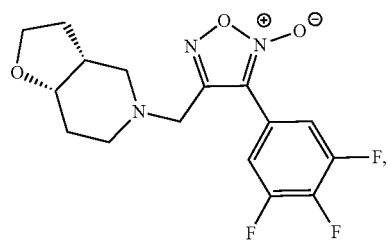 [SMILES: [O-][n+]1onc(CN2CC[C@@H]3OCC[C@@H]3C2)c1-c1cc(F)c(F)c(F)c1]

4-(((3aR,7aS)-hexahydrofuro[3,2-c]pyridin-5(4H)-yl)methyl)-3-(3,4,5-trifluorophenyl)-1,2,5-oxadiazole 2-oxide (AH-4-70).

19. The compound of claim 1, wherein the compound is compound:

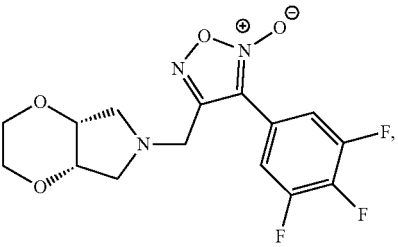 [SMILES: [O-][n+]1onc(CN2C[C@@H]3OCCO[C@@H]3C2)c1-c1cc(F)c(F)c(F)c1]

4-(((4aR,7aS)-hexahydro-6H-[1,4]dioxino[2,3-c]pyrrol-6-yl)methyl)-3-(3,4,5-trifluorophenyl)-1,2,5-oxadiazole 2-oxide (AH-4-71).

20. The compound of claim 1, wherein the compound is f compound:

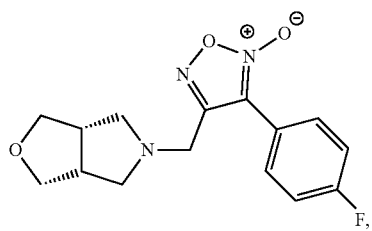

3-(4-fluorophenyl)-4-(((3aR,6aS)-tetrahydro-1H-furo[3,4-c]pyrrol-5(3H)-yl)methyl)-1,2,5-oxadiazole 2-oxide (AH-4-78).

21. The compound of claim 1, wherein the compound is compound:

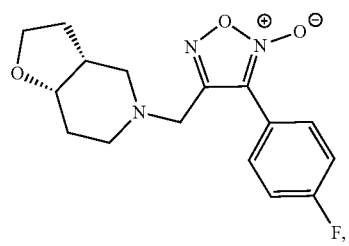 [SMILES: [O-][n+]1onc(CN2CC[C@@H]3OCC[C@@H]3C2)c1-c1ccc(F)cc1]

3-(4-fluorophenyl)-4-(((3aR,7aS)-hexahydrofuro[3,2-c]pyridin-5(4H)-yl)methyl)-1,2,5-oxadiazole 2-oxide (AH-4-79).

22. The compound of claim 1, wherein the compound is compound:

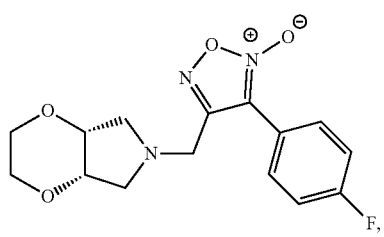 [SMILES: [O-][n+]1onc(CN2C[C@@H]3OCCO[C@@H]3C2)c1-c1ccc(F)cc1]

3-(4-fluorophenyl)-4-(((4aR,7aS)-hexahydro-6H-[1,4]dioxino[2,3-c]pyrrol-6-yl)methyl)-1,2,5-oxadiazole 2-oxide (AH-4-80).

23. The compound of claim 1, wherein the compound is compound:

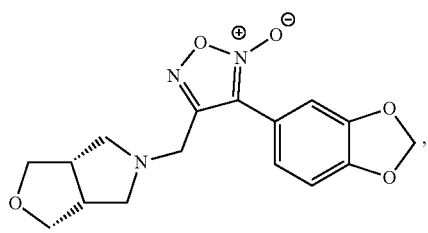

3-(benzo [d][1,3]dioxol-5-yl)-4-(((3aR,6aS)-tetrahydro-1H-furo[3,4-c]pyrrol-5(3H)-yl)methyl)-1,2,5-oxadiazole 2-oxide (AH-4-88).

24. The compound of claim 1, wherein the compound is compound:

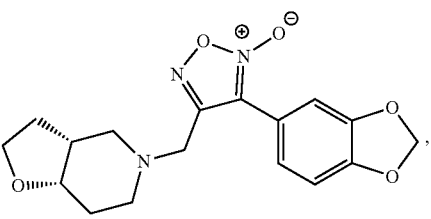 [SMILES: [O-][n+]1onc(CN2CC[C@@H]3OCC[C@@H]3C2)c1-c1ccc2c(c1)OCO2]

3-(benzo [d][1,3]dioxol-5-yl)-4-(((3aR,7aS)-hexahydrofuro[3,2-c]pyridin-5(4H)-yl)methyl)-1,2,5-oxadiazole 2-oxide (AH-4-89).

25. The compound of claim 1, wherein the compound is compound:

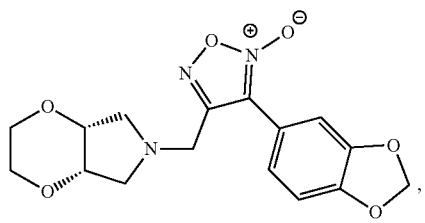 [SMILES: [O-][n+]1onc(CN2C[C@@H]3OCCO[C@@H]3C2)c1-c1ccc2c(c1)OCO2]

3-(benzo[d][1,3]dioxol-5-yl)-4-(((4aR,7aS)-hexahydro-6H-[1,4]dioxino[2,3-c]pyrrol-6-yl)methyl)-1,2,5-oxadiazole 2-oxide (AH-4-90).

26. The compound of claim 1, wherein the compound is compound:

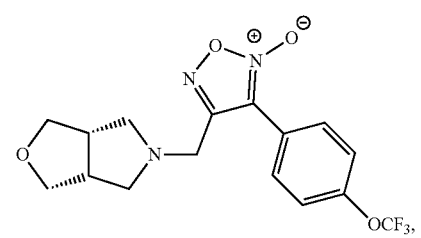

4-(((3aR,6aS)-tetrahydro-1H-furo[3,4-c]pyrrol-5(3H)-yl)methyl)-3-(4-(trifluoromethoxy)phenyl)-1,2,5-oxadiazole 2-oxide (AH-4-92).

27. The compound of claim 1, wherein the compound is compound:

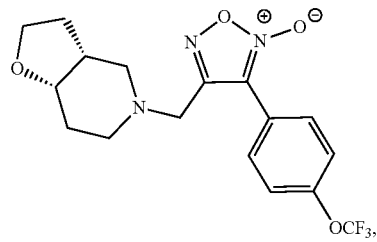 [SMILES: [O-][n+]1onc(CN2CC[C@@H]3OCC[C@@H]3C2)c1-c1ccc(OC(F)(F)F)cc1]

4-(((3aR,7aS)-hexahydrofuro[3,2-c]pyridin-5(4H)-yl)methyl)-3-(4-(trifluoromethoxy)phenyl)-1,2,5-oxadiazole 2-oxide (AH-4-93).

28. The compound of claim 1, wherein the compound is compound:

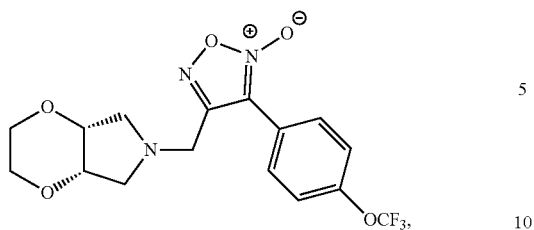
4-(((4aR,7aS)-hexahydro-6H-[1,4]dioxino[2,3-c]pyrrol-6-yl)methyl)-3-(4-(trifluoromethoxy)phenyl)-1,2,5-oxadiazole 2-oxide (AH-2-94).
\* \* \* \* \*